(12) United States Patent
Bromley

(10) Patent No.: US 8,337,931 B2
(45) Date of Patent: Dec. 25, 2012

(54) COMPOSITIONS CONTAINING NON-POLAR COMPOUNDS

(75) Inventor: Philip J. Bromley, Fullerton, CA (US)

(73) Assignee: Virun, Inc., Walnut, CA (US)

( * ) Notice: Subject to any disclaimer, the term of this patent is extended or adjusted under 35 U.S.C. 154(b) by 477 days.

(21) Appl. No.: 12/456,926

(22) Filed: Jun. 23, 2009

(65) Prior Publication Data
US 2009/0317532 A1 Dec. 24, 2009

Related U.S. Application Data

(60) Provisional application No. 61/132,953, filed on Jun. 23, 2008.

(51) Int. Cl.
*A23D 7/00* (2006.01)
(52) U.S. Cl. .................................. 426/602; 426/590
(58) Field of Classification Search .................. 426/602, 426/590
See application file for complete search history.

(56) References Cited

U.S. PATENT DOCUMENTS

| | | | |
|---|---|---|---|
| 4,353,365 A | 10/1982 | Hallworth et al. | 128/203.15 |
| 4,524,769 A | 6/1985 | Wetterlin | 128/203.15 |
| 4,670,285 A | 6/1987 | Clandinin et al. | 426/602 |
| 4,835,002 A * | 5/1989 | Wolf et al. | 426/590 |
| 4,916,163 A | 4/1990 | Ni | 514/593 |
| 5,035,237 A | 7/1991 | Newell et al. | 128/203.15 |
| 5,239,993 A | 8/1993 | Evans | 128/203.15 |
| 5,397,591 A | 3/1995 | Kyle et al. | 426/602 |
| 5,407,957 A | 4/1995 | Kyle et al. | 514/547 |
| 5,415,162 A | 5/1995 | Casper et al. | 128/203.12 |
| 5,430,021 A | 7/1995 | Rudnic et al. | 514/14 |
| 5,492,938 A | 2/1996 | Kyle et al. | 514/786 |
| 5,593,682 A | 1/1997 | Papas et al. | 424/401 |
| 5,711,983 A | 1/1998 | Kyle et al. | 426/635 |
| 5,715,810 A | 2/1998 | Armstrong | 128/203.15 |
| 6,045,826 A | 4/2000 | Borowy-Borowski et al. | 424/451 |
| 6,048,566 A | 4/2000 | Behnam et al. | 426/590 |
| 6,054,261 A | 4/2000 | Masterson | 435/1.2 |
| 6,056,971 A | 5/2000 | Goldman | 424/439 |
| 6,162,474 A * | 12/2000 | Chen et al. | 426/72 |
| 6,180,130 B1 * | 1/2001 | Chen et al. | 424/439 |
| 6,184,255 B1 | 2/2001 | Mae et al. | 514/720 |
| 6,200,550 B1 | 3/2001 | Masterson et al. | 424/49 |
| 6,248,363 B1 | 6/2001 | Patel et al. | 424/497 |
| 6,267,985 B1 | 7/2001 | Chen et al. | 424/451 |
| 6,284,268 B1 | 9/2001 | Mishra et al. | 424/455 |
| 6,335,022 B1 * | 1/2002 | Simonnet et al. | 424/401 |
| 6,378,519 B1 | 4/2002 | Davies et al. | 128/203.21 |
| 6,391,370 B1 * | 5/2002 | Rogers et al. | 426/611 |
| 6,441,050 B1 | 8/2002 | Chopra | 514/675 |
| 6,509,044 B2 * | 1/2003 | Van Den Braak et al. | 426/2 |
| 6,534,085 B1 | 3/2003 | Zeligs | 424/451 |
| 6,870,077 B2 | 3/2005 | Kenaschuk | 800/298 |
| 6,908,626 B2 | 6/2005 | Cooper et al. | 424/489 |
| 6,923,988 B2 | 8/2005 | Patel et al. | 424/489 |
| 6,977,166 B1 | 12/2005 | Ratledge et al. | 435/134 |
| 6,982,281 B1 | 1/2006 | Chen et al. | 514/458 |
| 7,015,252 B2 | 3/2006 | Fujii et al. | 514/690 |
| 7,026,361 B2 | 4/2006 | Minemura et al. | 516/75 |
| 7,030,102 B1 | 4/2006 | Madhavi et al. | 514/58 |
| 7,087,238 B2 | 8/2006 | Hamamoto et al. | 424/401 |
| 7,094,804 B2 | 8/2006 | Behnam | 514/460 |
| 7,145,044 B2 | 12/2006 | Ueda et al. | 568/823 |
| 7,182,950 B2 | 2/2007 | Garti et al. | 424/401 |
| 7,273,624 B2 | 9/2007 | Rosenberg et al. | 424/489 |
| 2001/0025058 A1 | 9/2001 | Borowy-Borowski et al. | 514/772.4 |
| 2003/0031688 A1 | 2/2003 | Ghosh et al. | 424/401 |
| 2003/0064097 A1 | 4/2003 | Patel et al. | 424/465 |
| 2003/0180352 A1 | 9/2003 | Patel et al. | 424/465 |
| 2004/0033202 A1 | 2/2004 | Cooper et al. | 424/46 |
| 2004/0072330 A1 | 4/2004 | Ratledge et al. | 435/258.1 |
| 2004/0105889 A1 | 6/2004 | Ryde et al. | 424/489 |
| 2004/0121043 A1 * | 6/2004 | Behnam | 426/72 |
| 2004/0219274 A1 | 11/2004 | Cook | 426/590 |
| 2005/0008581 A1 | 1/2005 | Parkhideh | 424/46 |
| 2005/0208082 A1 | 9/2005 | Papas et al. | 424/400 |
| 2005/0260752 A1 * | 11/2005 | Wilding et al. | 435/373 |
| 2005/0281772 A1 | 12/2005 | Bromley et al. | 424/70.14 |
| 2006/0034937 A1 | 2/2006 | Patel | 424/497 |
| 2006/0051462 A1 | 3/2006 | Wang | 426/72 |
| 2006/0088558 A1 | 4/2006 | Jandzinski et al. | 424/400 |
| 2006/0165735 A1 | 7/2006 | Abril et al. | 424/401 |
| 2006/0287384 A1 | 12/2006 | Behnham | 514/440 |
| 2007/0043106 A1 | 2/2007 | Behnham | 514/440 |

(Continued)

FOREIGN PATENT DOCUMENTS
CN 1236304 A 11/1999
(Continued)

OTHER PUBLICATIONS

Certified English translation of German patent DE 10 2005 049664, published Apr. 19, 2007, entitled: "Liquid Composition and Method for its Production," Inventor—Haller, 9 pages.
"Virun Omega 3 Fortified Foods and Beverages," retrieved from the Internet:<URL: slideshare.net/virun/virun-omega-3-fortified-foods-and-beverages, [retrieved on May 7, 2010] [15 pages].
Covington, M., "Omega-3 fatty acids," American Family Physician 70(1):133-140 (2004).

(Continued)

*Primary Examiner* — Carolyn Paden
(74) *Attorney, Agent, or Firm* — McKenna Long & Aldridge LLP; Stephanie Seidman

(57) ABSTRACT

Provided herein are compositions and methods for preparing foods and beverages that contain additives. Additives include nutraceuticals, pharmaceuticals, and supplements, such as essential fatty acids, including omega-3 fatty acids, omega-6 fatty acids, conjugated fatty acids, and other fatty acids; phytochemicals, including phytosterols; other oils; and coenzymes, including Coenzyme Q10, and other oil-based additives.

64 Claims, 1 Drawing Sheet

U.S. PATENT DOCUMENTS

| | | | |
|---|---|---|---|
| 2007/0087104 A1* | 4/2007 | Chanamai | 426/602 |
| 2007/0104778 A1 | 5/2007 | Zeng et al. | 424/451 |
| 2007/0104780 A1 | 5/2007 | Lipari et al. | 424/456 |
| 2007/0166411 A1 | 7/2007 | Anthony et al. | 424/750 |
| 2007/0184117 A1 | 8/2007 | Gregory et al. | 424/489 |
| 2007/0213234 A1 | 9/2007 | Yaghmur et al. | 508/110 |
| 2008/0070981 A1 | 3/2008 | Borowy-Borowski et al. | 514/458 |
| 2008/0254188 A1 | 10/2008 | Borowy-Borowski et al. | 426/590 |
| 2009/0018186 A1 | 1/2009 | Chen et al. | 426/590 |
| 2009/0297491 A1 | 12/2009 | Bromley | 424/94.1 |
| 2009/0297665 A1 | 12/2009 | Bromley | 426/72 |
| 2010/0041622 A1 | 2/2010 | Bromley et al. | 514/52 |
| 2010/0080785 A1 | 4/2010 | Berl | 424/94.1 |
| 2011/0008305 A1* | 1/2011 | Yu et al. | 424/94.1 |
| 2011/0117184 A1 | 5/2011 | Bromley | 424/450 |
| 2011/0236364 A1 | 9/2011 | Bromley | 424/94.1 |
| 2012/0016026 A1 | 1/2012 | Bromley | 514/560 |

FOREIGN PATENT DOCUMENTS

| | | |
|---|---|---|
| DE | 10 2005 049664 | 4/2007 |
| EP | 1972334 | 9/2008 |
| WO | WO 96/36316 | 11/1996 |
| WO | WO 98/15195 | 4/1998 |
| WO | WO 99/59421 | 11/1999 |
| WO | WO 00/23545 | 4/2000 |
| WO | WO 02/17879 | 3/2002 |
| WO | WO 2004/098311 | 11/2004 |
| WO | WO 2006/009825 | 1/2006 |
| WO | WO 2007/016073 | 2/2007 |
| WO | WO 2007/080515 | 7/2007 |
| WO | WO 2008/039564 | 4/2008 |
| WO | WO 2009/117151 | 9/2009 |
| WO | WO 2009/117152 | 9/2009 |
| WO | WO 2010/008475 | 1/2010 |
| WO | WO 2010/019255 | 2/2010 |

OTHER PUBLICATIONS

Ernst, E., "The risk-benefit profile of commonly used herbal therapies: Ginkgo, St. John's Wort, Ginseng, Echinacea, Saw Palmetto, and Kava," Ann Intern Med. 136:42-53 (2002).

Fan, Y. and R. Chapkin, "Importance of dietary γ-linolenic acid in human health and nutrition," Journal of Nutrition 1411-1414 (1998).

Gordon, A. and A. Shaughnessy, "Saw palmetto for prostate disorders," American Family Physician 67(6):1281-1283 (2003).

Griffin, W., "Classification of surface-reactive agents by HLB," J. Soc. Cos. Chem. 1:311-326 (1949).

Lands, W., "Biochemistry and physiology of n-3 fatty acids," The FASEB Journal, 6(8):2530-2536 (1992).

Offer for Sale, "Kaneka Liquid CoQ10" formulation, to Kaneka Nutrients L.P., Pasadena, TX, on Jun. 22-27, 2007, 2 pages.

Perry's Chemical Engineers' Handbook, pp. 20-54 to 20-57, ed. R. Perry, Published New York : McGraw-Hill (1984).

Ross et al., "Omega-3 fatty acids as treatments for mental illness: which disorder and which fatty acid?," Lipids in Health and Disease 6:21 pp. 1-19 (2007).

Starling, S., "Virun debuts shelf-stable, H20 soluble, nanotech omega-3," found at: www.beveragedaily.com/Products/Vinin-debuts-shelf-stable-H20-soluble-nanotech-omega-3, Beveragedaily.com News Release Mar. 12, 2009. [2 pages].

Virun Clear Water Soluble Omega-3 DHA, EPA & ALA for Foods & Beverages found at: www.slideshare.net/virun/virun-food-beverage-division-v2 [accessed on May 11, 2009] [9 pages].

Virun home Webpage found at: www.virun.com [accessed on May 8, 2009] [34 pages].

Virun Improving Life Through Safe & Effective Oral Delivery found at: www.slideshare.net/virun/virun-improving-life-through-safe-effective-oral-delivery [accessed on Aug. 13, 2009] [15 pages].

Virun on slideshare.net, Philip Bromley's Presentations on SlideShare found at: www.slideshare.net/virun [accessed on Aug. 13, 2009] [5 pages].

Virun Pharmaceutical & Food Beverage Divisions: www.slideshare.net/virun/virun-food-beverage-divisions [accessed on Aug. 12, 2009] [9 pages].

Virun Product Sheet, "Clear oils for water based beverages," Jan. 16, 2009. [4 pages].

Wright, R., "Companies to watch—Nutraceuticals World," located at: www.nutraceuticalsworld.com/articles/2009/06/comoanies-to-watch, (2009) [accessed on Jun. 4, 2009] [7 pages].

Letter/Written Disclosure of the Supplemental Information Disclosure Statement for the above-referenced application, mailed on May 4, 2012, 2 pages.

Chanana, G. and B. Sheth, "Particle size reduction of emulsions by formulation design-II: effect of oil and surfactant concentration, " PDA J Pharm Sci Technol. 49(2):71-76 (1995).

Kassem et al., "Preparation and in vitro evaluation of self-nanoemulsifying drug delivery systems (SNEDDS) containing clotrimazole," Drug Discoveries & Therapeutics. 4(5):373-379 (2010).

Landfester, K., "Miniemulsions for Nanoparticle Synthesis: Formation of particles in inverse microemulsion," Colloid Cheimstry II, vol. 227. Ed. M. Antionietti. New York: Springer, 2003 pp. 97-99.

Pokhriyal et al., "Kinetics and behavior of copolymerization in emulsion and microemulsion systems," Langmuir. 16:5864-5870 (2000).

Tadros, T., "Emulsion science and technology: a general introduction," Emulsion Science and Technology. Ed. T. Tadros. Wienheim: Wiley-VCH, 2009, pp. 1-56.

Zaghloul et al., "Development, characterization and optimization of ibuprofen self-emulsifying drug delivery system applying face centered experimental design," International Journal of Pharmacy and Technilogy; 3(1):1674-1693 (2011).

Response of Jan. 23, 2012 to Written Opinion issued for related International Application No. PCT/US2011/000538, 9 pages.

Letter/Written Disclosure of the Information Disclosure Statement for the above-referenced application, mailed on Dec. 8, 2011, 2 pages.

Eastman PCI-102B Publication, "Vitamin E TPGS NF—applications and properties," Eastman Chemical Company, Publication PCI-102B, Oct. 2005, 24 pages.

Virun home Webpage [online][retrieved on Mar. 24, 2011] Retrieved from:<URL:virun.com [59 pages].

Virun Intricate Science [online][retrieved on May 25, 2011] Retrieved from:<URL:slideshare.net/virun/virun-intricate-science [22 pages].

Response to Written Opinion, issued Jul. 3, 2009, in connection with related International Patent Application No. PCT/US2009/001775, 35 pages.

Response to Written Opinion, issue Feb. 4, 2010, in connection with corresponding International Application No. PCT/US2009/003761, 25 pages.

Response to Written Opinion, issued Apr. 1, 2010, in connection with related International Patent Application No. PCT/US2009/001774, 37 pages.

International Preliminary Report on Patentability, issued Jun. 11, 2010, in connection with related International Patent Application No. PCT/US2009/001775, 18 pages.

International Preliminary Report on Patentability, issued Jul. 27, 2010, in connection with related International Patent Application No. PCT/US2009/003761, 13 pages.

International Preliminary Report on Patentability, issued Sep. 3, 2010, in connection with related International Patent Application No. PCT/US2009/001774, 15 pages.

Examination Report, issued Mar. 7, 2011, in connection with related Eurpoean Patent Application No. 09722985.0, 6 pages.

Response to Examination Report, issued Mar. 7, 2011, in connection with related Eurpoean Patent Application No. 09722985.0, 8 pages.

International Search Report and Written Opinion, issued Jul. 22, 2011, for related International Application No. PCT/US2011/000538, 10 pages.

Office Action and Search Report, issued Jun. 25, 2012, and received Aug. 2, 2012, in connection with Chinese Patent Application No. 200980132984.6, 10 pages.

* cited by examiner

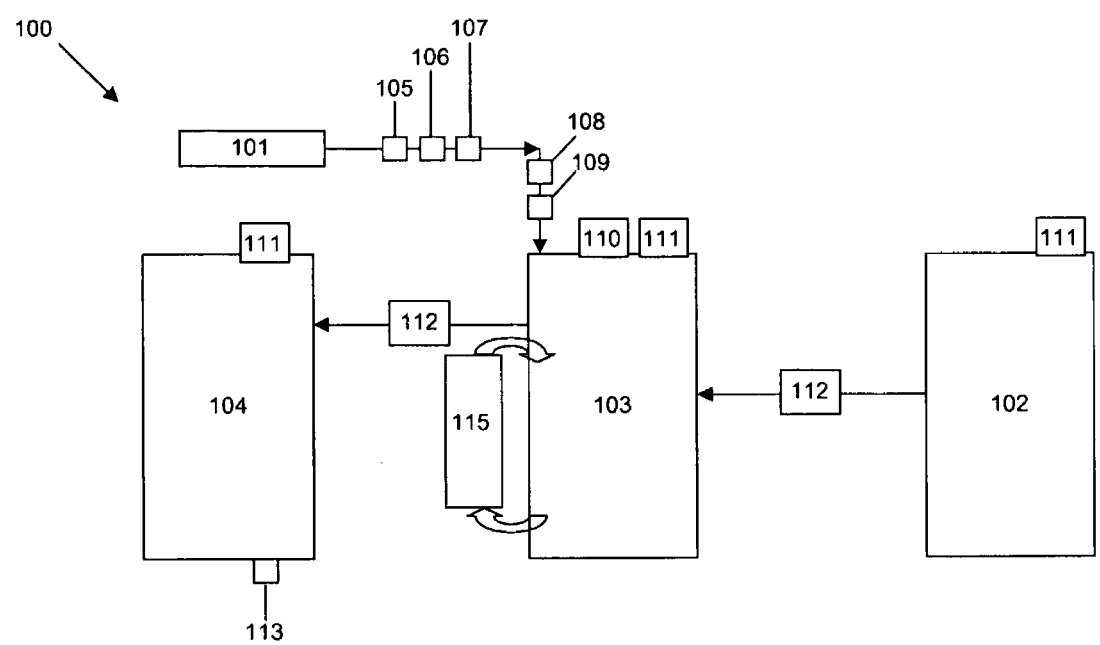

US 8,337,931 B2

COMPOSITIONS CONTAINING NON-POLAR COMPOUNDS

RELATED APPLICATIONS

Benefit of priority is claimed under 35 U.S.C. §119(e) to U.S. Provisional Application Ser. No. 61/132,953, filed Jun. 23, 2008, entitled "COMPOSITIONS CONTAINING NON-POLAR COMPOUNDS" to Philip Bromley.

This application is related to International Application No. PCT/US09/003761, filed Jun. 23, 2009, entitled "COMPOSITIONS CONTAINING NON-POLAR COMPOUNDS," which also claims priority to U.S. Provisional Application Ser. No. 61/132,953.

This application also is related to U.S. application Ser. No. 12/383,244, filed Mar. 20, 2009, entitled "COMPOSITIONS CONTAINING NON-POLAR COMPOUNDS," and International Application No. PCT/US2009/001775, filed Mar. 20, 2009, entitled "COMPOSITIONS CONTAINING NON-POLAR COMPOUNDS," both of which claim priority to U.S. Provisional Application Ser. No. 61/070,381, filed Mar. 20, 2008, entitled "COMPOSITIONS CONTAINING NON-POLAR COMPOUNDS;" U.S. Provisional Application Ser. No. 61/132,424, filed Jun. 16, 2008, entitled "COMPOSITIONS CONTAINING NON-POLAR COMPOUNDS," each to Philip Bromley.

This application also is related to U.S. patent application Ser. No. 12/383,241, filed Mar. 20, 2009, entitled "COMPOSITIONS CONTAINING NON-POLAR COMPOUNDS" and International Application No. PCT/US2009/001774, filed Mar. 20, 2009, entitled "COMPOSITIONS CONTAINING NON-POLAR COMPOUNDS," both of which claim priority to U.S. Provisional Application Ser. No. 61/070,392, filed Mar. 20, 2008, entitled "COMPOSITIONS CONTAINING NON-POLAR COMPOUNDS" and U.S. Provisional Application Ser. No. 61/132,409, filed Jun. 16, 2008, entitled "COMPOSITIONS CONTAINING NON-POLAR COMPOUNDS" each to Philip Bromley.

The subject matter of each of the above-referenced applications is incorporated by reference in its entirety.

FIELD OF THE INVENTION

Provided are compositions and methods for preparing foods and beverages that contain additives, such as nutraceuticals, pharmaceuticals and supplements.

BACKGROUND

Non-polar compounds are not easily dissolved in aqueous solutions, such as water. A number of non-polar compounds are used in compositions for human ingestion, for example, pharmaceuticals, nutraceuticals and/or dietary supplements. Exemplary of non-polar compounds used in such compositions are vitamins and minerals, fatty acids, and other non-polar compounds, non-polar active agents and non-polar active ingredients.

Because of poor water solubility, inclusion of non-polar compounds in products for human consumption, for example, supplements, foods and beverages, often is challenging. Available compositions containing non-polar compounds, particularly aqueous compositions containing non-polar compounds, and methods for formulating such compositions, are limited. Thus, there remains a need to develop compositions containing non-polar compounds and methods for making the compositions. Accordingly, it is among the objects herein to provide compositions, including aqueous compositions, containing non-polar compounds and methods for making the compositions.

SUMMARY

Provided are first compositions (concentrates) that contain non-polar compounds, including liquid nanoemulsion concentrates. Also provided are methods that use such first compositions to prepare other compositions, such as beverages and other aqueous liquids, into which the first compositions are diluted to form liquid dilution compositions. Also provided are liquid dilution compositions containing the beverage or other aqueous liquid and the diluted concentrate. The concentrates contain dispersions, and/or can be used to prepare dispersions, of effective amounts of additives, such as non-polar compounds, including non-polar active ingredients, such as nutraceuticals, pharmaceuticals, and supplements, such as essential fatty acids, including polyunsaturated fatty acids, such as omega-3 fatty acids, omega-6 fatty acids, conjugated fatty acids, and other fatty acids; phytochemicals, including phytosterols; other oils; and coenzymes, including Coenzyme Q10, and other oil-based additives. The amounts in the resulting diluted compositions are effective to supplement the diet. The compositions provided herein are stable dispersions without phase separation and other changes.

The concentrates, for example, the liquid nanoemulsion concentrates, contain one or more surfactant (typically a surfactant that is a PEG-derived surfactant, typically a polysorbate, such as a polysorbate 80) and a non-polar compound (typically a non-polar active ingredient) other than the surfactant.

The amount of non-polar compound (e.g. non-polar active ingredient) is between 5% or about 5% and 10% or about 10%, by weight, of the concentrate; the amount of surfactant is between 16% or about 16% and 30% or about 30%, by weight, of the concentrate; and the amount of water is between 60% or about 60% and 79% or about 79%, by weight, of the concentrate, for example, at or about 60, 61, 62, 63, 64, 65, 66, 67, 68, 69, 70, 71, 72, 73, 74, 75, 76, 77, 78 or 79%, by weight, of the concentrate.

In one embodiment, the amount of water is between 65% or about 65% and 79% or about 79%, between 65% or about 65% and 75% or about 75%, between 65% or about 65% and 76% or about 76%, between 68% or about 68% and 76% or about 76%, by weight, of the concentrate.

In some embodiments, the amount of the surfactant(s) is between 17% or about 17% and 26% or about 26%, by weight, of the concentrate, for example, between 17% or about 17% and 26% or about 26%, between 18% or about 18% and 26% or about 26, between 16% or about 16% and 18% or about 18%; or 20% or about 20%, or 25% or about 25%, by weight, of the concentrate, or at or about 17, 17.75, 18, 19, 20, 20.2, 21, 22, 23, 24, 25, 25.2 or 26%, by weight, of the concentrate.

Typically, the surfactant(s) in the provided concentrates has an Hydrophilic Lipophilic Balance (HLB) value of between 14 or about 14 and 20 or about 20, for example, at or about 14, 15, 16, 17, 18, 19 or 20, typically between 16 or about 16 and 18 or about 18. Exemplary of the surfactants include, but are not limited to, non-ionic surfactants, such as polyethylene glycol (PEG)-Sorbitan fatty acid esters, for example, polysorbates, including PEG-sorbitan monooleates, such as Polyoxyethylene (20) sorbitan monooleate (also called polysorbate 80), as well as polysorbate 80 analogs, such as polysorbate 80 homologs and polysorbate 80 derivatives.

In one aspect, the surfactant is a polysorbate 80 homolog, such as, for example, a polysorbate 80 homolog that differs from a polysorbate 80 parent compound by the addition or removal of one or more methylene unit(s), e.g., —$(CH_2)_n$—. Exemplary of the polysorbate analogs are other polysorbates having a similar HLB value, such as, for example, polysorbate 20, polysorbate 40 and polysorbate 60.

In some embodiments of the provided liquid nanoemulsion concentrates, the PEG moiety in the PEG-sorbitan fatty acid ester surfactant is selected from among any one or more of methylated PEG (m-PEG), PEG-OH, PEG-NHS, PEG-aldehyde, PEG-SH, PEG-$NH_2$, PEG-$CO_2H$, methylated PEGS and branched PEGs. In some embodiments, the PEG moiety in the surfactant has a molecular weight of between 200 kDa or about 200 kDa to 20,000 kDa or about 20,000 kDa, between 200 kDa or about 200 kDa and 6000 kDa or about 6000 kDa, between 600 kDa or about 600 kDa and 6000 kDa or about 6000 kDa, between 200 kDa or about 200 kDa and 2000 kDa or about 2000 kDa, between 600 kDa or about 600 kDa and 1500 kDa or about 1500 kDa, or between 600 kDa or about 600 kDa and 1000 kDa or about 1000 kDa.

Exemplary of non-polar compounds that can be included in any of the provided concentrates are non-polar active ingredients. Exemplary non-polar active ingredients include, but are not limited to omega-3 fatty acids, omega-6 fatty acids, conjugated fatty acids, Coenzyme Q10 (e.g. ubidecarenone), phytosterols and saw palmetto extracts, such as, for example, fish oil, algae oil, flaxseed oil GLA (e.g. borage oil) and CLA.

Also exemplary of the non-polar active ingredients include, but are not limited to, compounds containing any fat-soluble nutraceutical or pharmaceutical and/or oil, such as, for example, drugs, hormones, vitamins, nutrients, including any and other lipophilic compounds containing essential fatty acids, for example, polyunsaturated fatty acids (PU-FAs), including, for example, omega-3 fatty acids, for example, natural and synthetic omega-3 fatty acids, for example, compounds containing omega-3 polyunsaturated long-chain fatty acids, including Eicosapentaenoic acid (EPA) (20:5ω3); Docosahexaenoic acid (DHA) (22:6ω3); Eicosatetraenoic acid (24:4ω3); Docosapentaenoic acid (DPA, Clupanodonic acid) (22:56ω3); 16:3ω3; 24:5ω3 and/or nisinic acid (24:6ω3), for example, fish oil, algae oil, krill oil, canola oil, flaxseed oil, soybean oil and walnut oil; compounds containing short-chain omega-3 fatty acids, for example, Alpha-Linolenic acid (α-Linolenic acid; ALA) (18:3ω3) (e.g. flaxseed oil) and Stearidonic acid (18:4ω3), esters of an omega-3 fatty acid and glycerol, for example, monoglycerides, diglycerides and triglycerides, esters of omega-3 fatty acid and a primary alcohol, for example, fatty acid methyl esters and fatty acid esters, precursors of omega-3 fatty acid oils, for example, EPA precursor, DHA precursor, derivatives such as polyglycolized derivatives or polyoxyethylene derivatives, oils containing the omega-3 fatty acids, for example, fish oil (marine oil), for example, highly purified fish oil concentrates, perilla oil, krill oil, and algae oil, for example, microalgae oil; compounds containing omega 6 fatty acids, for example, compounds containing Linoleic acid (18:2ω6) (a short-chain fatty acid); Gamma-linolenic acid (GLA) (18:3ω6); Dihomo gamma linolenic acid (DGLA) (20:3ω6); Eicosadienoic acid (20:2ω6); Arachidonic acid (AA) (20:4ω6); Docosadienoic acid (22:2ω6); Adrenic acid (22:4ω6); and/or Docosapentaenoic acid (22:5ω6), for example, borage oil, corn oil, cottonseed oil, grapeseed oil, peanut oil, primrose oil, for example, evening primrose (*Oenothera biennis*) oil, blackcurrant seed oil, hemp seed oil, spirulina extract, safflower oil, sesame oil and soybean oil;

compounds containing other fatty acids, for example, triglycerides, including medium chain triglycerides, polar lipids, for example, ether lipids, phosphoric acid, choline, fatty acids, glycerol, glycolipids, triglycerides, and phospholipids (e.g., phosphatidylcholine (lecithin), phosphatidylethanolamine, and phosphatidylinositol); saw palmetto extract; and ethyl linoleate; and herb oils, for example, garlic oils and scordinin; short-chain saturated fatty acids (4:0-10:0), Lauric acid (12:0), Myristic acid (14:0), Pentadecanoic acid (15:0), Palmitic acid (16:0), Palmitoleic acid (16:1 ω7), Heptadecanoic acid (17:0), Stearic acid (18:0), Oleic acid (18:1 ω9), Arachidic acid (20:0);

compounds containing micronutrients, for example, vitamins, minerals, co-factors, for example, coenzymes, such as coenzyme Q, e.g. Coenzyme Q10 (CoQ10, also called ubiquinone, e.g. ubidecarenone or a reduced form of CoQ10, e.g. ubiquinol), tumeric extract (cucuminoids), saw palmetto lipid extract (saw palmetto oil) echinacea extract, hawthorn berry extract, ginseng extract, lipoic acid (thiotic acid), ascorbyl palmitate, kava extract, St. John's Wort (hypericum, Klamath weed, goat weed), extract of quercitin, dihydrocpiandrosterone, indol-3-carbinol;

compounds containing carotenoids, including hydrocarbons and oxygenated, alcoholic derivatives of hydrocarbons, for example, beta carotene, mixed carotenoids complex, lutein, lycopene, Zeaxanthin, Cryptoxanthin, for example, beta-crytoxanthin, beta carotene, mixed carotenoids complex, astaxanthin, bixin, canthaxanthin, capsanthin, capsorubin, apo-carotenal, beta-12'-apo-carotenal, "Carotene" (mixture of alpha and beta-carotene), gamma carotene, ciolerythrin, zeaxanthin, esters of hydroxyl- or carboxyl-containing members thereof;

compounds containing fat-soluble vitamins, for example, Vitamins A, D, E and K, and corresponding provitamins and vitamin derivatives such as esters with an action resembling that of vitamin A, D, E or K for example; retinol (vitamin A) and pharmaceutically acceptable derivatives thereof, for example, palmitate ester of retinol and other esters of retinol, and calciferol (vitamin D) and its pharmaceutically acceptable derivatives thereof and precursors of vitamin D, d-alpha tocopherol (vitamin E) and derivatives thereof, including pharmaceutical derivatives thereof, for example, Tocotrienols, d-alpha tocopherol acetate and other esters of d-alpha tocopherol, and ascorbyl palmitate, a fat-soluble version of vitamin C;

compounds containing phytochemicals, including phytoestrogens, for example, genistein and daidzein, for example, isoflavones, for example, soy isoflavones, flavonoids, phytoalexins, for example, Resveratrol (3,5,4'-trihydroxystilbene), red clover extract, and phytosterols;

compounds containing lipid-soluble drugs, including natural and synthetic forms of immunosuppressive drugs, such as Cyclosporin, protease inhibitors such as Ritonavir, macrolide antibiotics and oil soluble anesthetics such as Propofol, natural and synthetic forms of steroidal hormones, for example, estrogens, estradiols, progesterone, testosterone, cortisone, phytoestrogens, dehydroepiandrosterone (DHEA), growth hormones and other hormones;

compounds containing oil-soluble acids and alcohols, for example, tartaric acid, lactylic acid, butylated hydroxyanisole, butylated hydroxytoluene, lignin, sterols, polyphenolic compounds, oryzanol, cholesterol, phytosterols, flavonoids, such as, but not limited to, quercetin, reservatol, and diallyl disulfides.

In some embodiments, the non-polar active ingredient includes one or more of polyunsaturated fatty acids, such as compounds including any one or more of omega-3 fatty acids, including Docosahexaenoic acid (DHA), eicosapentaenoic acid (EPA) and alpha-linolenic acid (ALA) (for example, fish oils, krill oils, algae oils and/or flaxseed oils); omega-6 fatty acids, such as gamma-linolenic acid (GLA) (e.g. borage oils); conjugated fatty acids (e.g. conjugated linoleic acid (CLA)); and saw palmetto extracts. In other embodiments, the non-polar active ingredients include compounds containing coenzymes, typically coenzyme Q, for example, Coenzyme Q10, e.g. ubidecarenone, and/or compounds containing phytosterols.

In any of the provided concentrates, the non-polar active ingredient contains EPA, DHA or a combination thereof. In one aspect, the non-polar active ingredient contains DHA, at an amount between 20% or about 20% and 90% or about 90% or between 25% or about 25% and 85% or about 85%; or between 35% or about 35% and 70% or about 70%, or between 25% or about 25% and 40% or about 40%, by weight, of the non-polar active ingredient. In another aspect, the non-polar active ingredient contains EPA, at an amount between 5% or about 5% and 15% or about 15%, between 5% or about 5% and 13% or about 13%, or between 5% or about 5% and 10% or about 10% by weight, of the non-polar active ingredient. In one aspect, the amount of EPA is not more than 10% or about 10%, or not more than 13% or about 13%, by weight, of the non-polar active ingredient. In exemplary embodiments, the non-polar active ingredient is a fish oil or an algae oil.

In one embodiment, the non-polar active ingredient contains ALA, at an amount of at least 50% or about 50%, by weight, of the non-polar active ingredient, such as between 50% or about 50% and 80% or about 80%, or between 65% or about 65% and 75% or about 75%, by weight, of the non-polar active ingredient. Exemplary of such an embodiment is a concentrate containing a flaxseed oil.

In another embodiment, the non-polar active ingredient contains GLA at an amount of at least 22% or about 22%, by weight, of the non-polar active ingredient, for example, in a borage oil.

In some embodiments, the concentrates contain more than one non-polar active ingredient, for example, two or more non-polar active ingredients where the total amount of non-polar active ingredient is between at or about 5% and 10% of the weight of the concentrate, for example, where the combined weight of the non-polar active ingredient and additional non-polar active ingredient(s) is less than at or about 10%, by weight, of the concentrate.

The provided concentrates further can contain one or more additional ingredients. In one embodiment, the concentrate further contains a co-surfactant in an amount sufficient to stabilize the concentrate. In one aspect, the co-surfactant is a phospholipid, such as, but not limited to, a phosphatidylcholine. In one example, the amount of the co-surfactant, e.g. the phospholipid, is between 0.1% or about 0.1% and 1% or about 1%, by weight, of the concentrate.

In another embodiment, the concentrate further contains a preservative, in amount sufficient to preserve the concentrate. Exemplary of the preservatives are natural preservatives, such as benzyl alcohol and preservatives containing benzyl alcohol. In one embodiment, the amount of preservative is between 0.1% or about 0.1% and 1% or about 1%, by weight, of the concentrate, for example, at or about 0.1, 0.2, 0.3, 0.4, 0.5, 0.6, 0.7, 0.8, 0.9 or 1%, by weight of the concentrate. In one example, the amount of benzyl alcohol is between 0.1% or about 0.1% and 1% or about 1%, by weight, of the concentrate, for example, at or about 0.1, 0.2, 0.3, 0.4, 0.5, 0.6, 0.7, 0.8, 0.9 or 1%, by weight of the concentrate.

Also exemplary of additional ingredients in that can be included in the concentrate are one or more solvents. In one aspect, the concentrate contains one or more solvent that dissolves the non-polar active ingredient and differs therefrom, wherein the amount of solvent is sufficient to dissolve the non-polar active ingredient. The solvent typically is an oil. It can be any oil suitable for dissolving the non-polar ingredient. Exemplary of the solvents are Vitamin E oil, flaxseed oil, sunflower oil, any vegetable oil or other oil. In one embodiment, the amount of solvent in the concentrate is between 1% or about 1% and 6% or about 6%, for example, at or about 1, 2, 3, 4, 5, or 6%, by weight, of the concentrate.

Also exemplary of the additional ingredients that can be included in the concentrate are one or more emulsion stabilizers. Typically, the emulsion stabilizer is included in the concentrate at an amount sufficient to stabilize the concentrate. Exemplary of an emulsion stabilizer is a composition containing a blend of gums, such as the Saladizer® brand emulsion stabilizer. In one embodiment, the emulsion stabilizer contains one or more of guar gum, xanthan gum and sodium alginate. In one example, the emulsion stabilizer contains guar gum, xanthan gum and sodium alginate.

Also exemplary of the additional ingredients that can be included in the provided concentrates are one or more flavors. Typically, the flavor(s) is included at an amount sufficient to enhance the taste of the concentrate, the smell of the concentrate, or a combination thereof. Exemplary of the flavors are flavors containing lemon oil and D-limonene, or combination thereof, or any other known flavors, such as flavors described herein.

Also exemplary of the additional ingredients that can be included in the provided concentrates are one or more pH adjusters. Typically, the pH adjuster contains an acid or a base at an amount sufficient to affect the pH of the concentrate. Exemplary of suitable pH adjusters are citric acid and phosphoric acid.

In some embodiments, the concentrate is formulated based on the properties of resulting dilution compositions generated by diluting the concentrate in an aqueous liquid. Typically, the concentrate is formed so that it can be diluted in aqueous medium to produce a liquid dilution composition having one, more than one, all, or any combination of, of the following properties:

In one embodiment, the concentrate is formulated such that: dilution of at least 0.5 g or about 0.5 g, at least 1 g or about 1 g, at least 2 g or about 2 g, at least 5 g or about 5 g, or at least 10 g or about 10 g of the concentrate into at or about 8 fluid ounces (0.236588 liters) of an aqueous medium; or dilution of the concentrate in an aqueous medium, at a dilution of not more than 1:10 or about 1:10, not more than 1:25 or about 1:25, not more than 1:50 or about 1:50, not more than 1:100 or about 1:100, not more than 1:250 or about 1:250, or not more than 1:500 or about 1:500, yields a liquid dilution composition having a particle size of less than 500 nm or less than about 500 nm, less than 300 or about 300 nm or less than 200 nm or less than about 200 nm, on average or at the most.

In one embodiment, the liquid dilution composition formed by dilution of the concentrate into aqueous medium has a particle size of less than 500 nm or less than about 500 nm, less than 300 or less than about 300 nm, or less than 200 nm or less than about 200 nm, on average or at the most, and contains at least 25 mg or about 25 mg, at least 35 mg or about 35 mg, at least 50 mg or about 50 mg, or at least 100 mg or about 100 mg, at least 250 mg or about 250 mg, or at least 500 mg or about 500 mg of the non-polar active ingredient per 8 fluid ounces of the liquid dilution composition.

In some examples of these embodiments, the liquid dilution composition formed by dilution of the concentrate contains a particle size of less than 100 nm or about 100 nm, less than 50 nm or about 50 nm, less than 25 nm or about 25 nm, less than 15 nm or about 15 nm or less than 10 nm or about 10 nm, on average or at the most.

In another embodiment, the concentrate is formulated such that dilution of at least 0.5 g or about 0.5 g, at least 1 g or about 1 g, at least 2 g or about 2 g, at least 5 g or about 5 g, or at least 10 g or about 10 g of the concentrate into 8 or about 8 fluid ounces of an aqueous medium; or dilution of the concentrate in an aqueous medium, at a dilution not more than 1:10 or about 1:10, not more than 1:25 or about 1:25, not more than 1:50 or about 1:50, not more than 1:100 or about 1:100, not more than 1:250 or about 1:250, or not more than 1:500 or about 1:500, yields a liquid dilution composition having a Nephelometric Turbidity Units (NTU) value of less than 500 or about 500, less than 300 or about 300, or less than 200 or about 200. In one aspect, the NTU value of the resulting dilution composition is less than 100 or about 100, less than 50 or about 50, less than 30 or about 30, less than 25 or about 25, or less than 10 or about 10.

In another embodiment, the liquid dilution composition formed by dilution of the concentrate into aqueous medium has an NTU value of less than 500 or about 500, less than 300 or about 300, or less than 200 or about 200 and contains at least 25 mg or about 25 mg, at least 35 mg or about 35 mg, at least 50 mg or about 50 mg or at least 100 mg or about 100 mg, at least 250 mg or about 250 mg, or at least 500 mg or about 500 mg of the non-polar active ingredient per 8 fluid ounces of the liquid dilution composition.

In some aspects of these embodiments, the NTU value is less than 100 or about 100, less than 50 or about 50, less than 30 or about 30, less than 25 or about 25, or less than 10 or about 10.

In another embodiment, the concentrate is formulated such that dilution of at least 0.5 g or about 0.5 g, at least 1 g or about 1 g, at least 2 g or about 2 g, at least 5 g or about 5 g, or at least 10 g or about 10 g of the concentrate into 8 or about 8 fluid ounces of an aqueous medium; or dilution of the concentrate in an aqueous medium, at a dilution not more than 1:10 or about 1:10, not more than 1:25 or about 1:25, not more than 1:50 or about 1:50, not more than 1:100 or about 1:100, not more than 1:250 or about 1:250, or not more than 1:500 or about 1:500, yields a liquid dilution composition that does not contain visible particles, does not contain visible crystals, does not exhibit ringing and/or does not exhibit phase separation; and/or remains free from visible particles, visible crystals, ringing and/or phase separation when stored at room temperature (e.g. 25° C. or about 25° C.), or at a refrigerated temperature (e.g. 0-10° C. or about 0-10° C., e.g. at or about 4° C.), or at a frozen temperature (e.g. −20° C. or about −20° C.), wherein the storage is for at least one day, at least one week, at least thirty days, or at least one year.

In one embodiment, the concentrate is formulated such that dilution of at least 0.5 g or about 0.5 g, at least 1 g or about 1 g, at least 2 g or about 2 g, at least 5 g or about 5 g, or at least 10 g or about 10 g of the concentrate into 8 or about 8 fluid ounces of a beverage; or dilution at not more than 1:10 or about 1:10, not more than 1:25 or about 1:25, not more than 1:50 or about 1:50, not more than 1:100 or about 1:100, not more than 1:250 or about 1:250, or not more than 1:500 or about 1:500 into a beverage, yields a liquid dilution composition that is at least as clear as, or substantially as clear as, the beverage, and/or remains as clear as, or substantially as clear as, the beverage when stored at room temperature (e.g. 25° C. or about 25° C.), or at a refrigerated temperature (e.g. 0-10° C. or about 0-10° C., e.g. at or about 4° C.), or at a frozen temperature (e.g. −20° C. or about −20° C.), wherein the storage is for at least one day, at least one week, at least thirty days, or at least one year.

Also provided are liquid dilution compositions, which contain the concentrates diluted in an aqueous medium. Exemplary of the aqueous medium are beverages, such as, for example, water, juice, soda, tea, coffee, sports drinks, nutritional beverages, energy drinks, milk, and other beverages. The provided liquid dilution compositions are liquid dilution compositions containing any one or more of the provided concentrates. Typically, the provided liquid dilution compositions are compositions containing the concentrate(s) and having any one or more of the properties of the desired liquid dilution compositions described above.

For example, in one embodiment, the provided liquid dilution composition contains a particle size less than 500 or about 500, less than 300 or about 300, less than 200 or about 200 nm, less than 100 or about 100 nm, less than 50 or about 50 nm or less than 25 or about 25 nm on the average or at the most. In another embodiment, the liquid dilution composition has an NTU value less than 500 or about 500, less than 300 or about 300, less than 200 or about 200, less than 100 or about 100, less than 50 or about 50, less than 25 or about 25, or less than 10 or about 10. In one example, the liquid dilution composition does not contain visible particles, does not contain visible crystals, does not exhibit ringing and/or does not exhibit phase separation; and/or remains free from (or does not exhibit) visible particles, visible crystals, ringing and/or phase separation when stored at room temperature (e.g. 25° C. or about 25° C.), or at a refrigerated temperature (e.g. 0-10° C. or about 0-10° C., e.g. at or about 4° C.), or at a frozen temperature (e.g. −20° C. or about −20° C.), wherein the storage is for at least one day, at least one week, at least thirty days, or at least one year.

In one example, the aqueous medium contained in the liquid dilution composition is a beverage, such as, for example, water, soda, milk, tea, coffee, juice, energy drink or a sports or nutrition beverage. In one aspect, the liquid dilution composition is as clear or about as clear as the beverage prior to addition of the concentrate, and/or remains as clear or about as clear as the beverage when stored at room temperature (e.g. 25° C. or about 25° C.), or at a refrigerated temperature (e.g. 0-10° C. or about 0-10° C., e.g. at or about 4° C.), or at a frozen temperature (e.g. −20° C. or about −20° C.), wherein the storage is for at least one day, at least one week, at least thirty days, or at least one year.

In one embodiment, the dilution factor at which the concentrate is diluted in the aqueous medium is not more than 1:10 or about 1:10, not more than 1:25 or about 1:25, not more than 1:50 or about 1:50, not more than 1:100 or about 1:100, not more than 1:250 or about 1:250, or not more than 1:500 or about 1:500. In another embodiment, the concentrate is diluted in the aqueous medium to form the liquid dilution composition at 0.5 g or about 0.5 g, at least 1 g or about 1 g, at least 2 g or about 2 g, at least 5 g or about 5 g, or at least 10 g or about 10 g of the concentrate into 8 or about 8 fluid ounces of the aqueous medium. In another embodiment, the liquid dilution composition contains at least 25 mg or about 25 mg, at least 35 mg or about 35 mg, at least 50 mg or about 50 mg or at least 100 mg or about 100 mg, at least 250 mg or about 250 mg, or at least 500 mg or about 500 mg of the non-polar active ingredient per 8 fluid ounces of the liquid dilution composition.

In one embodiment, the liquid dilution composition does not contain visible particles; and/or remains free from visible particles when stored at room temperature, or at a refrigerated temperature, or at a frozen temperature, wherein the storage is for at least one day, at least one week, at least thirty days, or at least one year; and/or does not contain visible crystals, for example, remains free from visible crystals when stored at room temperature, or at refrigerated temperature, or at a frozen temperature, wherein the storage is for at least one day, at least one week, at least thirty days, or at least one year; and/or does not exhibit ringing, for example, remains free from ringing when stored at room temperature, at a refrigerated temperature, or at a frozen temperature, wherein the storage is for at least one day, at least one week, at least thirty days, or at least one year; or does not exhibit phase separation, for example, does not exhibit phase separation when stored at room temperature, refrigerated temperature or frozen temperature, wherein the storage is for at least one day, at least one week, at least thirty days, or at least one year.

Also provided are methods for making the concentrates and methods for making the liquid dilution compositions. Generally, the methods for making the concentrates are carried out by generating, separately, an oil phase and a water phase, and mixing the two phases, typically by emulsification, to form the concentrate, e.g. liquid nanoemulsion concentrate. Typically, the oil phase ingredients include the non-polar compound (e.g. non-polar active ingredient) of the concentrate and the surfactant, while the water phase ingredients include water at an amount within the appropriate range for the provided concentrates.

The amounts of the surfactant(s), non-polar active ingredient(s) and water are selected based on the appropriate concentration ranges of these ingredients in the resulting concentrate. For example, the non-polar active ingredient is included at an amount that is between 5% or about 5% and 10% or about 10%, by weight, of the final concentrate; the surfactant is included at an amount that is between 16% or about 16% and 30% or about 30%, by weight, of the final concentrate; and water is included at an amount that is between 60% or about 60% and 80% or about 80%, by weight, of the final concentrate, as described above.

In one example, the oil phase ingredients further include at least one solvent. In one example, the concentrate is made with first and second oil phase ingredients and the first oil phase ingredients include the non-polar active ingredient and the solvent. In one example, the solvent contains an oil, other than the non-polar active ingredient, such as, for example, Vitamin E, flaxseed oil and/or safflower oil.

In one example, the oil phase ingredients and/or the water phase ingredients further comprise a co-surfactant, at an amount sufficient to stabilize the concentrate, such as a phospholipid, e.g. phosphatidylcholine. In one example, the amount of phospholipid is between 0.1% or about 0.1% and 1% or about 1%, by weight, of the concentrate. In another example, the oil phase ingredients and/or the water phase ingredients further contain at least one preservative in amount sufficient to preserve the concentrate, such as, for example, a preservative containing benzyl alcohol. In one example, the amount of preservative and/or the benzyl alcohol is between 0.1% or about 0.1% and 1% or about 1%, by weight, of the concentrate.

In another example, the oil phase ingredients and/or the water phase ingredients further comprise an emulsion stabilizer, at an amount sufficient to stabilize the concentrate, such as an emulsion stabilizer containing a blend of gums, such as any one or more of guar gum, xanthan gum and sodium alginate.

In an exemplary provided method for making the concentrate, an oil phase is generated by mixing oil phase ingredients (e.g. oil phase ingredients containing a non-polar active ingredient and a surfactant of the provided concentrate, such as a surfactant that is a polysorbate 80 or analog thereof) in a first vessel and heating the oil phase ingredients; a water phase is generated by mixing one or more water phase ingredients in a second vessel and heating the water phase ingredients; and the oil and water phases are emulsified to generate the concentrate.

In another exemplary provided method, an oil phase is generated by mixing one or more first oil phase ingredients in a first vessel and heating the first oil phase ingredients at least until the first oil phase ingredients dissolve; then adding one or more additional oil phase ingredients to the first vessel; and mixing and heating the first and the additional oil phase ingredients; a water phase is generated by mixing one or more water phase ingredients in a second vessel and heating the water phase ingredient(s); and the water and oil phases are emulsified, to generate the concentrate.

The heating and mixing of the water and oil phases can be carried out simultaneously or sequentially, in any order.

In any of the provided methods for making the concentrates, the mixing steps (e.g. mixing the oil and/or water phases) can be carried out with a standard mixer, such as any of the standard mixers listed herein. In any of the provided methods, the heating can be carried out using one or more heating apparatuses, such as, for example, a hot plate, a water jacket, or any of the heating apparatuses listed herein. In one example, the oil phase ingredients are heated with a first heating apparatus and the water phase ingredients are heated with a second heating apparatus. In one example, heating involves heating the ingredients to 60° C. or about 60° C. In one example, the oil phase and/or water phase ingredients are heated to between about between 45° C. or about 45° C. and 85° C. or about 85° C., for example, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85° C.

In any of the provided methods, the emulsifying can be carried out using a homogenizer, such as any homogenizer described herein. In one example, the emulsifying is performed at between 850 or about 850 rpm and 1200 or about 1200 rpm. In another example, the emulsifying is performed at a speed lower then 850 rpm, such as, for example, between 25 or about 25 rpm and 50 rpm or about 50 rpm, for example at or about 30 rpm.

In some embodiments, the methods further include rapidly cooling the forming nanoemulsion during the emulsifying step. In some examples, rapid cooling results in cooling of the forming emulsion to between 25° C. or about 25° C. and 35° C. or about 35° C. In one example, the cooling of the nanoemulsion results in less than at or about 60 minutes. Exemplary of the means for performing the rapid cooling include repeatedly passing the phases through a cooling apparatus attached to a vessel.

The provided methods further can include adding one or more flavors (e.g. lemon oil, D-limonene) and/or one or more pH adjusters (e.g. citric acid, phosphoric acid) to the concentrate, for example, after emulsifying the oil and water phases. The pH typically is measured simultaneously with, before and/or after addition of the pH adjuster, and the amount of pH adjuster is determined by the pH of the concentrate. Typically, the pH adjuster comprises an acid or a base at an amount sufficient to affect the pH of the concentrate.

In one example of the methods, the ingredients are added to the vessel(s) simultaneously or sequentially, in any order. In another example, the ingredients (e.g. the oil phase and/or water phase ingredients) are added to the vessels in a particular order, such as a specific order provided herein. In one embodiment, where the water phase ingredients contain water and an emulsion stabilizer, the water phase ingredients are added sequentially, in the following order: 1) water; 2) emulsion stabilizer. In another embodiment, where the oil phase ingredients contain the surfactant, the non-polar compound and a preservative, the oil phase ingredients are added sequentially, in the following order: 1) surfactant; 2) preservative; 3) non-polar compound. In another embodiment, where the oil phase ingredients contain the surfactant, the non-polar compound, a preservative and an emulsion stabilizer, the oil phase ingredients are added to the oil phase vessel sequentially, in the following order: 1) surfactant; 2) preservative; 3) non-polar compound; and 4) emulsion stabilizer. In another embodiment, where the oil phase ingredients contain the surfactant, the non-polar compound, a preservative, a solvent and an emulsion stabilizer, the oil phase ingredients are added to the oil phase vessel sequentially, in the following order: 1) surfactant; 2) preservative; 3) solvent; 4) non-polar compound; and 5) emulsion stabilizer. In another embodiment, where the oil phase ingredients contain the surfactant, the non-polar compound, a preservative, a solvent, a co-surfactant and an emulsion stabilizer, the oil phase ingredients are added to the oil phase vessel sequentially, in the following order: 1) surfactant; 2) preservative; 3) solvent; 4) co-surfactant; 5) non-polar compound; and 6) emulsion stabilizer.

Any of the provided methods for producing the concentrates can be used to make any of the provided concentrates, as described herein.

Also provided are methods for producing the provided liquid dilution compositions containing the concentrates, such as beverages containing the concentrates. These methods include methods for providing oil-based additives, for example, in a food or beverage. These methods include adding any of the provided concentrates, e.g. liquid nanoemulsion concentrates, to an aqueous medium, such as a beverage. Typically, the concentrate is added to the medium, e.g. beverage, such that the medium contains an effective amount of the additive (e.g. the non-polar active ingredient).

The effective amount of the additive, such as the non-polar active ingredient is the quantity and/or concentration of the additive necessary for preventing, curing, ameliorating, arresting or partially arresting a symptom of a disease or disorder, or the quantity and/or concentration desired by an individual for intake, such as daily intake, and/or nutritional supplementation, for example, an amount sufficient to enhance the nutritional, pharmaceutical, nutraceutical, health or energy property of a food, beverage, or other consumable. In some examples, the concentrate is added to the aqueous medium such that the resulting liquid dilution composition contains an effective amount of a particular non-polar compound, for example, a particular amount per volume or weight of the composition, such as, for example, at least 25 mg or about 25 mg, at least 35 mg or about 35 mg, at least 50 mg or about 50 mg or at least 100 mg or about 100 mg, at least 250 mg or about 250 mg, or at least 500 mg or about 500 mg of the non-polar active ingredient per 8 fluid ounces of the liquid dilution composition.

In one example, an effective amount is a concentration or amount of the liquid nanoemulsion concentrate where at least 25 mg or about 25 mg, typically at least 35 mg, for example, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000 mg, or more, of the non-polar active ingredient, is contained in at least 8 fluid ounces of the aqueous medium.

U.S. Provisional Application Ser. No. 61/070,381, filed Mar. 20, 2008, entitled "COMPOSITIONS CONTAINING NON-POLAR COMPOUNDS;" and U.S. Provisional Application Ser. No. 61/132,424, filed Jun. 16, 2008, entitled "COMPOSITIONS CONTAINING NON-POLAR COMPOUNDS," each to Philip Bromley, disclose, for example, compositions containing non-polar compounds and surfactants such as PEG-derivatives of Vitamin E, such as Tocopherol Polyethylene glycol succinate (TPGS) and TPGS analogs, including TPGS homologs, and methods for making the compositions. The subject matter of each of the above-noted provisional applications is incorporated by reference in its entirety. Any of the compositions disclosed in the above-noted applications can be adapted to make the provided compositions, for example, by replacing the surfactant(s) in the compositions with surfactant(s) such as polysorbate 80 and polysorbate 80 analogs, including polysorbate 60, polysorbate 40 and polysorbate 20 and other surfactants having similar HLB values, to make the provided compositions.

BRIEF DESCRIPTION OF THE DRAWINGS

FIG. 1 sets forth an exemplary scaled-up process 100 of the provided methods for making the liquid nanoemulsion concentrates. This process is exemplary and variations can be used. In this example, water 101 is used as the polar solvent and the water is first purified by passage through the following purifiers, sequentially, in the following order: a carbon filter 105, ion exchange equipment 106, reverse osmosis equipment 107, a 100 micron end-point filter 108, and a 50 micron point-of-use filter 109. After purification, the water is added, with the other water phase ingredients, to a water phase tank 103. The water phase ingredient(s) then are mixed using a standard mixer 111 attached to the tank, for example, mounted on the top of the tank. A heating apparatus (typically the water jacket on the water phase tank) is used to heat the water phase ingredients during water phase generation, typically to low heat (e.g. 60° C.). To generate the oil phase, the oil phase ingredient(s) are weighed/measured and added to an oil phase tank 102. The oil phase ingredients are mixed using a standard mixer 111 attached to the oil phase tank, for example, mounted on the tank. A heating apparatus (typically the water jacket on the oil phase tank) is used to heat the oil phase ingredients during water phase generation, typically to low heat (e.g. 60° C.). Once the oil and water phases reach 60° C., and after oil phase components have dissolved, the oil and water phases are combined by transferring the oil phase to the water phase vessel, via transfer means 112. For this process, a homogenizer 110 mounted on the water phase tank, is turned on to homogenize the mixture. The ball valves then are opened and the transfer pump turned on, thereby effecting transfer of the oil phase liquid to the water phase tank via the transfer hose(s). As the phases are combined, the mixture is homogenized by continued mixing with the homogenizer 110. The homogenizer can be adjusted, for example, by adjusting the baffle plate on the homogenizer to achieve and maintain an emulsion, for example, by moving the baffle plate further into the forming emulsion and/or further out of the forming emulsion. During the emulsifying step, the forming emulsion is cooled, typically rapidly cooled, by repeatedly passing the forming emulsion through a recirculating cooler 115 (e.g. Model No. OC-1000 RO, sold by Turmoil, West Swanzey, N.H.), which is attached to the water phase tank. The emulsion is transferred, via transfer means 112 to a holding/packaging tank 104, where additional ingredients can be added and/or the mixture can be evaluated. The additional ingredients are mixed into the concentrate using a standard mixer 111. An end-product filter 113 is used to filter the concentrate before use.

BRIEF DESCRIPTION OF THE DRAWINGS

FIG. 1 shows an exemplary scaled-up process for making the liquid concentrate.

DETAILED DESCRIPTION

Outline
A. Definitions
B. Compositions Containing Non-Polar Compounds
  1. Liquid Nanoemulsion Concentrates Containing the Non-Polar Compounds
    a. Formulating the Liquid Concentrates
      i. Common Ingredients and Typical Concentration Ranges
      ii. Evaluation of the Initial Concentrate
        (1) Clarity
          (a) Empirical Evaluation
          (b) Particle Size
          (c) Turbidity Measurement
      iii. Selecting a Formulation and Modifying Formulations
    b. Non-Polar Compounds
      i. Polyunsaturated Fatty Acid (PUFA)-Containing Active Ingredients
        (1) Omega-3 Fatty Acid Compounds
          (a) DHA/EPA
          (b) Fish Oils
          (c) Algae Oil
          (d) Flax Seed Oil—Omega 3 (ALA)
        (2) Omega-6 Compounds
          (a) Borage Oil (Gamma-Linolenic Acid (GLA))
        (3) Saw Palmetto Extract
        (4) Conjugated Linoleic Acid (CLA)
      ii. Coenzyme Q Active Ingredients
        (1) Coenzyme Q10
      iii. Phytosterol-Containing Active Ingredients
    c. Surfactants
      i. Concentration of the Surfactant
      ii. Hydrophilic Lipophilic Balance (HLB)
        (1) Co-Surfactants (Emulsifiers)
          (a) Phospholipids
      iii. Water
      iv. Preservatives and Sterilizers
      v. Emulsion Stabilizers (Co-Emulsifier)
      vi. Solvents
      vii. Flavors
      viii. pH Adjusters
  2. Powder Forms of the Compositions
  3. Liquid Dilution Compositions Containing the Diluted Concentrates
    a. Clarity
      i. Clarity Determined by Empirical Evaluation
      ii. Clarity Determined by Particle Size or Number of Particles
      iii. Turbidity
    b. Stability
    c. Desirable Characteristics for Human Consumption
    d. Safety
    e. Oral Bioavailability
C. Methods for Making Liquid Nanoemulsion Concentrates Containing Non-Polar Compounds
  1. Equipment for Making the Concentrates
    a. Scales
    b. Purifiers, Including Filters
    c. Vessels for Mixing the Ingredients
    d. Mixers
    e. Heating Apparatuses
    f. Cooling Apparatuses
    g. Transfer Means
    h. Evaluation Equipment
  2. General Methods for Making the Liquid Nanoemulsion Concentrates
    a. Generating the Water Phase
      i. Water Phase Ingredients
    b. Generating the Oil Phase
      i. Oil Phase Ingredients
    c. Combining and Emulsifying the Oil Phase and the Water Phase
      i. Combining the Oil and Water Phases
      ii. Emulsifying the Oil and Water Phases
      iii. Cooling
    d. Additional Steps
      i. Additional Ingredients
      ii. Evaluation of the Concentrate
      iii. Filtering the Concentrate
  3. Bench-Top Process
  4. Scaled-Up Manufacturing Process
    a. Water Purification
    b. Generation of the Water Phase and Oil Phase:
    c. Combining and Emulsifying the Phases
    d. Cooling
    e. Additional Steps
D. Methods for Making the Liquid Dilution Compositions Containing the Diluted Concentrates
  1. Dilutions
  2. Analyzing the Aqueous Liquid Dilution Compositions Containing the Liquid Concentrates
    a. Clarity/Turbidity
      i. Empirical Evaluation
      ii. Particle Size
      iii. Turbidity Measurement
E. Examples

A. DEFINITIONS

Unless defined otherwise, all technical and scientific terms used herein have the same meaning as is commonly understood by one of skill in the art to which the invention(s) belong. All patents, patent applications, published applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, colloid refers to a mixture containing two phases, a dispersed phase and a continuous phase, the dispersed phase containing particles (droplets) distributed throughout the continuous phase. Colloidal mixtures include aerosols, foams and dispersions, for example, emulsions, for example, nanoemulsions. A liquid colloid, for example, a nanoemulsion, can have a similar appearance, for example, clarity, to a solution, in which there is no dispersed phase.

As used herein, emulsion refers to a colloidal dispersion of two immiscible liquids, for example, an oil and water (or other aqueous liquid, e.g., a polar solvent), one of which is part of a continuous phase and the other of which is part of a dispersed phase. The provided compositions include emulsions, typically oil-in-water nanoemulsions (which include any oil soluble phase dispersed in any aqueous phase, also called the water phase), in which the oil phase is the dispersed phase and the water phase is the continuous phase. Emulsions typically are stabilized by one or more surfactants and/or co-surfactants and/or emulsion stabilizers. Surfactants form an interfacial film between the oil and water phase of the emulsion, providing stability. Typically, the nanoemulsions of the provided compositions contain micelles, containing one or more surfactant surrounding a non-polar active ingredient, which are dispersed in the water phase. Exemplary of the provided emulsions are the provided liquid nanoemulsion concentrates and liquid dilution compositions, which are made by diluting the concentrates, typically in an aqueous medium.

As used herein, a nanoemulsion is an emulsion in which the dispersed droplets, for example, the micelles, have a diameter (particle size) less than 1000 nm or less than about 1000 nm, typically, less than 500 nm or less than about 500 nm, typically less than 300 nm or about 300 nm, for example, less than 250 nm or about 250 nm, for example, less than 200 nm or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. Exemplary of nanoemulsions are the provided liquid nanoemulsion concentrates and the liquid dilution compositions, for example, the aqueous liquid dilution compositions containing the diluted concentrates.

As used herein, "surfactant" and "surface active agent" refer synonymously to refer to synthetic and naturally occurring amphiphilic molecules, for example, molecules having hydrophobic portion(s) and hydrophilic portion(s). In one example, the hydrophobic portion of the surfactant molecule is a hydrophobic tail and the hydrophilic portion of the surfactant is a hydrophilic head. Due to their amphiphilic (amphipathic) nature, surfactants and co-surfactants typically can reduce the surface tension between two immiscible liquids, for example, the oil and water phases in an emulsion, for example, a nanoemulsion, thus stabilizing the emulsion. Different surfactants can characterized based on their relative hydrophobicity and/or hydrophilicity. For example, relatively lipophilic surfactants are more soluble in fats, oils and waxes, typically having HLB values less than 10 or about 10, while relatively hydrophilic surfactants are more soluble in aqueous compositions, for example, water, and typically have HLB values greater than 10 or about 10. Relatively amphiphilic surfactants are soluble in oil and water based liquids and typically have HLB values close to 10 or about 10.

Surfactants include, for example, soaps, detergents, lipids, emulsifiers, dispersing agents and wetting agents, molecules that emulsify liquids, for example, by forming an emulsion in an aqueous medium or aqueous liquid dilution composition, for example, forming a colloidal dispersion of two immiscible liquids in the form of droplets, for example, an emulsion such as a microemulsion; and compounds that form various macromolecular structures, for example, aggregates, in liquids, for example, micelles, lipid bilayer structures, including liposomes, and inverse micelles.

Typically, the surfactants used in the provided compositions have an HLB value between 14 or about 14 and 20 or about 20, such as, for example, 14 or about 14, 15 or about 15, 16 or about 16, 17 or about 17, 18 or about 18, 19 or about 19, or 20 or about 20. Exemplary of the surfactants include, but are not limited to, non-ionic surfactants, such as polyethylene glycol (PEG)-Sorbitan fatty acid esters, for example, PEG-sorbitan monooleates, such as Polyoxyethylene (20) sorbitan monooleate (also called polysorbate 80), as well as polysorbate 80 analogs, such as polysorbate 80 homologs and polysorbate 80 derivatives. Exemplary polysorbate 80 analog surfactants are polysorbate 40 (polyoxyethylene (20) sorbitan monopalmitate) and polysorbate 60 (polyoxyethylene (20) sorbitan monostearate).

In one aspect, the surfactant is a polysorbate 80 homolog, such as, for example, a polysorbate 80 homolog that differs from a polysorbate 80 parent compound by the addition or removal of one or more methylene unit(s), e.g., $-(CH_2)_n-$.

Other known surfactants having HLB values between 14 or about 14 and 20 or about 20, typically between 16 or about 16 and 18 or about 18, also can be suitable. For example, surfactants having similar properties to polysorbate 80 also can be used, such as, for example, the polysorbate 80 analogs having similar HLB values, such as polysorbate 20, polysorbate 40 (polyoxyethylene (20) sorbitan monopalmitate) and polysorbate 60 (polyoxyethylene (20) sorbitan monostearate). Typically, the surfactant is a natural surfactant, for example, a surfactant that is G.R.A.S. (generally recognized as safe) by the FDA and/or Kosher certified.

As used herein, analog refers to a chemical compound that is structurally similar to another compound (referred to as a parent compound), but differs slightly in composition, for example, by the variation, addition or removal of an atom, one or more units (e.g., methylene unit(s), $-(CH_2)_n-$) or one or more functional groups. The analog can have different chemical or physical properties than the original compound and/or can have improved biological and/or chemical activity. Alternatively, the analog can have similar or identical chemical or physical properties compared with the original compound and/or can have similar or identical biological and/or chemical activity. For example, the analog can be more hydrophilic or it may have altered reactivity as compared to the parent compound. The analog may mimic the chemical and/or biologically activity of the parent compound (i.e., it may have similar or identical activity), or, in some cases, may have increased or decreased activity. The analog may be a naturally or non-naturally occurring (e.g. synthetic) variant of the original compound. Other types of analogs include isomers, such as, but not limited to enantiomers, diastereomers and other types of chiral variants of a compound, as well as structural isomers. The analog may be a branched or cyclic variant of a linear compound. For example, a linear compound may have an analog that is branched or otherwise substituted to impart certain desirable properties (e.g., improve hydrophilicity or bioavailability). Exemplary of the analogs used in the provided compositions and methods are polysorbate 80 analogs (e.g. polysorbate 60, polysorbate 20 and polysorbate 40), which typically are used as surfactants, for example, in place of the polysorbate 80 parent compound in any of the provided compositions.

As used herein, homolog refers to an analog that differs from the parent compound only by the presence or absence of a simple unit, such as a methylene unit, or some multiple of such units, e.g., $-(CH_2)_n-$. Typically, a homolog has similar chemical and physical properties as the parent compound.

Exemplary of the homologs used in the provided compositions and methods are polysorbate 80 homologs.

As used herein, Hydrophilic Lipophilic Balance, or HLB, refers to a value that is used to index and describe a surfactant according to its relative hydrophobicity/hydrophilicity, relative to other surfactants. A surfactant's HLB value is an indication of the molecular balance of the hydrophobic and hydrophilic portions of the surfactant, which is an amphipathic molecule. Each surfactant and mixture of surfactants (and/or co-surfactants) has an HLB value that is a numerical representation of the relative weight percent of hydrophobic and hydrophilic portions of the surfactant molecule(s). HLB values are derived from a semi-empirical formula. The relative weight percentages of the hydrophobic and hydrophilic groups are indicative of surfactant properties, including the molecular structure, for example, the types of aggregates the surfactant will form and the solubility of the surfactant. See, for example, Griffin, W. C. *J. Soc. Cos. Chem.* 1:311 (1949).

Surfactant HLB values range from 1-45, while the range for non-ionic surfactants typically is from 1-20. The more lipophilic a surfactant is, the lower its HLB value. Conversely, the more hydrophilic a surfactant is, the higher its HLB value. Lipophilic surfactants have greater solubility in oil and lipophilic substances, while hydrophilic surfactants dissolve more easily in aqueous media. In general, surfactants with HLB values greater than 10 or greater than about 10 are called "hydrophilic surfactants," while surfactants having HLB values less than 10 or less than about 10 are referred to as "hydrophobic surfactants." HLB values have been determined and are available for a plurality of surfactants (e.g. see U.S. Pat. No. 6,267,985). It should be appreciated that HLB values for a given surfactant or co-surfactant can vary, depending upon the empirical method used to determine the value. Thus, HLB values of surfactants and co-surfactants provide a rough guide for formulating compositions based on relative hydrophobicity/hydrophilicity. For example, a surfactant typically is selected from among surfactants having HLB values within a particular range of the surfactant or co-surfactant, that can be used to guide formulations. Table 1 lists HLB values of exemplary surfactants and co-surfactants.

TABLE 1

HLB Values of Exemplary Surfactants and Co-Surfactants

| Surfactant/co-surfactant | HLB | Surfactant/co-surfactant | HLB |
|---|---|---|---|
| PEG-2 Hydrogenated Castor Oil | 1.7 | PEG-10 oleyl ether | 12.4 |
| Sorbitan Trioleate | 1.8 | PEG-8 isooctylphenyl ether | 12.4 |
| Sorbitan Tristearate | 2.1 | PEG-10 stearyl ether | 12.4 |
| Glyceryl Stearate | 3.5 | PEG-35 Castor Oil | 12.5 |
| Sorbitan Sesquioleate | 3.7 | PEG-10 cetyl ether | 12.9 |
| Labrafil | 4 | Nonoxynol-9 | 12.9 |
| Sorbitan Oleate | 4.3 | PEG-40 Castor Oil | 13 |
| Sorbitan monostearate | 4.7 | PEG-10 isooctylphenyl ether | 13.5 |
| PEG-2 oleyl ether | 4.9 | PEG-40 Hydrogenated Castor Oil | 14 |
| PEG-2 stearyl ether | 4.9 | Labrasol | 14 |
| PEG-7 Hydrogenated Castor Oil | 5 | Nonoxynol-15 | 14.2 |
| PEG-2 cetyl ether | 5.3 | PEG-12 tridecyl ether | 14.5 |
| PEG-4 Sorbitan Stearate | 5.5 | PEG-18 tridecyl ether | 14.5 |
| PEG-2 Sorbitan Isostearate | 6 | Polysorbate 60 | 14.9 |
| Sorbitan Palmitate | 6.7 | Polysorbate 80 | 15 |
| Triton SP-135 | 8 | PEG-20 Glyceryl Stearate | 15 |
| Sorbitan monolaurate | 8.6 | PEG-20 Stearate | 15 |
| PEG-40 Sorbitan Peroleate | 9.5 | PEG-20 stearyl ether | 15.3 |
| PEG-4 lauryl ether | 9.7 | PEG-20 oleyl ether | 15.3 |

TABLE 1-continued

HLB Values of Exemplary Surfactants and Co-Surfactants

| Surfactant/co-surfactant | HLB | Surfactant/co-surfactant | HLB |
|---|---|---|---|
| Polysorbate 81 | 10 | Polysorbate 40 | 15.6 |
| PEG-40 Sorbitan Hexaoleate | 10 | PEG20 cetyl ether | 15.7 |
| PEG-40 Sorbitan Perisostearate | 10 | PEG(20) hexadecyl ether | 15.7 |
| PEG-10 Olive Glycerides | 10 | PEG-60 Hydrogenated Castor Oil | 16 |
| PEG sorbitol hexaoleate | 10.2 | PEG-30 Stearate | 16.5 |
| Polysorbate 65 | 10.5 | Polysorbate 20 | 16.7 |
| PEG-25 Hydrogenated Castor Oil | 10.8 | PEG-75 Lanolin | 16.7 |
| Polysorbate 85 | 11 | PEG23 lauryl ether | 16.9 |
| PEG-7 Glyceryl Cocoate | 11 | PEG-40 Stearate | 17.3 |
| PEG-8 Stearate | 11.1 | PEG-50 Stearate | 17.7 |
| PEG sorbitan tetraoleate | 11.4 | PEG40 isooctylphenyl ether | 17.9 |
| PEG-15 Glyceryl Isostearate | 12 | PEG-100 Stearate | 18.8 |
| PEG-35 Almond Glycerides | 12 | Pluronic F68 | 29 |
| Tocopherol polyethylene glycol succinate (TPGS) | 16-18 | Phosphatidylcholine | 7.6 |

The surfactants and HLB values set forth in Table 1 are exemplary. Any known surfactant or co-surfactant can be used with the provided compositions (e.g. see U.S. Pat. No. 6,267,985). The surfactant(s) contained in the provided compositions typically have an HLB value between 14 or about 14 and 20 or about 20, for example, 14, 15, 16, 17, 18, 19, 20, about 14, about 15, about 16, about 17, about 18, about 19 or about 20. Exemplary of the surfactants include, but are not limited to, non-ionic surfactants, such as polyethylene glycol (PEG)-Sorbitan fatty acid esters, for example, polysorbates, including PEG-sorbitan monooleates, such as Polyoxyethylene (20) sorbitan monooleate (also called polysorbate 80), as well as analogs of polysorbate 80, such as polysorbate 80 homologs and polysorbate 80 derivatives. Exemplary of the polysorbate 80 analogs are polysorbate 40 (polyoxyethylene (20) sorbitan monopalmitate), polysorbate 60 (polyoxyethylene (20) sorbitan monostearate) and polysorbate 20 (polyoxyethylene (20) sorbitan monolaurate).

In one aspect, the surfactant is a polysorbate 80 homolog, such as, for example, a polysorbate 80 homolog that differs from a polysorbate 80 parent compound by the addition or removal of one or more methylene unit(s), e.g., $-(CH_2)_n-$.

Other known surfactants having HLB values between 14 or about 14 and 20 or about 20, typically between about 16 and 18, also can be suitable. For example, surfactants having similar properties to polysorbate 80 also can be used. Typically, the surfactant is a natural surfactant, for example, a surfactant that is G.R.A.S. (generally recognized as safe) by the FDA and/or Kosher certified.

As used herein, micelle refers to aggregates formed by surfactants that typically form when the surfactant is present in an aqueous composition, typically when the surfactant is used at a concentration above the critical micelle concentration (CMC). In micelles, the hydrophilic portions of the surfactant molecules contact the aqueous or the water phase, while the hydrophobic portions form the core of the micelle, which can encapsulate non-polar ingredient(s), for example, the non-polar compounds in the provided compositions. Typically, the surfactants in the provided compositions form micelles containing the non-polar ingredient at their center in aqueous liquid dilution compositions. Typically, the micelles in the provided compositions have a particle size of about 1000 nm, typically, less than 500 nm or less than about 500 nm, typically less than 300 or about 300 nm, for example, less than 250 nm or about 250 nm, for example, less than 200 nm or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm.

As used herein, inverse micelles are surfactant aggregates that typically form in lipophilic solution, with the hydrophilic portions forming the core. When the cross sectional area of the hydrophobic region of the surfactant molecule is greater than that of the hydrophilic part of the molecule, the formation of micelles, which can be hexagonal phase structures, is favored.

As used herein, liposomes are surfactant aggregates composed of lipid bilayers, typically having an aqueous core. Liposomes typically are formed by lipid surfactants, typically, phospholipids, which are amphipathic, phosphate-containing lipids, for example, molecules containing one phosphate, a glycerol and one or more fatty acids, and similar surfactants. Alternatively, phospholipid surfactants can be used as co-surfactants, which can be incorporated into aggregates of other surfactant(s), for example, micelles. Lipid bilayers are two dimensional sheets in which all of the hydrophobic portions, e.g., acyl side chains, are shielded from interaction with aqueous liquid, except those at the ends of the sheet. An energetically unfavorable interaction of the acyl chains with water results in the folding of the bilayers to form liposomes, three-dimensional lipid bilayer vesicles. In one example, the liposome is formed as a single bilayer enclosing a single aqueous space (small unilamellar vesicles; SUVS). In another example, the liposome is composed of concentric bilayers with many aqueous spaces alternating with the bilayers (multilamellar vesicles; MLVS). Liposomes can be used to encapsulate hydrophobic and hydrophilic active ingredients. In liposomes, non-polar active ingredients typically are partitioned within the bilayers whereas hydrophilic active ingredients typically are trapped within the aqueous compartments. In one example, liposomes can be advantages as a carrier/encapsulation system because they are stable and can protect the active ingredients from degradation, e.g., by oxygen and digestive enzymes.

As used herein, "co-surfactant" is used to refer to a surfactant, typically a phospholipid, that is used, in the provided compositions, in combination with a surfactant, for example, a primary surfactant, for example, to improve the emulsification of the provided compositions and/or compounds, for example, to emulsify the ingredients. In one example, the provided compositions contain at least one surfactant and at least one co-surfactant. Typically, the co-surfactant is a lipid, for example, a phospholipid, for example, phosphatidylcholine. In one example, the co-surfactant has an HLB value of between 7 or about 7 and 8 or about 8. Typically, the co-surfactant represents a lower percent, by weight, of the provided compositions, compared to the surfactant. Thus, the provided compositions typically have a lower concentration of the co-surfactant(s) than of the surfactant.

As used herein, a phospholipid is an amphipathic, phosphate-containing lipid, for example, a molecule containing one phosphate, a glycerol and one or more fatty acids. In one example, one or more phospholipids is used as a co-surfactant in the provided compositions. Exemplary of the phospholipids used in the provided compositions are lecithin, including phosphatidylcholine (PC), phosphatidylethanolamine (PE), distearoylphosphatidylcholine (DSPC), phosphatidylserine (PS), phosphatidylglycerol (PG), phosphatidic acid (PA), phosphatidylinositol (PI), sphingomyelin (SPM) or a combination thereof. Typically, the phospholipid is phosphatidylcholine (PC), which sometimes is referred to by the general name "lecithin." Exemplary of the phospholipids that can be used as co-surfactants in the provided compositions are the phospholipids sold by Lipoid, LLC, Newark, N.J., for example, Purified Egg Lecithins, Purified Soybean Lecithins, Hydrogenated Egg and Soybean Lecithins, Egg Phospholipids, Soybean Phospholipids, Hydrogenated Egg and Soybean Phospholipids. Synthetic Phospholipids, PEGylated Phospholipids and phospholipid blends sold by Lipoid, LLC. Exemplary of the phosphatidylcholine that can be used as a co-surfactant in the provided compositions is the phosphatidylcholine composition sold by Lipoid, LLC, under the name Lipoid S100, which is derived from soy extract and contains greater than 95% or greater than about 95% phosphatidylcholine.

Typically, for micelle formation, surfactant(s) are used in which the cross sectional area of the hydrophilic portion of the surfactant molecule is greater than that of the hydrophobic portion of the molecule. For example, polysorbate 80 is a surfactant used to stabilize oil-in-water emulsions containing the non-polar active ingredients, for example, in nanometer-sized droplets suspended or dispersed in an aqueous phase or aqueous liquid, for example, aqueous medium, as spherical micelles, containing the hydrophilic portions of the molecule(s) facing the aqueous phase and the hydrophobic portions at the center of the spherical micelles, for example, surrounding the non-polar active ingredient.

Typically, in the provided compositions, the surfactants and/or co-surfactants, aggregate in the nanoemulsions and the aqueous liquids to form micelles, which contain the non-polar compound(s). The hydrophilic portion(s) of the surfactant molecules are oriented toward the outside of the micelle, in contact with the aqueous medium, while the hydrophobic portion(s) of the surfactant molecules are oriented toward the center of the micelle, in contact with the non-polar compound(s), which is contained in the center of the micelle. The micelles can contain more than one surfactant.

As used herein, a polysorbate is a compound belonging to the family of oily liquids containing esters derived from PEGylated sorbitan (derivative of sorbitol) esterified with one or more fatty acids. Exemplary polysorbate surfactants are Polysorbate 20 (polyoxyethylene (20) sorbitan monolaurate; sold under the trade name Tween 20®); polysorbate 40 (Tween 40® or polyoxyethylene (20) sorbitan monopalmitate); polysorbate 60 (Tween 60® or polyoxyethylene (20) sorbitan monostearate); and polysorbate 80 (Tween 80® or polyoxyethylene (20) sorbitan monooleate). With the parenthetically indicated naming convention for the polysorbates above, the number 20 following "polyoxyethylene" refers to the number of oxyethylene —($CH_2CH_2O$)— groups in the molecule. With the naming convention beginning with "polysorbate" (e.g. "polysorbate 80), the number refers to the type of fatty acid used to esterify the polyoxyethylene sorbitan to generate the polysorbate. For example, the number 20 indicates monolaurate; the number 40 indicates monopalmitate; the number 60 indicates monostearate; and the number 80 indicates monooleate. In one example, the surfactant(s) used in the provided compositions are polysorbate surfactants, including polysorbate 80, for example, the polysorbate 80 sold under the trademark, Tween 80®.

As used herein, "polysorbate 80" is used synonymously with "polyoxyethylene (20) sorbitan monooleate" to refer to a polysorbate derived from polyoxylated sorbitan and oleic acid, having the structure set forth in Scheme I, where w+x+y+z=20:

Scheme I:

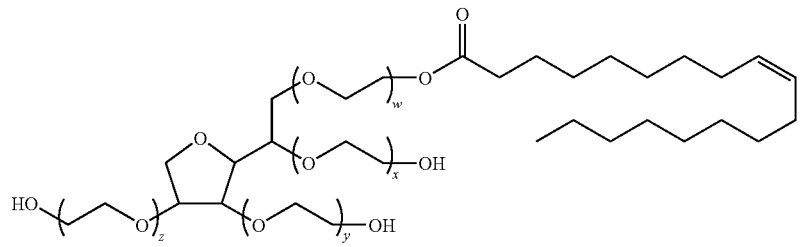

As used herein, "particle size" and "average particle size" refer synonymously to the average diameter of particles in a provided liquid, for example, the droplet diameter or micelle diameter in an emulsion. Typically, the provided nanoemulsion concentrates, and the liquids made from the concentrates, have a particle size of less than about 1000 nm, typically, less than 500 nm or less than about 500 nm, typically less than 300 or about 300 nm, for example, less than 250 nm or about 250 nm, for example, less than 200 nm or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. In one example, the dilution compositions yielded by diluting the liquid nanoemulsion concentrates have a particle size between 10 nm or about 10 nm and 1000 nm or about 1000 nm, for example, between 15 nm or about 15 nm and 500 nm or about 500 nm, for example, between 15 nm or about 15 nm and 300 nm or about 300 nm, for example, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200 nm or more. Typically, the provided liquid nanoemulsion concentrates are formulated such that, dilution of the liquid nanoemulsion concentrates in an aqueous medium yields a liquid dilution composition having an appropriate particle size, for example, between 15 nm or about 15 nm and 500 nm or about 500 nm. Information about particles in the liquids alternatively can be expressed in terms of particle number, for example, ppm (parts per million) or percent solids, in the liquids.

As used herein, visible particles are particles, for example, in a liquid, for example, an emulsion, that are visible when viewing the liquid with the naked eye (e.g. without magnification). In one example, the visible particles are particles that are observed by the artisan formulating the compositions, for example, the concentrates or the aqueous liquid dilution compositions containing the diluted concentrates. In one example, the provided compositions contain no visible particles. In another example, the compositions contain few visible particles, for example, no more visible particles than another liquid, for example, a beverage. The presence of visible particles and the number of visible particles is determined by empirical observation.

As used herein, visible crystals are crystals, for example, in a liquid, for example, an emulsion, that are visible when viewing the liquid with the naked eye (e.g. without magnification). In one example, the visible crystals are crystals that are observed by the artisan formulating the compositions, for example, the concentrates or the aqueous liquid dilution compositions containing the diluted concentrates. In one example, the provided compositions contain no visible crystals. In another example, the compositions contain few visible crystals, for example, no more visible crystals than are contained in another liquid, for example, a beverage. The presence of visible crystals is determined by empirical observation.

As used herein, "turbidity" is a measure of the cloudiness or haziness of a liquid, caused by particles in suspension in the liquid. Turbidity can measured optically, for example, using a nephelometer, an instrument with a light and a detector. The nephelometer measures turbidity by detecting scattered light resulting from exposure of the liquid to an incident light. The amount of scattered light correlates to the amount of particulate matter in the liquid. For example, a beam of light will pass through a sample with low turbidity with little disturbance.

Turbidity can measured optically, for example, by using a nephelometer, an instrument with a light and a detector. The nephelometer measures turbidity by detecting scattered light resulting from exposure of the liquid to an incident light. The amount of scattered light correlates to the amount of particulate matter in the liquid. For example, a beam of light will pass through a sample with low turbidity with little disturbance. Other methods for measuring turbidity are well known and can be used with the provided methods and compositions. The units of a turbidity value measured with a nephelometer are Nephelometric Turbidity Units (NTU). In one example, the provided compositions, for example, the aqueous liquid dilution compositions containing the diluted liquid nanoemulsion concentrates have low turbidity, for example, a turbidity value (NTU) of 30 or about 30; or an NTU value of less than 30 or about 30, for example, less than 29 or about 29, less than 28 or about 28, less than 27 or about 27, less than 26 or about 26, less than 25 or about 25, less than 24 or about 24, less than 23 or about 23, less than 22 or about 22, less than 21 or about 21, less than 20 or about 20, less than 19 or about 19, less than 18 or about 18, less than 17 or about 17, less than 16 or about 16, less than 15 or about 15, less than 14 or about 14, less than 13 or about 13, less than 12 or about 12, less than 11 or about 11, less than 10 or about 10, less than 9 or about 9, less than 8 or about 8, less than 7 or about 7, less than 6 or about 6, less than 5 or about 5, less than 4 or about 4, less than 3 or about 3, less than 2 or about 2, less than 1 or about 1; or 29 or about 29, 28 or about 28, 27 or about 27, 26 or about 26, 25 or about 25, 24 or about 24, 23 or about 23, 22 or about 22, 21 or about 21, 20 or about 20, 19 or about 19, 18 or about 18, 17 or about 17, 16 or about 16, 15 or about 15, 14 or about 14, 13 or about 13, 12 or about 12, 11 or about 11, 10 or about 10, 9 or about 9, 8 or about 8, 7 or about 7, 6 or about 6, 5 or about 5, 4 or about 4, 3 or about 3, 2 or about 2, 1 or about 1, or 0 or about 0. In another example, the turbidity value of the aqueous liquid dilution composition is less than 1000 or less than about 1000, less than 500 or less than about 500, less than 300 or less than about 300, less than 250 or less than about 250, 200 or less than about 200, for example, 200, 175, 150, 100, 50, 25 or less.

As used herein, a turbid liquid is one that is thick or opaque with visible particles in suspension, for example, a liquid that is cloudy or muddy in appearance.

As used herein, "clear" can be used to describe a composition as provided herein, for example, the aqueous liquid dilution compositions containing the diluted nanoemulsion concentrates and/or the nanoemulsion concentrates themselves. In one example, a clear liquid is one that does not appear cloudy by empirical observation (e.g. to the naked eye) and/or does not contain particles or crystals that are visible to the naked eye, or that does not exhibit "ringing." In another example, a clear liquid is one that has a low or relatively low turbidity value, for example an NTU value, that is less than or equal to a desired NTU value. In one example, a clear liquid has an NTU value of less than 300 or less than about 300, typically less than 250 or less than about 250, typically less than 200 or less than about 200, for example, 200, 175, 150, 100, 50, 25 or less. In another example, a liquid is clear if it has a turbidity value (NTU) of 30 or about 30; or an NTU value of less than 30 or about 30, for example, less than 29 or about 29, less than 28 or about 28, less than 27 or about 27, less than 26 or about 26, less than 25 or about 25, less than 24 or about 24, less than 23 or about 23, less than 22 or about 22, less than 21 or about 21, less than 20 or about 20, less than 19 or about 19, less than 18 or about 18, less than 17 or about 17, less than 16 or about 16, less than 15 or about 15, less than 14 or about 14, less than 13 or about 13, less than 12 or about 12, less than 11 or about 11, less than 10 or about 10, less than 9 or about 9, less than 8 or about 8, less than 7 or about 7, less than 6 or about 6, less than 5 or about 5, less than 4 or about 4, less than 3 or about 3, less than 2 or about 2, less than 1 or about 1; or 29 or about 29, 28 or about 28, 27 or about 27, 26 or about 26, 25 or about 25, 24 or about 24, 23 or about 23, 22 or about 22, 21 or about 21, 20 or about 20, 19 or about 19, 18 or about 18, 17 or about 17, 16 or about 16, 15 or about 15, 14 or about 14, 13 or about 13, 12 or about 12, 11 or about 11, 10 or about 10, 9 or about 9, 8 or about 8, 7 or about 7, 6 or about 6, 5 or about 5, 4 or about 4, 3 or about 3, 2 or about 2, 1 or about 1, or 0 or about 0. In another example, a clear liquid is one that has a small or relatively small average particle size (e.g. less than 1000 nm or about 1000 nm, typically less than 500 nm or less than about 500 nm, typically less than 300 nm or about 300 nm, typically less than 250 nm or about 250 nm, typically less than 200 nm or about 200 nm, for example, less than 150 or about 150 nm, less than 100 nm or about 100 nm, less than 75 nm or about 75 nm, less than 50 nm or about 50 nm, less than 25 nm or about 25 nm or less than 10 nm or about 10 nm), for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm.

In another example, clarity is expressed relatively. For example, it can be desired that a particular composition is equally as clear, about as clear, or more clear than another liquid (as measured empirically, or by measuring turbidity value or particle size). For example, clarity can be assessed relative to another aqueous liquid dilution composition, for example, a beverage For example, In one example, a liquid is clear if it is similar in appearance to another clear liquid, for example, a beverage, for example, water. For example, it can be desired that a composition has a particle size that is less than or equal to another liquid, for example, a beverage. In another example, it can be desired that a composition has a turbidity value that is less than or equal to another liquid, for example, a beverage. In another example, it can be desired that a composition appears more clear or as clear as another liquid, for example, a beverage, for example, by having no more visible particles, no more crystal formation and/or no more cloudiness than the other liquid. In one example, the provided compositions are clear. In another example, they are relatively clear or as clear as or about as clear as another liquid, for example, a beverage that does not contain the non-polar compound or liquid nanoemulsion concentrate.

As used herein, "hydrophilic" refers to ingredients and/or compounds having greater solubility in aqueous liquids, for example, water, than in fats, oils and/or organic solvents (e.g. methanol ethanol, ethyl ether, acetone and benzene).

As used herein, "non-polar" "lipophilic" and "lipid-soluble" synonymously refer to compounds (e.g. non-polar compounds) and/or ingredients, for example, non-polar active ingredients, which have greater solubility in organic solvents (e.g. ethanol, methanol, ethyl ether, acetone, and benzene) and in fats and oils, than in aqueous liquids, for example, water. Non-polar compounds include drugs, hormones, vitamins, nutrients and other lipophilic compounds. Typically, the non-polar compounds used in the provided compositions are poorly water soluble, for example, water insoluble or compounds having low water solubility. Exemplary non-polar compounds include non-polar active ingredients, for example, lipid-soluble drugs, hormones, essential fatty acids, for example, polyunsaturated fatty acids (PUFA), for example, omega-3 and omega-6 fatty acids, vitamins, nutrients, neutraceuticals, minerals and other compounds. Additional exemplary non-polar compounds are described herein. The provided compositions can be formulated with any non-polar compound, for example, non-polar active ingredient.

As used herein, non-polar active ingredient refers to a non-polar compound that, when administered to a subject, for example, a human, induces or is proposed to induce a desired response, such as altering body function at the cellular, tissue, organ or other level, and/or altering cosmetic appearance or other property, or a non-polar compound that is ingested in order to achieve a desired effect. Non-polar active ingredients can be any synthetic or natural non-polar ingredient or compound, including a pharmaceutical, drug, therapeutic, nutritional supplement, herb, hormone or other ingredient. Non-polar active ingredients can include the non-polar active ingredients listed herein, as well as other pharmaceutically acceptable or food-grade active derivatives of the active ingredients, for example, salts, esters, amides, prodrugs, active metabolites, isomers, fragments and analogs. Active ingredients can include compounds proven to have a desired effect and also compounds thought to produce such effects, for example, compounds typically ingested for nutritional supplementation purposes.

As used herein, a subject includes an animal, typically a mammal, typically a human.

As used herein, an additives include anything that one can add to a food, beverage, or other human consumable, to enhance one or more of its nutritional, pharmaceutical, dietary, health, nutraceutical, health benefit, energy-providing, treating, holistic, or other properties. For example, provided herein are compositions and methods for preparing foods, beverages and other aqueous human consumables, that include one or more additives, typically oil based additives (e.g. non-polar compounds), such as nutraceuticals, pharmaceuticals, vitamins, typically oil soluble vitamins, for example, Vitamin D, E and A, minerals, fatty acids, such as essential fatty acids, e.g. polyunsaturated fatty acids, for example, omega-3 fatty acids and omega-6 fatty acids, for example, ALA, DHA, EPA, GLA, CLA, saw palmetto extract, flaxseed oil, fish oil, algae oil, phytosterols, and Coenzymes, for example, Coenzyme Q10 and other additives.

As used herein, an effective amount of an additive, such as a non-polar compound, such as a non-polar active ingredient, refers to the quantity and/or concentration of the additive necessary for preventing, curing, ameliorating, arresting or partially arresting a symptom of a disease or disorder, or the quantity and/or concentration desired by an individual for intake, such as daily intake, and/or nutritional supplementation, for example, an amount sufficient to enhance the nutritional, pharmaceutical, nutraceutical, health or energy property of a food, beverage, or other consumable. In some examples, it is desired that the provided compositions, for example, the liquid nanoemulsion concentrates and/or the liquid dilution compositions, contain an effective amount of a particular non-polar compound, for example, a particular amount per volume or weight of the composition.

In one example, an effective amount is a concentration or amount of a liquid nanoemulsion concentrate where at least 25 mg or about 25 mg, typically at least 35 mg, for example, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000 mg, or more, of the non-polar active ingredient, is contained in at least 8 fluid ounces of an aqueous medium, e.g. a beverage.

As used herein, unit dose form refers to physically discrete units suitable for human and animal subjects and packaged individually as is known in the art.

As used herein, "water insoluble" refers to a property of a compound, none of which dissolves when the compound is mixed with water, for example, when mixed with water at room temperature, for example, between 25 and 50° C. or between about 25 and 50° C. In one example, the non-polar compounds are water insoluble. In another example, the non-polar compounds in the provided compositions are slightly soluble in water, for example, having low water solubility.

As used herein, low water solubility refers water solubility of less than 30 or about 30 mg/mL, typically less than 20 mg/mL or about 20 mg/mL, typically, less than 10 mg/mL or about 10 mg/mL, typically less than 1 mg/mL or about 1 mg/mL, for example, solubility in water of 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 mg/mL or less, for example, when mixed with water at room temperature, for example, between 25 and 50° C. or between about 25 and 50° C. As used herein, poorly water soluble can be used to refer to compounds, for example, non-polar compounds that are water insoluble or have low water solubility.

As used herein, concentrate, liquid concentrate and liquid nanoemulsion concentrate, are used synonymously to refer to provided compositions that contain the non-polar compounds, are liquid at room temperature, for example at 25° C. or about 25° C., or at a temperature of between 25° C. or about 25° C. and 50° C. or about 50° C., and can be diluted in aqueous media to form the provided aqueous liquid dilution compositions. Typically, the liquid nanoemulsion concentrate is an emulsion concentrate that has a particle (droplet) size (or can be diluted to form an aqueous liquid dilution composition having a particle size) that is less than 1000 or about 1000, typically less than 500 or about 500, typically less than 300 or about 300 nm, typically less than 250 or about 250 nm, for example, less than 200 or about 200, for example, less than 150 or about 150 nm, for example, a particle size equal to, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. Typically, the liquid nanoemulsion concentrate contains one or more non-polar active ingredients, a surfactant and water. In some examples, the concentrates further contain one or more of a preservative (e.g. a natural preservative, such as benzyl alcohol), a co-surfactant (e.g. a phospholipid, such as phosphatidylcholine), an emulsion stabilizer, a pH adjuster, and flavor. The provided concentrates can be diluted to form liquid dilution compositions, typically aqueous liquid dilution compositions. In one example, the aqueous liquid dilution composition are clear aqueous liquid dilution compositions.

Typically, the liquid nanoemulsion concentrate is formulated (e.g. using the provided methods for formulating the concentrates) such that dilution of the concentrate in an aqueous medium yields an aqueous liquid dilution composition having one or more desirable properties, for example, being free from visible particles and/or visible crystals, exhibiting no ringing or phase separation, and/or having a desirable clarity, for example, a desired turbidity (NTU) value (e.g. an NTU of less than 1000 or about 1000, typically less than 500 or about 500, typically less than 300 or about 300 nm, typically less than 250 or about 250 typically less than 200 or about 200, e.g. less than 150 or about 150) or a desired average particle size (e.g. less than 1000 or about 1000, typically less than 500 or about 500, typically less than 300 or about 300 nm, typically less than 200 or about 200, for example, a particle size equal to, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm). In another example, the liquid nanoemulsion concentrate is formulated such that dilution of the concentrate in an aqueous medium, for example, a beverage, yields a liquid dilution composition that is as clear as or substantially as clear as the aqueous medium itself.

As used herein, liquid composition is used to refer to any liquid, for example, a composition that is a liquid at room temperature, for example, at 25° C. or about 25° C., or at a temperature of between 25° C. or about 25° C. and 50° C. or about 50° C. Exemplary of the provided liquid dilution compositions are aqueous liquid dilution compositions into which one or more liquid nanoemulsion concentrate has been diluted, for example, aqueous liquid dilution compositions containing the diluted concentrates. In this example, the non-polar compound and other lipophilic compounds in the concentrate form the dispersion phase within the aqueous liquid, which is an emulsion (e.g. nanoemulsion).

As used herein, "liquid dilution composition" "dilution composition" and "liquid dilution" are used synonymously to refer to a composition that contains one or more of the provided liquid nanoemulsion concentrates (e.g. the liquid nanoemulsion concentrates containing the non-polar compound(s)), diluted in a liquid, for example, an aqueous medium. Exemplary of the provided liquid dilution compositions are aqueous liquid dilution compositions, for example, beverages or other liquids containing the liquid nanoemulsion concentrates, for example, water, sauces, soups, syrups, soda, juice, for example, fruit juice, milk, coffee, tea, nutritional beverages, sports drinks, energy drinks, vitamin-fortified beverages, flavored water, and other beverages containing the diluted concentrates.

As used herein, aqueous liquid dilution compositions are liquid dilution compositions that are primarily aqueous, for example, a composition comprising a liquid nanoemulsion concentrate diluted in an aqueous medium, for example, water or other beverage. It is not necessary that the aqueous liquid dilution composition is completely aqueous. For example, the aqueous liquid dilution compositions can contain an aqueous portion, for example, an aqueous continuous phase, as well as an additional portion, for example, a dispersion phase, for example, a lipophilic dispersion phase. Typically, the lipophilic dispersion phase contains one or more lipophilic substances, for example, one or more non-polar compounds, for example, non-polar active ingredients.

In one example, the dispersion phase of the aqueous liquid dilution composition has a small droplet (particle) size, for example, a particle size of less than 1000 or about 1000, typically less than 500 or about 500, typically less than 300 or about 300 nm, typically less than 250 or about 250 nm, typically less than 200 or about 200 nm, for example, a particle size equal to, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. Exemplary of the provided aqueous liquid dilution compositions are beverages, for example, water, soda, juice, for example, fruit juice, milk, coffee, tea, nutritional beverages, sports drinks, energy drinks, vitamin-fortified beverages, flavored water, and other beverages. Typically, the aqueous liquid dilution compositions are beverages including the non-polar compound, for example, beverages containing the diluted concentrates.

As used herein, "oil phase" is used to refer to the portion (or phase) of the compositions, typically of the liquid nanoemulsion concentrates, that contains one or more lipophilic ingredients and/or amphiphilic ingredients (oil phase ingredients) and is, in general, the lipid-soluble phase. In the provided nanoemulsion compositions (e.g. the nanoemulsion concentrates and the dilution compositions), the oil phase typically represents the dispersion phase. "Oil phase" also can be used to refer to the liquid containing the oil phase ingredients that is generated, typically in an oil phase vessel, while carrying out the methods for making the liquid nanoemulsion concentrates. For example, oil phase can refer to the mixture of the components (oil phase ingredients) that are combined, mixed and heated, for example, in the oil phase vessel (e.g. tank), prior to mixing with the water phase. "Oil phase" can refer to the oil phase mixture that is formed after all the ingredients are dissolved; alternatively, it can refer to the forming mixture, for example, as it is being mixed/heated.

As used herein, oil phase ingredient(s) refers to the components of the provided compositions that are included in the oil phase in the provided methods for making the compositions. Typical oil phase ingredients include the non-polar compound, for example, the non-polar active ingredient, one or more surfactants, one or more co-surfactants, oils, for example, solvents, preservatives, and/or emulsion stabilizers. Other lipophilic and/or amphiphilic ingredients can be included in the oil phase.

As used herein, "water phase" is used to refer to the portion (phase) of the compositions, typically of the liquid nanoemulsion concentrates, that contains one or more hydrophilic ingredients and/or amphiphilic ingredients (water phase ingredients) and is, in general, the water-soluble phase. Typically, in the provided nanoemulsion compositions, for example, the nanoemulsion concentrates and the dilution compositions, the water phase is the continuous phase. "Water phase" also is used to refer to the liquid containing the water phase ingredients that is generated while carrying out the methods for making the liquid nanoemulsion concentrates. For example, water phase can refer to the mixture of the components (water phase ingredients) that are combined, mixed and heated, for example, in the water phase tank, prior to mixing with the oil phase. "Water phase" can refer to the water phase mixture that is formed after all the ingredients are dissolved; alternatively "water phase" can refer to the forming mixture, for example, as it is being mixed/heated.

As used herein, water phase ingredient(s) refers to the components of the provided compositions that are included in the water phase (e.g. added to the water phase vessel) in the provided methods for making the compositions. Typical water phase ingredients include water, one or more surfactants, one or more co-surfactants, preservatives, and/or emulsion stabilizers. Other hydrophilic and/or amphiphilic ingredients can be included in the water phase.

As used herein, an initial concentrate is a concentrate (e.g. liquid nanoemulsion concentrate) that is made in the provided methods of formulating the concentrates, for example, the liquid nanoemulsion concentrates. Typically, the initial concentrate is made by selecting ingredients, for example, surfactant(s), non-polar compound(s), water and, optionally, other ingredients, and selecting starting concentrations of the ingredients from an appropriate concentration range as described herein. The initial concentrate can be formulated based on parameters of an existing concentrate, and/or according to the ingredients and concentration ranges provided herein. The initial concentrate is evaluated, for example, to determine whether the concentrate has one or more desirable properties, for example, clarity. In one example, changes are made to the formulation of the initial concentrate, as described herein. In another example, no changes are made and the formula of the initial concentrate is used to make the concentrate.

As used herein, stability refers to a desirable property of the provided compositions, for example, the ability of the provided compositions to remain free from one or more changes over a period of time, for example, at least or over 1, 2, 3, 4, 5, 6 or more days, at least or over 1, 2, 3, 4, or more weeks, at least or over 1, 2, 3, 4, 5, 6, 7, 8, 9, 10, 11, 12 or more months, or at least or over 1, 2, 3, 4 or more years. In one example, the composition is stable if it is formulated such that it remains free from oxidation or substantial oxidation over time. In another example, the stable compositions remain clear over time. In another example, the stable compositions remain safe and/or desirable for human consumption over time. In one example, stability refers to the lack of precipitates forming in the compositions over the period of time. In a related example, stability refers to the lack of "ringing" over the period of time. In another example, the composition is stable if it does not exhibit any visible phase separation over a period of time, for example, after 24 hours, after one week or after one month. In one example, the compositions are stable if they exhibit one or more of these described characteristics, over time, when kept at a particular temperature. In one example, the compositions remain stable at room temperature, for example, 25° C. or about 25° C. In another example, the compositions remain stable at between 19° C. and 25° C. In another example, the compositions remain stable at refrigerated temperatures, for example, 4° C. or about 4° C., or at frozen temperature, for example, at −20° C. or about −20° C.

As used herein, stabilize means to increase the stability of one of the provided compositions.

As used herein, room temperature and ambient temperature are used to describe a temperature that is common in one or more enclosed spaces in which human beings typically are or reside. Room temperature can vary, but generally refers to temperatures between 19° C. or about 19° C. and 25° C. or about 25° C. When a composition is stored at room temperature, it should be understood it is generally kept at a temperature within this range or about within this range.

As used herein, refrigerated temperature refers to a temperature that is common in a refrigerator, for example, a household or restaurant refrigerator, for example, a temperature that is cooler than room temperature, but typically a few degrees above the freezing point of water (0° F. or about 0° F., or −19° C. or −20° C.). Typically, refrigerated temperatures are between about 10° C. or about 10° C. and 0° C. or about 0° C., for example, 4° C. or about 4° C. When a composition is stored at a refrigerated temperature, it should be understood that it is kept at a temperature common to household or industrial refrigerators.

As used herein, frozen temperature refers to a temperature around or below the freezing point of water, e.g. a temperature commonly used in a household freezer, for example, 0° F. or about 0° F., for example, −19° C. or about −19° C. or −20° C. or about −20° C., or colder.

As used herein, the singular forms "a," "an" and "the" include plural referents unless the context clearly dictates otherwise. Thus, for example, reference to compound, comprising "an extracellular domain" includes compounds with one or a plurality of extracellular domains.

As used herein, ranges and amounts can be expressed as "about" a particular value or range. About also includes the exact amount. Hence "about 5 grams" means "about 5 grams" and also "5 grams.' It also is understood that ranges expressed herein include whole numbers within the ranges and fractions thereof. For example, a range of between 5 grams and 20 grams includes whole number values such as 5, 6, 7, 8, 9, 10, 11, 12, 13, 14, 15, 16, 17, 18, 19 and 20 grams, and fractions within the range, for example, 5.25, 6.72, 8.5, 11.95, etc. grams.

As used herein, "optional" or "optionally" means that the subsequently described event or circumstance does or does not occur and that the description includes instances where said event or circumstance occurs and instances where it does not. For example, an optionally variant portion means that the portion is variant or non-variant. In another example, an optional ligation step means that the process includes a ligation step or it does not include a ligation step.

As used herein, "ringing" refers to the formation of a whitish or opaque ring around a container containing a liquid, for example, an aqueous liquid, for example a beverage, for example, a liquid dilution composition containing an emulsion or nanoemulsion. Typically, the ring forms around the perimeter of the container, typically at the surface level of the liquid in the container, for example, at the neck of the container. Ringing can occur over time and, if it occurs over a short period of time, can be a sign of instability. Ringing typically is undesirable, particularly in the case of a liquid for human consumption, for example, a beverage. Typically, the provided compositions do not exhibit "ringing" or are stable, without ringing, for a long period of time, for example, days, weeks, months or years. In one example, the compositions are free from ringing over time, when kept, for example, at room temperature, refrigerated and/or frozen. These desired properties of the provided compositions related to ringing can be affected by the particle size of the compositions, which can be influenced by selection of particular ingredients and concentrations of ingredients, for example, by properties of the surfactant(s), for example, the HLB of the surfactant(s).

As used herein, fatty acid refers to straight-chain hydrocarbon molecules with a carboxyl (COOH) group at one end of the chain.

As used herein, polyunsaturated fatty acid and PUFA are used synonymously to refer to fatty acids that contain more than one carbon-carbon double bond in the carbon chain of the fatty acid. PUFAs, particularly essential fatty acids, are useful as dietary supplements.

As used herein, essential fatty acids are PUFAs that mammals, including humans, cannot synthesize using any known chemical pathway. Thus, essential fatty acids must be obtained from diet or by supplementation. Exemplary of essential PUFA fatty acids are omega-3 (ω3; n-3) fatty acids and the omega-6 (ω6; n-6) fatty acids.

As used herein, omega-3 (ω3; n-3) fatty acids are methylene interrupted polyenes, which have two or more cis double bonds, separated by a single methylene group and in which the first double bond appears at the third carbon from the last (ω) carbon. Omega-3 fatty acids are used as dietary supplements, for example, for disease treatment and prevention. In one example, the provided compositions contain non-polar active ingredients that contain at least one omega-3 fatty acids. Exemplary of Omega-3 fatty acids are Alpha-Linolenic acid (α-Linolenic acid; ALA) (18:3ω3) (a short-chain fatty acid); Stearidonic acid (18:4ω3) (a short-chain fatty acid); Eicosapentaenoic acid (EPA) (20:5ω3); Docosahexaenoic acid (DHA) (22:6ω3); Eicosatetraenoic acid (24:4ω3); Docosapentaenoic acid (DPA, Clupanodonic acid) (22:5ω3); 16:3 ω3; 24:5 ω3 and nisinic acid (24:6ω3). Longer chain Omega-3 fatty acids can be synthesized from ALA (the short-chain omega-3 fatty acid). Exemplary of non-polar active ingredients containing omega-3 fatty acids are non-polar active ingredients containing DHA and/or EPA, for example, containing fish oil, krill oil and/or algae oil, for example, microalgae oil, non-polar active ingredients containing alpha-linolenic acid (ALA), for example, containing flaxseed oil.

As used herein, omega-6 (ω6; n-6) fatty acids are methylene interrupted polyenes, which have two or more cis double bonds, separated by a single methylene group and in which the first double bond appears at the sixth carbon from the last (ω) carbon. In one example, the provided compositions contain non-polar active ingredients that contain at least one omega-3 fatty acids. Exemplary of Omega-6 fatty acids are Linoleic acid (18:2ω6) (a short-chain fatty acid); Gamma-linolenic acid (GLA) (18:3ω6); Dihomo gamma linolenic acid (DGLA) (20:3ω6); Eicosadienoic acid (20:2ω6); Arachidonic acid (AA) (20:4ω6); Docosadienoic acid (22:2ω6); Adrenic acid (22:4ω6); and Docosapentaenoic acid (22:5ω6). Exemplary of non-polar active ingredients containing omega-6 fatty acids are ingredients containing GLA, for example, borage oil. Also exemplary of PUFA-containing non-polar active ingredients are compounds containing conjugated fatty acids, for example, Conjugated linoleic acid (CLA) and compounds containing saw palmetto extract.

As used herein, algae oil refers to any oil derived from marine dinoflagellates in, for example, microalgae, for example, *Crypthecodinium sp*, particularly, *Crypthecodinium cohnii*. In one example, algae oil is used as a non-polar compound, for example, as an active ingredient, in the provided compositions. The algae oil typically contains DHA. In one example, the algae oil is also a source of EPA.

As used herein, fish oil refers to any oil derived from any fish, typically a cold water fish, for example, from fish tissue, for example, from frozen fish tissue, for example, from cod liver. In one example, fish oil is used as a non-polar compound, for example, an active ingredient, in the provided compositions. The fish oil typically contains DHA. In one example, the fish oil also contains EPA.

As used herein, preservative and preservativer are used synonymously to refer to ingredients that can improve stability of the provided compositions. Preservatives, particularly food and beverage preservatives, are well known. Any known preservative can be used in the provided compositions. Exemplary of the preservatives that can be used in the provided compositions are oil soluble preservatives, for example, benzyl alcohol, Benzyl Benzoate, Methyl Paraben, Propyl Paraben, antioxidants, for example, Vitamin E, Vitamin A Palmitate and Beta Carotene. Typically, a preservative is selected that is safe for human consumption, for example, in foods and beverages, for example, a GRAS certified and/or Kosher-certified preservative, for example, benzyl alcohol.

As used herein, solvent refers to an ingredient, for example, an oil, that is used to dissolve a compound, typically, the non-polar compound, for example, the non-polar active ingredient. For example, the solvent can be used to dissolve the non-polar active ingredient prior to or simultaneous with its incorporation into the oil phase. Typically, the solvent is an oil that is included in the composition in addition to the non-polar compound. For example, the solvent typically is not the non-polar compound. Certain compounds, for example, flaxseed oil and safflower oil, can be solvents and non-polar active ingredients. Typically, the solvent contains one or more oils, typically oils other than the non-polar active ingredient or oil(s) not contained in the active ingredient. When a solvent is included in the concentrate, it typically is used to dissolve the non-polar compound before mixing with the other ingredients, for example, before mixing with the other oil phase ingredients. In one example, use of a solvent reduces the crystal size and/or increase the clarity of the aqueous liquid dilution composition containing the diluted concentrate. Exemplary of solvents that can be used in the provided concentrates are oils (in addition to the non-polar active ingredient), for example, Vitamin E oil, flaxseed oil, CLA, Borage Oil, D-limonene, Canola oil, corn oil, MCT oil and oat oil. Other oils also can be used. Exemplary of the Vitamin E oil, used as a solvent in the provided compositions, is the oil sold by ADM Natural Health and Nutrition, Decatur, Ill., under the name Novatol™ 5-67 Vitamin E (D-alpha-Tocopherol; ADM product code 410217). This Vitamin E oil contains at least 67.2% Tocopherol and approximately 32.8% soybean oil. In one example, the solvent is referred to, synonymously as "solubilizer."

As used herein, "w/w," "weight per weight," "by weight" "% by weight" and "weight percent" are used synonymously used to express the ratio of the mass of one component of a composition compared to the mass of the entire composition. For example, when the amount of a particular ingredient represents 1%, by weight (w/w) of a concentrate, the mass of that ingredient is 1% of the mass of the entire concentrate. Similarly, when the amount of an ingredient is 50% (w/w) of the concentrate, the mass of that ingredient is 50% of the entire mass of the concentrate. Similarly, when a composition and/or a compound contains 10%, by weight of an ingredient, the mass of the ingredient is 10% of the total mass of the composition or compound. When only a concentration, amount, or percentage (without units) is listed, it is to be understood that the concentration or percentage is a concentration or percentage, by weight.

Similarly, as used herein "v/v," "volume per volume," "percent by volume" and "volume percent" are used synonymously to express the ratio of the volume of one component of a composition and the volume of the entire composition.

As used herein, emulsion stabilizer refers to compounds that can be used to stabilize and/or emulsify and/or change the viscosity of the provided compositions, for example, the liquid nanoemulsion concentrate and/or the aqueous compositions containing the diluted concentrates. In one example, the emulsion stabilizer increases the viscosity of the liquid concentrate. In one example, one or more emulsion stabilizers is added, during formulation, after evaluation of an initial concentrate, particularly if the oil and water phases of the initial concentrate (or the aqueous liquid dilution composition resulting from dilution of the initial concentrate) appear to be separating. Addition of the emulsion stabilizer can prevent separation of the oil and water phases.

Exemplary of an emulsion stabilizer that can be used in the provided compositions is a composition containing a blend of gums, for example, gums used as emulsifying agents, for example, a blend containing one or more of xanthan gum, guar gum and sodium alginate, for example, the emulsion stabilizer sold under the brand name SALADIZER®, available from TIC Gums, Inc. (Belcamp, Md.). Other gums can be included in the emulsion stabilizer, for example, gum acacia and sugar beet pectin. Other blends of similar gums can also be used as emulsion stabilizers.

As used herein, a pH adjuster is any compound, typically an acid or a base, that is capable of changing the pH of the provided compositions, for example, to reduce the pH of the composition or to increase the pH of the composition, typically without altering other properties of the composition, or without substantially altering other properties. pH adjusters are well known. Exemplary of the pH adjusters are acids, for example, citric acid and phosphoric acid, and bases.

As used herein, flavor is any ingredient that changes, typically improves, the taste and/or smell of the provided composition, for example, the aqueous liquid dilution compositions, for example, the beverages.

As used herein, "not more than" and "NMT" refer to a quantity that is less than or equal to the listed quantity. Similarly, "not less than" and "NLT" refer to a quantity that is greater than or equal to the listed quantity.

As used herein, natural is used to refer to a composition, and/or ingredients in the composition, that can be found in nature and is not solely man-made. For example, benzyl alcohol is a natural preservative. Similarly, tocopheryl polyethylene glycol is a natural surfactant. In one example, the natural composition/ingredient is GRAS and/or Kosher—certified. Typically, the provided compositions are natural, semi-natural and/or contain one or more natural ingredients.

As used herein, "G.R.A.S." and "GRAS" are used synonymously to refer to compounds, compositions and ingredients that are "Generally Regarded as Safe" by the USDA, FDA for use as additives, for example, in foods, beverages and/or other substance for human consumption, for example, any substance that meets the criteria of sections 201(s) and 409 of the U.S. Federal Food, Drug and Cosmetic Act. Typically, the compositions provided herein are GRAS certified.

As used herein, kosher is used to refer to substances that conform to Jewish Kosher dietary laws, for example, substances that do not contain ingredients derived from non-kosher animals or ingredients that were not made following kosher procedures. Typically, the compositions provided herein are Kosher certified.

As used herein, vessel refers to any container, for example, tanks, pots, vials, flasks, cylinders and beakers, that can be used to contain the ingredients and/or phases of the provided compositions, during the methods for making the compositions. In one example (e.g. for the provided scaled-up methods), the vessel is a tank, which is used to mix and/or heat one or more ingredients and/or phases of the compositions, for example, water phase tanks and oil phase tanks. Typically, the oil and the water phases are mixed and heated in separate tanks, before combining the phases to form an emulsion. In another example, the tank is a packaging or holding tank, which holds the provided compositions after forming the compositions, for example, the emulsions. A number of tanks are available for mixing ingredients. Typically, the tanks are cleaned, for example, rinsed, soaped and/or sanitized according to know procedures, prior to use and between uses. Typically, the tanks are equipped with one or more mixers, for example, a standard mixer and/or homogenizer, which are used to mix the ingredients added to the tank. In one example, the tank further is equipped with a heating and/or cooling device. For example, the tank can be a water-jacketed tank. The temperature of the water-jacketed tank is controlled through the water-jacket, for example, to heat the contents, for example, while mixing.

As used herein, a water phase vessel refers to the vessel used to mix and/or heat the water phase ingredients to generate the water phase of the provided compositions. In one example (e.g. for the scaled-up methods), the water phase vessel is a water phase tank. In one example, the water phase tank is a water jacketed tank, which is equipped with a water jacket that can be used to heat the contents of the tank.

As used herein, an oil phase vessel refers to the vessel used to mix and/or heat the oil phase ingredients to generate the oil phase of the provided compositions. Typically, the oil phase vessel is an oil phase tank. In one example, the oil phase tank is a water jacketed tank.

As used herein, transfer means refers to any equipment, combination of equipment and/or system that can be used to transfer liquid, for example, from one tank to another tank, in the provided methods for making the compositions. Exemplary of the transfer means are a transfer pump and appropriate fittings, for example, sanitary fittings, ball valves and transfer hoses, for example, food grade hoses.

As used herein a mixer is any piece of equipment or combination of equipment that can be used to mix ingredients in the provided methods for making the compositions, for example, standard mixers and homoginizers (shears). For example, mixers can be used to mix the ingredients of the water phase, the oil phase, and/or to mix the additional ingredients.

As used herein, standard mixers are mixers that are used to combine a group of ingredients, for example, the oil phase ingredients or the water phase ingredients, or to mix one or more ingredients with a liquid, for example, with an emulsion, for example, to mix additional ingredients with the emulsion. Standard mixers can be any mixers that move the material, for example, the ingredients, during heating, for example, to promote dissolving of the ingredients.

As used herein, "homogeninzer" and "shear" are used to refer to mixers that typically have high shear, which can be used, for example, to form an emulsion, for example, to emulsify the water phase and the oil phase, in the provided methods. The homogenizers typically are capable of high-shear mixing, which emulsifies the phases.

As used herein, a cooling apparatus is any piece of equipment or combination of equipment that can be used with the provided methods to cool the compositions and phases and ingredients thereof, for example, during mixing and/or homogenizing, for example, to chill the mixture while emulsifying the oil and water phases. Exemplary of the cooling apparatuses are coolers (chillers), for example, recirculating coolers which can be attached, for example, to the tanks used in the provided methods, for example, remotely or by a tank mounted in the cooler, to recirculate fluid from the tank, through the chiller and back to the tank, in order to rapidly cool and maintain the temperature of the mixture during mixing. Typically, the cooling apparatus can be used to cool the liquid to between 25° C. or about 25° C. and 45° C. or about 45° C., for example, 25, 26, 27, 28, 29, 30, 31, 32, 33, 34, 35, 36, 37, 38, 39, 40, 41, 42, 43, 44 or 45° C., typically between 25° C. and 43° C., typically between 35° C. and 43° C., for example, 26.5° C.

As used herein, rapid cooling refers to a process by which a composition, for example, a liquid composition, for example, a forming emulsion, is cooled to a desired temperature, for example, between 25° C. or about 25° C. and 45° C. or about 45° C., typically between 35° C. and 43° C., for example, 26.5° C., in less than 2 hours or about 2 hours, typically less than 1 hour or about 1 hour, for example, in at least between 30 minutes or about 30 minutes and 60 minutes or about 60 minutes, for example, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes.

As used herein, low heat refers to a temperature between 45° C. or about 45° C. and 85° C. or about 85° C., for example, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85° C., for example, not more than 85° C. or about 85° C., typically not more than 60° C. or about 60° C., typically, 60° C. or 60° C. In the provided methods for making the liquid nanoemulsion concentrates, the oil phase and water phase ingredients typically are heated, using low heat, in order to preserve the ingredients, for example, in order to prevent oxidation of the ingredients, for example, the non-polar active ingredients, for example, the omega-3 containing compounds, for example, the DHA.

As used herein, "consisting essentially of," means containing the following list of ingredient(s), and not including any additional active ingredient, for example, not including any additional active drug or pharmaceutical. For example, a composition, for example, a liquid nanoemulsion concentrate, consisting essentially of a listed plurality of ingredients contains those particular ingredients and does not contain any additional active drug or pharmaceutical.

B. COMPOSITIONS CONTAINING NON-POLAR COMPOUNDS

Provided herein are compositions containing non-polar compounds and methods for making the compositions. Non-polar compounds are poorly water soluble (e.g. having low water solubility or being water-insoluble). Generally, because of this poor water solubility, it can be difficult to formulate non-polar compounds into compositions for human consumption, particularly aqueous compositions, for example, foods and beverages. Poor water solubility of non-polar compounds also can contribute to their poor bioavailability. Improved methods and compositions for formulating non-polar compounds are needed.

Emulsions (e.g. oil-in-water emulsions) have been used to disperse non-polar compounds in aqueous liquids. In general, emulsions are colloidal dispersions of two immiscible liquids (e.g. oil and water or other aqueous liquid), containing a continuous and a dispersed phase. In an oil-in-water emulsion, the dispersed phase is an oil phase and the continuous phase is an aqueous (water) phase. There remains a need, however, for improved emulsions (e.g. oil-in-water emulsions) containing non-polar compounds in aqueous liquids and methods and compositions for generating the improved emulsions. In particular, emulsions are needed that are more suitable and desirable for human consumption of the non-polar compounds, for example, in foods and beverages. For example, emulsions having improved clarity (e.g. small particle size, low turbidity), stability (e.g. lack of separation), taste and smell, are needed.

Among the provided compositions are such improved emulsions. For example, emulsions are provided that contain the non-polar compounds dispersed in aqueous liquid and have desirable properties, including improved clarity, stability, smell and taste. The provided compositions (and methods for making the compositions) can be used to formulate any non-polar compound in aqueous compositions.

Typically, the provided emulsions containing the non-polar compounds are nanoemulsions, which are emulsions having dispersed droplets (particles) with diameters less than 1000 nm or less than about 1000 nm, typically, less than 500 nm or less than about 500 nm, typically less than 300 or about 300 nm, typically less than 250 or less than about 250 nm, typically less than 200 nm or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. Typically, the provided nanoemulsion compositions are oil-in-water nanoemulsions, containing the non-polar compounds dispersed in aqueous liquid.

The provided emulsion compositions are stabilized by one or more surfactants and/or co-surfactants and/or emulsion stabilizers. Surfactants form an interfacial film in the emulsion, between the oil and water phase, providing stability. Typically, the nanoemulsions of the provided compositions contain micelles, in which one or more surfactant surrounds the non-polar active compound. The micelles are dispersed in the water phase.

Exemplary of the provided emulsion compositions are liquid nanoemulsion concentrates containing the non-polar compounds, which can be diluted to provide non-polar compounds in aqueous compositions, such as beverages. The liquid nanoemulsion concentrates can be diluted into a medium, for example, an aqueous medium for example, a beverage, to form a liquid dilution composition (e.g. aqueous liquid dilution composition) containing the non-polar compound. Also exemplary of the provided compositions are the liquid dilution compositions containing the non-polar active ingredients, made by diluting the liquid nanoemulsion concentrates in a medium, for example, an aqueous medium, for example, a food or beverage. Exemplary of the liquid dilution compositions are aqueous dilution compositions, for example, clear aqueous compositions containing the non-polar compounds.

The compositions can be made using any non-polar compound. Exemplary of non-polar compounds that can be used in the provided compositions are non-polar active ingredients, for example, pharmaceuticals, nutraceuticals, vitamins and minerals. Exemplary of non-polar active ingredients are Polyunsaturated Fatty Acids (PUFA)-containing compounds, for example, omega-3-containing active ingredients, for example, compounds containing ALA, DHA and/or EPA, for example, oils derived from fish and microalgae, krill and/or flaxseed extract, and omega-6-containing non-polar active ingredients, for example, gamma-linolenic acid (GLA)-containing compounds, for example, borage oil; saw palmetto oil-containing compounds; conjugated fatty acid containing-ingredients, for example, Conjugated Linoleic acid (CLA)-containing compounds; coenzyme Q-containing active ingredients, for example, Coenzyme Q10 (CoQ10), typically oxidized CoQ10 (ubidecarenone)-containing compounds; and compounds containing phytosterols (plant sterols). Additional exemplary non-polar active ingredients are described herein. Any non-polar compound can be used in the provided compositions.

1. Liquid Nanoemulsion Concentrates Containing the Non-Polar Compounds

Exemplary of the provided compositions are liquid nanoemulsion concentrates (also called "concentrates" or "liquid concentrates") containing one or more non-polar compounds. The concentrates can be diluted into aqueous media to form aqueous liquid dilution compositions containing the non-polar compounds. The liquid concentrates are formulated based on one or more desirable properties, for example, clarity; safety; taste; smell; stability, for example, lack of phase separation, "ringing" and/or precipitation over time, and/or bioavailability of the concentrate and/or the aqueous liquid dilution compositions containing the concentrate. In one example, the desirable property is the ability of the provided concentrate to yield a clear or partially clear aqueous liquid dilution composition when it is diluted into aqueous medium, for example, a beverage such as water. In another example, the desirable property relates to the safety of the concentrates and/or the desirability of the concentrates for human consumption, for example, in foods and beverages. In another example, it can be desirable that the concentrate contains less than or equal to a particular concentration of one or more ingredients. In another example, it can be desirable that the concentrate contains greater than or equal to a particular concentration of one or more ingredients.

In addition to the non-polar compounds, the concentrates contain at least one surfactant. Typically, the surfactant has an HLB value between 14 or about 14 and 20 or about 20, for example, 14, 15, 16, 17, 18, 19, 20, about 14, about 15, about 16, about 17, about 18, about 19 or about 20. Exemplary of suitable surfactants are polysorbates, such as polysorbate 80 and other surfactants having HLB values between 14 or about 14 and 20 or about 20. Typically, the surfactant is a natural surfactant, for example, a surfactant that is GRAS (generally recognized as safe) by the FDA and/or Kosher certified.

The liquid concentrates further contain water (e.g. filtered water), typically a high amount of water, for example, water that is between 60% or about 60% and 80% or about 80%, by weight (w/w), of the concentrate.

Typically, the concentrates further contain one or more additional ingredients. Exemplary of additional ingredients that can be included in the concentrates are preservatives, solvents, co-surfactants, emulsion stabilizers, pH adjusters and flavoring agents.

The non-polar compounds in the concentrates and dilution compositions are contained in micelles. These micelles, containing the non-polar compound surrounded by the one or more surfactants, allow dispersion of the non-polar compound among polar solvents, for example, when the concentrates are diluted to form aqueous liquid dilution compositions. The micelles containing the non-polar compounds typically have a small or relatively small particle size, for example, less than 1000 or about 1000 nm, less than 500 or about 500 nm, typically less than 300 or about 300 nm, typically less than 200 or about 200 nm, for example, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 125, 150 or 200 nm. Smaller particle size correlates with clarity of the aqueous liquid dilution compositions containing the diluted concentrates. For example, a liquid with a smaller particle size is more clear than a liquid with a larger particle size. Small particle size also can contribute to other desirable properties, for example, stability.

A number of factors, including ingredients, their relative concentrations, and methods for making the concentrates, affect the particle size of the compositions, and thus to desirable properties of the compositions, for example, clarity. In particular, the nature of the surfactant, particularly the HLB of the surfactant, and the relative concentrations of water, surfactant and the non-polar compound, contribute to small particle size, and the clarity of the aqueous liquid dilution compositions. Typically, several of these parameters and properties are related to one another. For example, several of the parameters contribute to the particle size, typically small particle size, of the compositions. Particle size contributes directly to clarity of the aqueous liquid dilution compositions containing the concentrates. Particle size also can relate to other properties, for example, stability, lack of "ringing" and/or precipitate formation of the aqueous liquid dilution compositions containing the concentrates.

Accordingly, properties of the ingredients and their relative concentrations in the concentrates are important for the ability of the concentrate to yield desirable dilution compositions. Determining the appropriate ingredients, and relative concentrations thereof, that will yield dilution compositions having desirable properties, is performed using provided methods for formulating the liquid concentrates.

a. Formulating the Liquid Concentrates

Using the provided formulation methods, the concentrates are formulated by selecting ingredients and concentration ratios of the ingredients that yield compositions having one or more desired properties. When formulating the concentrates, selected ingredients and starting concentrations are used to make initial concentrates, which are evaluated and modified, if necessary.

As a first step in formulating the provided concentrates, one or more initial concentrate is made and evaluated for desired properties. For this step, ingredients are selected, for example, from one or more of the lists of ingredients provided below. A starting concentration (weight percentage) of each selected ingredient is selected from within the appropriate concentration range for that ingredient or category of ingredient, for example, the appropriate concentration range for the surfactant. In some cases, the initial concentrate is formulated based on the ingredients, and concentrations thereof, of an existing concentrate, having one or more desired properties.

The initial concentrate(s) then is made, using the methods for making the concentrates, provided below, adding each ingredient at its starting concentration at the appropriate step. In one example, more than one initial concentrate is made. For example, multiple initial concentrates, each having a different concentration of one or more ingredients, can be made and compared. For example, multiple initial concentrates can be made in order to test various representative concentrations within an appropriate concentration range for one or more particular ingredient.

In a typical example, the initial concentrate is made by including at least one surfactant, having an HLB value between 14 or about 14 and 20 or about 20 (e.g. polysorbate 80), at a starting concentration within the concentration range of between 16% or about 16% and 30% or about 30%, by weight, of the concentrate; at least one non-polar compound, at a starting concentration within the concentration range of between 5% or about 5% and 10% or about 10%; and water, at a starting concentration of between 60% or about 60% and 80% or about 80%. In one example, the initial concentrate further includes other ingredients, for example, preservative(s), co-surfactant(s), and/or other ingredients.

After making the initial concentrate(s), the concentrate(s) is evaluated for one or more desired properties, for example, the ability to form dilution compositions (e.g. clear dilution compositions or dilution compositions having a particular turbidity value, particle size or other property). The ability to form dilution compositions having one or more properties is assessed by diluting the concentrate in aqueous medium, for example, diluting the concentrate in the aqueous medium at a dilution factor of between 1:10 or about 1:10 and 1:1000 or about 1:1000 or more, typically between 1:10 or about 1:10 and 1:500 or about 1:500 or more, for example, diluted not more than 1:10 or about 1:10, 1:20 or about 1:20, 1:25 or about 1:25, 1:50 or about 1:50, 1:100 or about 1:100, 1:200 or about 1:200, 1:250 or about 1:250, 1:300 or about 1:300, 1:400 or about 1:400, 1:500 or about 1:500, for example, 1:10, 1:20, 1:25, 1:30, 1:35, 1:40, 1:50, 1:55, 1:60, 1:65, 1:70, 1:75, 1:80, 1:90, 1:100, 1:110, 1:120, 1:130, 1:140, 1:150, 1:160, 1:170, 1:180, 1:190, 1:200, 1:210, 1:220, 1:230, 1:235, 1:240, 1:250, 1:260, 1:270, 1:280, 1:290, 1:300, 1:350, 1:400, 1:450, 1:500 or more.

After evaluation, the ingredients, and/or concentrations thereof, can be adjusted in order to generate the desired properties in the final concentrate. Typically, the concentration of the non-polar compound, the surfactant, and/or the water is the concentration that is adjusted after evaluating the initial concentrate. Similarly, when formulating multiple initial concentrates, one or more of the non-polar compound, surfactant and water concentration is/are varied among the multiple initial concentrates. In some cases, following evaluation, it can be determined that additional ingredients (not included in the initial formulation) are needed or desirable for achieving the desired properties of a particular concentrate. This process can be repeated until a concentrate having the desired property or properties is generated.

i. Common Ingredients and Typical Concentration Ranges

Each of the provided concentrates contains at least one compound, typically a non-polar compound. Any non-polar compound can be used with the provided methods and concentrates. Several exemplary non-polar compounds that can be incorporated into the provided compositions are described herein below. Typically, the non-polar compound is a non-polar active ingredient, for example, an oil-based active ingredient, for example, a polyunsaturated fatty acid (PUFA), a coenzyme Q or a phytochemical. For formulating the initial concentrate, the starting concentration of the non-polar compound typically is chosen from within a concentration range of between 5% or about 5% and 10% or about 10% (w/w) of the concentrate. Exemplary starting concentrations of the non-polar compound are 5%, 5.25%, 6%, 7%, 8%, 9%, 10%, about 5%, about 6%, about 7%, about 8%, about 9% or about 10% (w/w) of the concentrate. The non-polar compound typically is added as part of an oil phase, according to the provided methods for making the concentrate.

In addition to the non-polar compound, the concentrates contain at least one surfactant. The surfactant typically is added as part of an oil phase, but can alternatively be added to the water phase. The surfactant has an HLB value of between 14 or about 14 and 20 or about 20, for example, 14, 15, 16, 17, 18, 19 or 20, or about 14, about 15, about 16, about 17, about 18, about 19, about 20, typically between 16 or about 16 and 18 or about 18. Exemplary of suitable surfactants are polysorbate 80 and other surfactants having similar properties, for example, any surfactant having an HLB value between 14 or about 14 and 20 or about 20, such as, but not limited to, polysorbate 80 analogs, e.g. polysorbate 80 homologs, for example, polysorbate 20, polysorbate 40 and polysorbate 60, and other polysorbates.

Surfactants, HLB values, and methods for determining HLB values are well known. Typically, the surfactant is a natural surfactant, which is safe and/or approved for human consumption.

Typically, the starting concentration of the surfactant is chosen from within a concentration range of between 16% or about 16% and 30% or about 30% (w/w), for example, 16%, 17%, 18%, 19%, 20%, 21%, 22%, 23%, 24%, 25%, 26%, 27%, 28%, 29%, 30%, about 16%, about 17%, about 18%, about 19%, about 20%, about 21%, about 22%, about 23%, about 24%, about 25%, about 26%, about 27%, about 28%, about 29% or about 30%, (w/w) of the concentrate. Also exemplary of surfactant concentrations within the appropriate concentration range are 17.75% and 25.2%.

In one example, the concentration range of the surfactant is between 17% or about 17% and 25% or about 25% (w/w) of the concentrate. In another example, the concentration range of the surfactant is between 18% or about 18% and 25% or about 25% (w/w) of the concentrate. In another example, the concentration range of the surfactant is between 18% or about 18% and 20% or about 20% (w/w) of the concentrate. In another example, the concentration range of the surfactant is between 17% or about 17% and 20% or about 20% (w/w) of the concentrate. In another example, the concentration range of the surfactant is between 16% or about 16% and 20% or about 20% (w/w) of the concentrate.

The concentrates further contain water, typically a high concentration of water, as part of the water phase. Typically, the starting concentration of water is chosen from within a concentration range of between 60% or about 60% and 80% or about 80% (w/w) of the concentrate, for example, 60%, 61%, 62%, 63%, 64%, 65%, 66%, 67%, 68%, 69%, 70%, 71%, 72%, 73%, 74%, 75%, 76%, 77%, 78%, 79%, 80%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% (w/w) of the concentrate. Also exemplary of water concentrations falling within the appropriate concentration range of water are 71.74%, 75.8165%, 74.25%, 68.7865% and 68.29% (w/w) of the concentrate. In one example, the concentration range of the water is between 65% or about 65% and 80% or about 80% (w/w) of the concentrate. In one example, the concentration range of the water is between 65% or about 65% and 75% or about 75% (w/w) of the concentrate or between 65% or about 65% and 76% or about 76% (w/w) of the concentrate.

One or more, typically more than one, additional ingredients can be added to the initial concentrate. For example, the concentrates typically contain at least one preservative, typically a natural preservative, for example, benzyl alcohol. Exemplary of other additional ingredients that can be added to the concentrates, including the initial concentrates, are emulsion stabilizers, for example, a blend of gums; a solvent for the non-polar compound, for example, an oil other than the non-polar compound, for example, vitamin E oil or flax seed oil; a pH adjuster, for example, citric acid and/or phosphoric acid; one or more flavoring agents, for example, D-limonene or lemon oil; a co-surfactant, for example, a phospholipid, for example, phosphatidylcholine.

The appropriate concentration ranges for the additional ingredients are described in individual sections below. Typically, the concentration of the additional ingredients depends, in part, on the concentrations of the non-polar active ingredient, the surfactant and the water. Typically, the concentrations of these three ingredients are the focus of the formulating methods. For example, when it is determined that modifications to ingredient concentrations in the initial concentrate should be made, it typically is the concentrations of one or more of these three ingredients that are adjusted.

In one example, it can be desirable to add one or more of the additional ingredients after evaluation of the initial concentrate, for example, in order to improve the concentrate with respect to one or more desired properties.

ii. Evaluation of the Initial Concentrate

After an initial concentrate is made according to the methods provided herein, it is evaluated based on one or more desired properties, for example, properties of an aqueous liquid dilution composition containing the diluted concentrate, for example, clarity, color, smell, taste, safety, stability, "ringing" or forming of precipitates and/or the presence of crystals. Typically, the ability of the initial concentrate to form a clear liquid upon dilution in an aqueous medium is the desired property that is evaluated. In this example, the clarity/turbidity of the diluted aqueous liquid dilution composition containing the initial concentrate is analyzed.

For evaluation of properties of the aqueous liquid dilution composition, the initial concentrate is diluted into an aqueous medium, typically water, for example, at a dilution factor of between 1:10 or about 1:10 and 1:1000 or about 1:1000, typically between 1:10 or about 1:10 and 1:500 or about 1:500, for example, diluted not more than 1:10 or about 1:10, at least 1:20 or about 1:20, at least 1:25 or about 1:25, at least 1:50 or about 1:50, at least 1:100 or about 1:100, at least 1:200 or about 1:200, at least 1:250 or about 1:250, at least 1:300, at least 1:400 or at least 1:500, for example, 1:10, 1:20, 1:25, 1:30, 1:35, 1:40, 1:50, 1:55, 1:60, 1:65, 1:70, 1:75, 1:80, 1:90, 1:100, 1:110, 1:120, 1:130, 1:140, 1:150, 1:160, 1:170, 1:180, 1:190, 1:200, 1:210, 1:220, 1:230, 1:235, 1:240, 1:250, 1:260, 1:270, 1:280, 1:290, 1:300, 1:350, 1:400, 1:450, or 1:500. Typically, clarity of the aqueous liquid dilution composition containing the diluted initial concentrate is evaluated using one or more approaches. Additionally, other properties can be evaluated, for example, smell and/or taste properties of the liquid, for example, when the non-polar compound is a polyunsaturated fatty acid (PUFA), particularly fish oil or algae oil, whether the aqueous liquid dilution composition smells "fishy" may be evaluated empirically.

(1) Clarity

In one example, the provided concentrates have the ability to form clear liquids upon dilution in aqueous medium. To evaluate the clarity of an aqueous liquid dilution composition containing the initial concentrate, one of several approaches can be used. The clarity can be assessed by empirical observation, by measuring particle size and/or by measuring the turbidity value of the liquid.

In one example, the concentrates can be diluted to form clear liquids (or liquids that are equal in clarity to known liquids), by adding between 0.05 grams (g) or about 0.05 g and 10 g or about 10 g of the concentrate, typically between 0.05 g and 5 g, for example, 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1 g, 2 g, 3 g, 4 g, 5 g, 6 g, 7 g, 8 g, 9 g, or 10 g of the concentrate, to 8 fluid ounces, about 8 fluid ounces, or at least 8 fluid ounces or at least about 8 fluid ounces, for example 8, 9, 10, 11, 12, 13, 14, 15, 16, 17, 18, 19, 20, 25, 30, 35, 40, 45, 50, 100, 200 or more fluid ounces, of aqueous medium, for example, water, forming a clear aqueous liquid dilution composition that contains the non-polar compound. In another example, the concentrate can be diluted to form a clear aqueous liquid dilution composition by adding between 1 mL or about 1 mL and 10 mL or about 10 mL of the concentrate, for example, 1 mL, 2 mL, 3 mL, 4 mL, 5 mL, 6 mL, 7 mL, 8 mL, 9 mL or 10 mL of the concentrate to 8 fluid ounces, about 8 fluid ounces, or at least 8 fluid ounces or at least about 8 fluid ounces, for example 8, 9, 10, 11, 12, 13, 14, 15, 16, 17, 18, 19, 20, 25, 30, 35, 40, 45, 50, 100, 200 or more fluid ounces, of aqueous medium, for example, water, forming a clear aqueous liquid dilution composition that contains the non-polar compound.

In another example, the concentrate can be diluted in aqueous medium to form a clear aqueous liquid dilution composition when at least 25 mg or about 25 mg, typically at least 35 mg, for example, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000 mg, or more, of the non-polar active ingredient, is contained in at least 8 fluid ounces or at least about 8 fluid ounces of aqueous liquid dilution composition, for example, a beverage, for example, water.

In another example, the concentrate can be diluted in an aqueous medium to form a clear aqueous liquid dilution composition at a dilution factor of between 1:10 or about 1:10 and 1:1000 or about 1:1000, typically between 1:10 or about 1:10 and 1:500 or about 1:500, for example, when diluted not more than 1:10 or about 1:10, 1:20 or about 1:20, 1:25 or about 1:25, 1:50 or about 1:50, 1:00 or about 1:100, 1:200 or about 1:200, 1:250 or about 1:250, 1:300 or about 1:300, 1:400 or about 1:400, 1:500 or about 1:500, for example, 1:10, 1:20, 1:25, 1:30, 1:35, 1:40, 1:50, 1:55, 1:60, 1:65, 1:70, 1:75, 1:80, 1:90, 1:100, 1:110, 1:120, 1:130, 1:140, 1:150, 1:160, 1:170, 1:180, 1:190, 1:200, 1:210, 1:220, 1:230, 1:235, 1:240, 1:250, 1:260, 1:270, 1:280, 1:290, 1:300, 1:350, 1:400, 1:450, 1:500 or more. In another example, the clear liquid is formed at dilutions less dilute than 1:10 of the concentrate.

The provided liquid nanoemulsion concentrates can be formulated using any non-polar compound for dilution in an aqueous medium. In one example, the concentrates can be diluted in aqueous medium, for example, over a wide dilution range to form clear liquids, for example, at a dilution factor of between 1:10 or about 1:10 and 1:1000 or about 1:1000, typically between 1:10 or about 1:10 and 1:500 or about 1:500, for example, when diluted not more than 1:10 or about 1:10, 1:20 or about 1:20, 1:25 or about 1:25, 1:50 or about 1:50, 1:100 or about 1:100, 1:200 or about 1:200, 1:250 or about 1:250, 1:300 or about 1:300, 1:400 or about 1:400, 1:500 or about 1:500, for example, 1:10, 1:20, 1:25, 1:30, 1:35, 1:40, 1:50, 1:55, 1:60, 1:65, 1:70, 1:75, 1:80, 1:90, 1:100, 1:110, 1:120, 1:130, 1:140, 1:150, 1:160, 1:170, 1:180, 1:190, 1:200, 1:210, 1:220, 1:230, 1:235, 1:240, 1:250, 1:260, 1:270, 1:280, 1:290, 1:300, 1:350, 1:400, 1:450, 1:500 or more. Typically, the clarity of the liquid is maintained with increasing dilutions, for example, to infinity.

Clarity of the aqueous liquid dilution composition can be evaluated using one of several different approaches, for example, qualitatively, by empirical evaluation, or quantitatively, by measuring particle size and/or by measuring the turbidity value of the liquid. In some examples, a particular quantitative or qualitative clarity value is desired. In another example, it can be desired that the aqueous liquid dilution composition is as clear as, less clear or more clear than another liquid, for example, an aqueous liquid dilution composition made according to the provided methods or a beverage, for example, a beverage that does not contain the concentrate. For example, an aqueous liquid dilution composition, containing the liquid concentrate diluted in a beverage, may be as clear or about as clear as the same beverage, containing no concentrate. Either type of evaluation can be done qualitatively, for example by empirical observation, or quantitatively, for example, by calculating particle size and/or turbidity value (NTU) for the liquid(s).

(a) Empirical Evaluation

The relative clarity/turbidity of the aqueous liquid dilution composition containing the diluted initial concentrate can be assessed qualitatively by observation. In one example, a clear liquid is considered clear if it does not have a cloudy appearance and/or if no particles are visible when looking at the liquid with the naked eye. Clarity can be assessed empirically by comparison to other liquids, for example, water, fruit juice, soda and/or milk.

In some cases, it is desirable that the liquid be as clear or about as clear as water or another liquid, for example a beverage. For example, it can be desired that the liquid (containing the liquid concentrate diluted in an aqueous medium, for example, a beverage) is as clear or about as clear as the aqueous medium not containing the liquid concentrate. In a related example, it can be desired that there is no substantial difference, for example, no observable difference, between the aqueous liquid dilution composition containing the concentrate and the aqueous medium without the concentrate. A clear liquid is not necessarily colorless, for example, a yellow liquid that contains no visible particles or cloudiness can be considered clear.

(b) Particle Size

Alternatively, the clarity of the aqueous liquid dilution composition containing the diluted initial concentrate can be assessed by measuring the particle size of the liquid. Methods for measuring particle size are known. Any method for measuring particle size can be used if it is able to measure particle sizes in the appropriate ranges as described below.

For example, particle size analysis is available commercially, for example, from Delta Analytical Instruments, Inc. In one example, the particle size is measured, for example, by Delta Analytical Instruments, Inc., using a light-scattering analyzer, for example, a dynamic light scattering analyzer, for example, the Horiba® LB-550, which can measure particle sizes within a range of 0.001 micron to 6 micron and uses a Fourier-Transform/Iterative Deconvolution technique for reporting data and can measure sample concentrations from ppm to 40% solids; the Horiba® LA-920, which is a laser light-scattering instrument having an He—Ne laser and a tungsten lamp and can determine particle sizes from 0.02 micron to 2000 micron using Mie Theory; or other analyzers available from Delta Analytical Instruments, Inc.

Alternatively, the particle size can be measured microscopically, for example, by viewing the liquid under a microscope, for example, at 640× magnification. Using this method, particle size can be quantified by comparing to a measuring device, for example, a ruler, which is visible when viewing the liquid under the microscope. If any particles are observable at this magnification, they are measured by comparison to the measuring device. At a magnification of 640×, for example, any particle that is about 25 nm, 25 nm, or greater than 25 nm are visible. Particle sizes smaller than 25 nm are not visible at this magnification.

Typically, it is desired that the aqueous liquid dilution compositions have a particle size less than 200 nm or less than about 200 nm, for example, 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. Typically, it is desired that the aqueous liquid dilution compositions have a particle size less than 100 nm or about 100 nm, less than 50 nm or about 50 nm, or less than 25 nm or about 25 nm. Typically, the particle size of the aqueous liquid dilution composition containing the concentrate is between 5 nm or about 5 nm and 200 nm or about 200 nm, typically between 5 nm or about 5 nm and 50 nm or about 50 nm.

(c) Turbidity Measurement

Alternatively, clarity of the liquid can be analyzed by taking an optical turbidity measurements, which indicates the level of cloudiness or haziness of a liquid, which correlates to size/number of particles in suspension in the liquid. The more clear a particular liquid, the lower its turbidity value.

Turbidity can measured optically, for example, by using a nephelometer, an instrument with a light and a detector. The nephelometer measures turbidity by detecting scattered light resulting from exposure of the liquid to an incident light. The amount of scattered light correlates to the amount of particulate matter in the liquid. For example, a beam of light will pass through a sample with low turbidity with little disturbance. Other methods for measuring turbidity are well known and can be used with the provided methods and compositions.

The units of a turbidity value measured with a nephelometer are Nephelometric Turbidity Units (NTU). In one example, it is desired that the aqueous liquid dilution composition containing the diluted concentrate has low turbidity, for example, a turbidity value (NTU) of 30 or about 30; or an NTU value of less than 30 or about 30, for example, less than 29 or about 29, less than 28 or about 28, less than 27 or about 27, less than 26 or about 26, less than 25 or about 25, less than 24 or about 24, less than 23 or about 23, less than 22 or about 22, less than 21 or about 21, less than 20 or about 20, less than 19 or about 19, less than 18 or about 18, less than 17 or about 17, less than 16 or about 16, less than 15 or about 15, less than 14 or about 14, less than 13 or about 13, less than 12 or about 12, less than 11 or about 11, less than 10 or about 10, less than 9 or about 9, less than 8 or about 8, less than 7 or about 7, less than 6 or about 6, less than 5 or about 5, less than 4 or about 4, less than 3 or about 3, less than 2 or about 2, less than 1 or about 1; or 29 or about 29, 28 or about 28, 27 or about 27, 26 or about 26, 25 or about 25, 24 or about 24, 23 or about 23, 22 or about 22, 21 or about 21, 20 or about 20, 19 or about 19, 18 or about 18, 17 or about 17, 16 or about 16, 15 or about 15, 14 or about 14, 13 or about 13, 12 or about 12, 11 or about 11, 10 or about 10, 9 or about 9, 8 or about 8, 7 or about 7, 6 or about 6, 5 or about 5, 4 or about 4, 3 or about 3, 2 or about 2, 1 or about 1, or 0 or about 0. In another example, the turbidity value of the aqueous liquid dilution composition is less than 200 or less than about 200, for example, 200, 175, 150, 100, 50, 25 or less.

In another example, it is desirable that the aqueous liquid dilution composition contains a turbidity value that is comparable, for example, about the same as, the same as, or less than or greater than, the turbidity value of another liquid, for example, a beverage not containing the liquid concentrate or an aqueous liquid dilution composition made by the provided methods.

iii. Selecting a Formulation and Modifying Formulations

After evaluation of the initial concentrate(s), either a particular formula is chosen or one or more modifications is made to the initial concentrate formula based on the results of the evaluation. When an initial concentrate does not display one or more desired properties, based on the evaluation, the concentration of one or more ingredients can be adjusted and another initial concentrate made, in order to repeat the process until a concentrate with the desired properties is made. Alternatively, alternative ingredients can be chosen. In one example, modification of the initial concentrate involves the addition of one or more additional ingredients. For example, if evaluation reveals that the oil and water phases of the concentrate or aqueous liquid dilution composition containing the diluted concentrate are separating, an emulsion stabilizer can be added to the formulation. In another example, a co-surfactant can be added to help emulsify the components of the concentrate. In another example, the phase (oil phase or water phase), to which a particular ingredient is added, is modified. For example, the formulation can be modified so that the surfactant is added to the oil phase instead of the water phase according to the provided methods.

In one example, when evaluation of the initial concentrate reveals that it has desired properties, no modifications are made. In this example, the formula of the initial concentrate is used for making the concentrate. When two or more initial concentrates are made, for example, with increasing concentrations of an ingredient, the formula of one of the initial concentrates can be chosen. Which formula is chosen can be based on which formula has the most desirable property. Alternatively, desirable properties can be balanced with relative amounts of ingredients. In one example, it is desirable to choose the formulation that uses the lowest or the highest concentration of a particular ingredient but still provides a concentrate that yields a clear liquid upon dilution in an aqueous medium. In one example, the desired formulation is the formulation that has the lowest concentration of the surfactant, while still providing a concentrate that yields a clear liquid upon dilution in an aqueous medium. In another example, the desired formulation is the formulation that has the highest concentration of the non-polar active ingredient, while still providing a concentrate that yields a clear liquid upon dilution into an aqueous medium. In another example, the formulation that yields the clearest liquid is desired.

In another example, however, modifications are made to the formula even if the initial concentrate bears desired properties. For example, upon determining that a particular concentrate formulation results in desired properties, it may be desirable to modify the concentration of one or more ingredients to determine whether the same desired properties can be achieved if a higher or lower concentration of the ingredient(s) is used. For example, it can be desirable to determine the lowest concentration of surfactant that can be used, while still generating a concentrate with a desired property, for example, the ability to form a clear liquid upon dilution in an aqueous medium. In another example, it can be desirable to determine the highest concentration of the non-polar ingredient that can be incorporated into a concentrate, while still maintaining the desired property, for example, the ability of the concentrate to form a clear liquid upon dilution in an aqueous medium. In another example, one or more additional ingredients may be added after making an initial concentrate with desirable properties, for example, flavoring agents and/or pH adjusting agents.

b. Non-Polar Compounds

The concentrates contain one or more non-polar compounds. Non-polar compounds include any lipophilic or lipid soluble compounds, for example, active ingredients, that have greater solubility in organic solvents (e.g. ethanol, methanol, ethyl ether, acetone, and benzene) and in fats and oils, than in aqueous liquid dilution compositions, for example, water. Typically, the non-polar compounds used in the provided compositions are poorly water soluble, for example, water insoluble or compounds having low water solubility. Non-polar compounds include drugs, hormones, vitamins, nutrients and other lipophilic compounds. The non-polar compounds include drugs, hormones, vitamins, nutrients and other lipophilic compounds. Exemplary non-polar compounds are listed hereinbelow. The provided methods can be used to make concentrates that can be diluted (e.g. dissolved/dispersed) in aqueous medium, using any non-polar compound. In one example, the non-polar compound is not a polysorbate, e.g. is not polysorbate 80.

Exemplary of non-polar compounds that can be used in the provided concentrates are:

Non-polar ingredients containing essential fatty acids, for example, polyunsaturated fatty acids (PUFAs), for example, gamma-linolenic acid (GLA), for example, borage oil and evening primrose (*Oenothera biennis*) oil, blackcurrant seed oil, hemp seed oil, and spirulina extract; compounds containing omega-3 fatty acids, for example, natural and synthetic omega-3 fatty acids, for example, compounds containing omega-3 polyunsaturated long-chain fatty acids, including Eicosapentaenoic acid (EPA) (20:5ω3); Docosahexaenoic acid (DHA) (22:6ω3); Eicosatetraenoic acid (24:4ω3); Docosapentaenoic acid (DPA, Clupanodonic acid) (22:5ω3); 16:3 ω3; 24:5 ω3 and/or nisinic acid (24:6ω3), for example, fish oil, algae oil, krill oil, canola oil, flaxseed oil, soybean oil and walnut oil; compounds containing short-chain omega-3 fatty acids, for example, Alpha-Linolenic acid (α-Linolenic acid; ALA) (18:3ω3) and Stearidonic acid (18:4ω3), esters of an omega-3 fatty acid and glycerol, for example, monoglycerides, diglycerides and triglycerides, esters of omega-3 fatty acid and a primary alcohol, for example, fatty acid methyl esters and fatty acid esters, precursors of omega-3 fatty acid oils, for example, EPA precursor, DHA precursor, derivatives such as polyglycolized derivatives or polyoxyethylene derivatives, oils containing the omega-3 fatty acids, for example, fish oil (marine oil), for example, highly purified fish oil concentrates, perilla oil, krill oil, and algae oil, for example, microalgae oil; compounds containing omega 6 fatty acids, for example, compounds containing Linoleic acid (18:2ω6) (a short-chain fatty acid); Gamma-linolenic acid (GLA) (18:3ω6); Dihomo gamma linolenic acid (DGLA) (20:3ω6); Eicosadienoic acid (20:2ω6); Arachidonic acid (AA) (20:4ω6); Docosadienoic acid (22:2ω6); Adrenic acid (22:4ω6); and/or Docosapentaenoic acid (22:5ω6), for example, borage oil, corn oil, cottonseed oil, grapeseed oil, peanut oil, primrose oil, for example, evening primrose *Oenothera biennis*) oil, blackcurrant seed oil, hemp seed oil, spirulina extract, safflower oil, sesame oil and soybean oil;

Other fatty acids, for example, triglycerides, including medium chain triglycerides, polar lipids, for example, ether lipids, phosphoric acid, choline, fatty acids, glycerol, glycolipids, triglycerides, and phospholipids (e.g., phosphatidylcholine (lecithin), phosphatidylethanolamine, and phosphatidylinositol); saw palmetto extract; and ethyl linoleate; and herb oils, for example, garlic oils and scordinin; short-chain saturated fatty acids (4:0-10:0), Lauric acid (12:0), Myristic acid (14:0), Pentadecanoic acid (15:0), Palmitic acid (16:0), Palmitoleic acid (16:1 ω7), Heptadecanoic acid (17:0), Stearic acid (18:0), Oleic acid (18:1 ω9), Arachidic acid (20:0);

Micronutrients, for example, vitamins, minerals, co-factors, for example, Coenzyme Q10 (CoQ10, also called ubiquinone), ubiquinol, tumeric extract (cucuminoids), saw palmetto lipid extract (saw palmetto oil) echinacea extract, hawthorn berry extract, ginseng extract, lipoic acid (thiotic acid), ascorbyl palmitate, kava extract, St. John's Wort (hypericum, Klamath weed, goat weed), extract of quercitin, dihydrocpiandrosterone, indol-3-carbinol;

Carotenoids, including hydrocarbons and oxygenated, alcoholic derivatives of hydrocarbons, for example, beta carotene, mixed carotenoids complex, lutein, lycopene, Zeaxanthin, Cryptoxanthin, for example, beta-crytoxanthin, beta carotene, mixed carotenoids complex, astaxanthin, bixin, canthaxanthin, capsanthin, capsorubin, apo-carotenal, beta-12'-apo-carotenal, "Carotene" (mixture of alpha and beta-carotene), gamma carotene, ciolerythrin, zeaxanthin, esters of hydroxyl- or carboxyl-containing members thereof;

Fat-soluble vitamins, for example, Vitamins A, D, E and K, and corresponding provitamins and vitamin derivatives such as esters with an action resembling that of vitamin A, D, E or K for example; retinol (vitamin A) and pharmaceutically acceptable derivatives thereof, for example, palmitate ester of retinol and other esters of retinol, and calciferol (vitamin D) and its pharmaceutically acceptable derivatives thereof and precursors of vitamin D, d-alpha tocopherol (vitamin E) and derivatives thereof, including pharmaceutical derivatives thereof, for example, Tocotrienols, d-alpha tocopherol acetate and other esters of d-alpha tocopherol, and ascorbyl palmitate, a fat-soluble version of vitamin C;

Phytochemicals, including phytoestrogens, for example, genistein and daidzein, for example, isoflavones, for example, soy isoflavones, flavonoids, phytoalexins, for example, Resveratrol (3,5,4'-trihydroxystilbene), red clover extract, and phytosterols;

Lipid-soluble drugs, including natural and synthetic forms of immunosuppressive drugs, such as Cyclosporin, protease inhibitors such as Ritonavir, macrolide antibiotics and oil soluble anesthetics such as Propofol, natural and synthetic forms of steroidal hormones, for example, estrogens, estradiols, progesterone, testosterone, cortisone, phytoestrogens, dehydroepiandrosterone (DHEA), growth hormones and other hormones;

Oil-soluble acids and alcohols, for example, tartaric acid, lactylic acid butylated hydroxyanisole, butylated hydroxytoluene, lignin, sterols, polyphenolic compounds, oryzanol, cholesterol, phytosterols, flavonoids, such as quercetin and reservatol and diallyl disulfides.

i. Polyunsaturated Fatty Acid (PUFA)-Containing Active Ingredients

Exemplary of the non-polar compounds contained in the concentrates are compounds containing fatty acids, for example, active ingredients containing polyunsaturated fatty acids (PUFAs). Fatty acids are straight-chain hydrocarbon molecules with a carboxyl (COOH) group at one end of the chain. PUFAs are fatty acids that contain more than one carbon-carbon double bond in the carbon chain of the fatty acid. PUFAs, particularly essential fatty acids, are useful as dietary supplements.

Different nomenclatures can be used to describe fatty acid molecules. Lipid nomenclature, for example, 18:3 ω-3, indicates the carbon chain length, number of double bonds and the position along the carbon chain of the first carbon-carbon double bond in a fatty acid. Using this nomenclature, each carbon along the chain is labeled according to its position relative to one end of the chain. For example, the first carbon away from the carboxylate end is named α, the second is named β, and so forth. The last carbon in the molecule (furthest from the carboxy group) always is labeled ω (or omega, or n). The number of carbons and the number of double bonds are listed first in the lipid name of a fatty acid, separated by a colon. For example, the name "18:3" indicates that the molecule has eighteen (18) carbons and three (3) double bonds. Following these numbers, the position at which the first double bond appears, relative to the last (ω) carbon, is listed. For example, the nomenclature, 18:3 ω-3 (or 18:3 omega-3; or 18:3 n-3), describes a fatty acid with eighteen (18) carbons and three (3) double bonds, the first of which occurs at the third carbon away from the omega carbon.

Alternatively, chemical nomenclature can be used. The chemical name of a fatty acid describes the position of each double bond. In the chemical naming, the carbons are numbered, beginning with 1, starting with the carbon that is part of the carboxy (COOH) group. Thus, with this numbering system, the α carbon is labeled "2." The chemical name of the fatty acid lists the first carbon (from the COOH end) to participate in each double bond.

Certain PUFAs are called essential fatty acids because mammals, including humans, cannot synthesize them using any known chemical pathway, and must obtain them from diet or by supplementation. (U.S. Pat. No. 6,870,077; Covington, *American Family Physician* (2004), 70(1): 133-140). The essential PUFAs are the omega-3 (ω3; n-3) fatty acids and the omega-6 (ω-6; n-6) fatty acids. Both omega-3 and omega-6 fatty acids are methylene interrupted polyenes, which have two or more cis double bonds, separated by a single methylene group. Exemplary of Omega-3 fatty acids are Alpha-Linolenic acid (α-Linolenic acid; ALA) (18:3ω3) (a short-chain fatty acid); Stearidonic acid (18:4ω3) (a short-chain fatty acid); Eicosapentaenoic acid (EPA) (20:5ω3); Docosahexaenoic acid (DHA) (22:6ω3); Eicosatetraenoic acid (24:4ω3); Docosapentaenoic acid (DPA, Clupanodonic acid) (22:5ω3); 16:3 ω3; 24:5 ω3 and nisinic acid (24:6ω3). Longer chain Omega-3 fatty acids can be synthesized from ALA (the short-chain omega-3 fatty acid). Exemplary of Omega-6 fatty acids are Linoleic acid (18:2ω6) (a short-chain fatty acid); Gamma-linolenic acid (GLA) (18:3ω6); Dihomo gamma linolenic acid (DGLA) (20:3ω6); Eicosadienoic acid (20:2ω6); Arachidonic acid (AA) (20:4ω6); Docosadienoic acid (22:2ω6); Adrenic acid (22:4ω6); and Docosapentaenoic acid (22:5ω6).

While the longer chain Omega-3 and Omega-6 essential fatty acids can be synthesized from ALA (the short-chain omega-3 fatty acid) and Linolenic acid (LA), respectively, evidence suggests that conversion of these short chain fatty acids in humans is slow. Thus, a major source of long chain essential PUFAs is dietary (see, e.g., Ross et. al, *Lipids in Health and Disease* (2007), 6:21; Lands, *The FASEB Journal* (1992), 6(8): 2530). Dietary supplements containing PUFAs, particularly essential PUFAs, are desirable for protection against cardiovascular disease, inflammation and mental illnesses (see, e.g., Ross et. al, *Lipids in Health and Disease* (2007), 6:21; Lands, *The FASEB Journal* (1992), 6(8): 2530; U.S. Pat. No. 6,870,077). Evidence suggests that essential fatty acids, particularly EPA and DHA, in the form of food and nutritional supplements, play a role in preventing a number of disease states, including cardiovascular diseases, inflammation, mental health and behavioral diseases and disorders (see, e.g., Ross et. al, Lipids in Health and Disease (2007), 6:21; Lands, The FASEB Journal (1992), 6(8): 2530; U.S. Pat. No. 6,870,077; Covington, *American Family Physician* (2004), 70(1): 133-140).

Omega-9 fatty acids are non-essential PUFAs. Exemplary of omega-9 fatty acids are Oleic acid (which is monounsaturated) (18:1 ω9); Eicosenoic acid (20:1 ω9); Mead acid (20:3 ω9); Erucic acid (22:1 ω9); and Nervonic acid (24:1 ω9).

Conjugated fatty acids are PUFAs with two or more conjugated double bonds. Conjugated fatty acids can be used as nutritional supplements. Exemplary of conjugated fatty acids are Conjugated Linoleic acid (CLA), for example, 18:2 ω7, 18:2 ω6; Conjugated Linolenic acid, for example, 18:3ω6, 18:3ω5; and other conjugated fatty acids, for example, 18:3 ω3, 18:4 ω3, and 20:5 ω6.

(1) Omega-3 Fatty Acid Compounds

Exemplary of the PUFA-containing active ingredients that can be used in the provided compositions are compounds that contain one or more omega-3 (ω3; n-3) fatty acids, for example, compounds containing DHA and/or EPA fatty acids, for example, marine oils for example, fish oil, krill oil and algae oil; and compounds containing ALA fatty acids, for example, flax seed oil.

Typically, oils and aqueous compositions containing long-chained polyunsaturated fatty acids (PUFA) are susceptible to oxidation, making them unstable and giving them an unpleasant taste. The ingredients and relative concentrations thereof, as well as the methods for making the concentrates, contribute to desirable properties of DHA/EPA-containing concentrates. In one example, ingredients and methods minimize the "fishy" odor and/or taste of DHA/EPA compositions and increase their stability over time. In one aspect, the compounds in the concentrates have low oxidation, contributing to these desirable properties.

(a) DHA/EPA

Exemplary of non-polar active ingredients that contain one or more omega-3 fatty acids, which can be used in the provided compositions, are compounds containing DHA and/or EPA, for example, marine oil, for example, fish oil, krill oil and algae oil. Any oil containing DHA and/or EPA can be used. In one example, the non-polar active ingredient contains between 20% or about 20% and 40% or about 40% DHA. In another example, the non-polar active ingredient contains between 25% or about 25% and 35% or about 35% DHA. In another example, the non-polar active ingredient contains at least 70% or about 70%, by weight, DHA, for example, at least 75% or about 75%, at least 80% or about 80%, at least 85% or about 85%, or at least 90% or about 90%, by weight, DHA. In another example, the non-polar active ingredient contains between 5% or about 5% and 15% or about 15% EPA, for example, 5, 6, 7, 8, 9, 10, 11, 12, 13, 14 or 15%, by weight, EPA. In another example, the non-polar active ingredient comprises not more than 10% or about 10% EPA or less than 10% or about 10%, EPA. In another example, the non-polar active ingredient contains DHA and EPA, for example, DHA representing at least 20% or about 20%, by weight of the non-polar active ingredient and EPA representing not more than 13% or about 13% of the non-polar active ingredient, for example, not more than 10% or about 10%, by weight of the non-polar active ingredient. In another example, the non-polar active ingredient contains DHA, representing at least 35% or about 35% of the non-polar active ingredient and EPA representing not more than 13% or about 13% of the non-polar active ingredient, for example, not more than 10% or about 10% of the non-polar active ingredient. In another example, the non-polar active ingredient contains DHA and EPA, for example, DHA representing at least 70% or about 70% of the non-polar active ingredient and EPA representing not more than 13% or about 13% of the non-polar active ingredient, for example, not more than 10% or about 10% of the non-polar active ingredient.

(b) Fish Oils

Exemplary of the PUFA-containing non-polar active ingredients that can be used in the provided compositions are oils derived from fish, which contain DHA, EPA or DHA and EPA. Particularly, cold water marine fish are a known source of Omega-3 fatty acids (U.S. Pat. No. 4,670,285). Suitable fish oil containing DHA, EPA or DHA and EPA can be obtained from any of a number of commercial sources, for example, fish oils available from Jedwards International, Inc., any of which can be used with the provided compositions.

Fish oils typically are extracted from fish tissue, for example, frozen fish tissue. In one example, the fish oil is a tasteless fish oil, for example, a cod liver oil, which has been isolated from fish, for example, from cod liver, and then refined and deodorized, or in some other way treated so its taste becomes neutral, for example, as described in International Publication Nos. WO 00/23545 and WO 2004/098311. In one example, these fish oils are isolated from frozen fish tissue by a process that minimizes oxidation. Exemplary of such a tasteless fish oil is Denomega™ 100, Borregaard Ingredients, Sarpsborg, Norway; distributed by Denomega Nutritional Oils AS, Boulder, Colo. Typically, the tasteless fish oil, for example, cod liver oil, contains between 25% or about 25% and 35% or about 35% Omega-3 fatty acids, for example, 34% Omega-3 fatty acids. In one example, the fish oil, for example, the Denomega™ 100 oil, contains 13% or about 13% DHA and 13% or about 13% EPA.

Also exemplary of the fish oils that can be included in the provided compositions are fish oils containing high amounts of Omega-3 fatty acids, for example, high amounts of DHA. One example of such a fish oil contains at least about 85% DHA, typically greater than 85% DHA and at least about 90% Omega-3 fatty acids, typically greater than, 90% Omega-3 fatty acids. In another example, the fish oil can contain 98% PUFA, 89% Omega-3 fatty acids, about 70% DHA, about 10% EPA, 8.9% Omega-6 fatty acids and 0.7% Omega-9 fatty acids.

Exemplary of a fish oil containing high amounts of Omega-3 fatty acids that can used as the non-polar compound in the provided compositions is an Omega-3 Fish Oil EE (O3C Nutraceuticals, supplied by Jedwards International Inc., Quincy, Mass.), which contains 89% Omega-3 fatty acids, 8.9% Omega-6 fatty acids, 0.7% Omega-9 fatty acids, 0.1% saturated fatty acids, 1.0% monounsaturated fatty acids, 74.5% Docosahexanoic (DHA) fatty acids, 9.3% Eicosapentaenoic (EPA) fatty acids and 98% polyunsaturated fatty acids (PUFA). This fish oil also contains 0.1% (16:0) palmitic acid, 0.1% (16:1 ω7) palmitoleic acid, 0.1% (18:0) stearic acid, 0.6% (18:1 ω9) oleic acid, 0.1% (18:1 ω7) oleic acid, 0.3% (18:2 ω6) linoleic acid, 0.2% (18:3 ω3) linolenic acid, 0.2% (18:4 ω3) octadecatetraenoic acid, 0.1% (20:1 ω9) eicosanoic acid, 0.1% (20:2 ω6) eicosadienoic acid, 0.2% (20:3 ω6) Eicosatrienoic Acid, 2.4% (20:4 ω6) arachidonic acid, 0.6% (20:4 ω3) arachidonic acid, 0.1% (22:1 ω11) erucic acid, 0.6% (21:5 ω3) uncosapentaenoic acid, 0.5% (22:4 ω6) docosatetraenoic acid, 5.4% (22:5 ω6) docosapentaenoic acid, 3.6% (22:5 ω3) docosapentaenoic acid and 0.9% other fatty acids.

Also exemplary of a fish oil containing high amounts of Omega-3 fatty acids that can be used in the provided compositions is Omega Concentrate 85 DHA TG Ultra (O3C Nutraceuticals AS, Oslo, Norway), which contains greater than 85% DHA (C22:6n-3) and greater than 90% total omega-3 fatty acids and is isolated from fatty fish species Eugraulidae, Clupeidae and Scombridae families. This fish oil is produced by purifying and concentrating the oils from these fish with gentle technologies to increase the concentration of omega-3 fatty acid DHA. Any fish oil containing DHA and/or EPA can be used as the non-polar compound in the provided compositions. Also exemplary of the fish oils are other fish oils made by O3C Nutraceuticals, AS and other fish oils supplied by Jedwards, International, Inc.

Also exemplary of the fish oils are krill oils, made according to International Publication No. WO 2007/080515.

(c) Algae Oil

Also exemplary of non-polar compounds containing Omega-3 PUFAs, particularly DHA (and optionally EPA), that can be used as the non-polar compound in the provided compositions are oils derived from microorganisms, for example, oils derived from marine dinoflagellates, for example, microalgae, for example, *Crypthecodinium sp*, particularly, *Crypthecodinium cohnii*. Microalgae oils, like fish oil, are an excellent source of omega-3 fatty acids, particularly DHA (U.S. Pat. Nos. 5,397,591, 5,407,957, 5,492,938 and 5,711,983). Exemplary of oils derived from microalgae are the oils disclosed in (and oils made according to the methods described in) U.S. Pat. Nos. 5,397,591, 5,407,957, 5,492,938 and 5,711,983 and U.S. Patent Publication No. 2007/0166411, including DHASCO® and DHASCO-S® (Martek Biosciences Corporation).

For example, U.S. Pat. No. 5,397,591 describes, inter alia, single cell edible oils (algae oils) (and methods for making the oils), which contain at least 70% triglycerides, which contain about 20-35% DHA and lack EPA, isolated from *Crypthecodinium cohnii*, preferably containing more than 70% triglycerides, having 15-20% myristic acid; 20-25% palmitic acid; 10-15% oleic acid; 30-40% DHA and 0-10% other triglycerides. U.S. Pat. No. 5,407,957 describes, inter alia, algae oils (and methods for making the oils) derived from *Crypthecodinium cohnii*, preferably containing greater than about 90% triglycerides, at least 35% DHA by weight, in one example, having 15-20% myristic acid, 20-25% palmitic acid, 10-15% oleic acid, 40-45% DHA, and 0-5% other oils. U.S. Pat. No. 5,492,938 describes, inter alia, single cell edible oils (and methods for making the oils) containing at least 70% triglycerides, which contain about 20-35% DHA and lack EPA, isolated from *Crypthecodinium cohnii*; in one example containing more than 70% triglycerides, having 15-20% myristic acid; 20-25% palmitic acid; 10-1 5% oleic acid; 30-40% DHA; 0-10% other triglycerides. U.S. Pat. No. 5,711,983 describes, inter alia, single cell edible oils (and methods for making the oils) containing at least 70% triglycerides, which contain about 20-35% DHA and lack EPA, isolated from *Crypthecodinium cohnii*; in one example, containing more than 70% triglycerides, having 15-20% myristic acid; 20-25% palmitic acid; 10-15% oleic acid; 30-40% DHA and 0-10% other triglycerides.

Also exemplary of suitable microalgae oils are those disclosed, for example, in U.S. Pat. No. 6,977,166 and U.S. Patent Publication No. 2004/0072330. Any oil derived from dinoflagellate, for example, microalgae, which contains DHA, and optionally EPA, is suitable as an algae oil for use with the provided compositions, for example, V-Pure algae oil (Water4Life, Switzerland, which contains EPA and DHA).

(d) Flax Seed Oil—Omega 3 (ALA)

Also exemplary of the Omega-3 containing non-polar compounds used in the provided compositions is flaxseed oil (flaxseed oil, linseed oil). Flaxseed oils, which are good sources of omega-3 fatty acids, particularly alpha-linolenic acid, have been used as nutritional supplements. Flaxseed oils are produced by pressing the flax seed and refining the oil from the flax seeds. Exemplary of flaxseed oil that can be used as the non-polar compound in the provided compositions is flaxseed oil derived from *Linum usitatissimum* L., for example, flaxseed oil supplied by Sanmark LLC, Greensboro, N.C. (Sanmark Limited, Dalian, Liaoning Province, China), which contains not less than (NLT) 50% C18:3 alpha-linolenic acid, and further contains other fatty acids, for example, 3-8% C16:0 Palmitic acid, 2-8% C18:0 Stearic acid, 11-24% C18:1 Oleic acid, 11-24% C18:2 linoleic acid and 0-3% other fatty acids. Also exemplary of suitable flaxseed oil is a flaxseed oil containing 6% Palmitic acid, 2.5% stearic acid, 0.5% arachidic acid, 19% oleic acid, 24.1% linoleic acid, 47.4 linolenic acid, and 0.5% other fatty acids. The fatty acid composition of flaxseed oil can vary. Any flaxseed oil can be used as the non-polar compound in the provided compositions. In one example, the flaxseed oil contains at least 50% alpha-linolenic acid or at least about 50% alpha-linolenic acid. In another example, the flaxseed oil contains at least 65 or 70% alpha-linolenic acid or at least about 65 or about 70% alpha-linolenic acid. Exemplary of a flaxseed containing greater than 65% linolenic acid content (of total fatty acid content), for example, 70-80% or 70-75%, is the flaxseed described in U.S. Pat. No. 6,870,077.

(2) Omega-6 Compounds

Also exemplary of the non-polar compounds used in the provided compositions are compounds containing omega-6 PUFAs, for example, gamma-linolenic acid (GLA), for example, borage oil and evening primrose (*Oenothera biennis*) oil, blackcurrant seed oil, hemp seed oil, fungal oil and spirulina extract. Any oil containing omega-6 fatty acids can be used in the provided compositions.

(a) Borage Oil (Gamma-Linolenic Acid (GLA))

Exemplary of the omega-6 containing non-polar compounds are compounds containing GLA, for example, borage oil. GLA is an omega-6 PUFA, which primarily is derived from vegetable oils, for example, evening primrose (*Oenothera biennis*) oil, blackcurrant seed oil, hemp seed oil, and spirulina extract. GLA has been used as a nutritional supplement. It has been proposed that GLA has a role in treating various chronic diseases and in particular that it has anti-inflammatory effects (Fan and Chapkin *The Journal of Nutrition* (1998), 1411-1414). In one example, the non-polar active ingredient contains at least about 22% or about 22%, by weight, GLA, for example, 22, 23, 24, 25, 26, 27, 28, 29, 30, 31, 32, 33, 34, 35, 36, 37, 38, 39, 40, 50, 60, or more, %, by weight, GLA.

Borage (*Borago officinalis*), also known as "starflower" is an herb with seeds containing high amounts of GLA. Exemplary of borage oil that is used as a non-polar active ingredient in the provided compositions is the borage oil supplied by Sanmark LLC, Greensboro, N.C. (Sanmark Limited, Dalian, Liaoning Province, China), derived by pressing and isolating oil from the seeds of *Borago officinalis* L. This oil contains not less than (NLT) 22% C18:3 gamma-linolenic acid (GLA), between 9 and 12% C16:0 Palmitic acid, between 3 and 5% C18:0 Stearic acid, between 15 and 20% C18:1 Oleic acid, between 35 and 42% C18:2 linoleic acid, between 3 and 5% C20:1 Ocosenoic acid, between 1 and 4% C22:1 Docosenoic acid and between 0 and 4% other fatty acids. Other borage oils can be used. Other GLA-containing oils also can be used as the non-polar compound.

(3) Saw Palmetto Extract

Also exemplary of the non-polar compounds used in the provided compositions is saw palmetto extract, a lipophilic extract of the ripe berries of the American dwarf palm (also called *Serenoa repens* or *Sabal serrulata*), which has been used to treat genitourinary and other diseases and to enhance sperm production, breast size and libido, as a mild diuretic, a nerve sedative, an expectorant and a digestive tract tonic, and particularly to treat benign prostate hyperplasia (BHP) (Ernst, *Academia and Clinic* (2002), 136; 42-53; Gordon and Shaughnessy, *Complementary and Alternative Medicine* (2003), 76(6); 1281-1283). Saw palmetto extract is commercially available from a number of sources. Any saw palmetto lipid extract can be used in the provided compositions. Exemplary of the saw palmetto extract that can be used in the provided compositions is Saw Palmetto, Lipophilic Extract, commercially available from Natural Medicinals, Inc., Felda, Fla. This Saw Palmetto Lipophilic Extract is Carbon Dioxide extracted and, in one example, contains, 85.9% total fatty acids, including 0.8% Caproic acid, 2% Caprylic acid, 2.4% Capric acid, 27.1 Lauric acid, 10.3 Myristic acid, 8.1% Palmitic acid, 0.2% Palmitoleic acid, 2% Stearic acid, 26.7 Oleic acid, 4.9% Linoleic acid, 0.7% linolenic acid, 0.42%; 0.42% phytosterols, including 0.42% beta Sitosterol, 0.09% Campesterol, 0.03% Stigmasterol; and 0.2% moisture. Other sources of saw palmetto extract can be used.

(4) Conjugated Linoleic Acid (CLA)

Also exemplary of the PUFA non-polar compounds that can be used in the provided compositions are non-polar compounds containing conjugated fatty acids. Conjugated fatty acids are PUFAs with two or more conjugated double bonds. Conjugated fatty acids can be used as nutritional supplements. Exemplary of the active ingredients containing conjugated fatty acids are compounds containing Conjugated Linoleic acid (CLA), for example, 18:2 $\omega$7, 18:2 $\omega$6; Conjugated Linolenic acid, for example, 18:3$\omega$6, 18:3$\omega$5; and other conjugated fatty acids, for example, 18:3 $\omega$3, 18:4 $\omega$3, and 20:5 $\omega$6. CLA refers to a family of linoleic acid isomers found primarily in meat and dairy products of ruminants. Typically, the CLA compounds contain a mixture of different CLA isomers, for example, C18:2 CLA c9, t11, CLA t10, c12 and other CLA isomers. Exemplary of the CLA that can be used as an active ingredient in the provided compositions is CLA (80%) commercially available from Sanmark, LTD (Dalian, Liaoning Province, China; product code 01057-A80). This CLA is clear white to pale yellow oil and has the following fatty acid composition: NMT (not more than) 9.0% C16:0 Palmitic acid, NMT 4.0% Stearic acid, NMT 15.0% C18:1 Oleic acid, NMT 3.0% C18:2 Linoleic acid, NLT (not less than) 80% C18:2 CLA (including the following isomers: NLT 37.5% C18:2 CLA c9, t11, 37.5% C18:2 CLA t10, c12, and NMT 5.0% other CLA isomers); and NMT 5.0% other fatty acids. Other CLA containing compounds can be used.

ii. Coenzyme Q Active Ingredients

Exemplary of the non-polar active ingredients are compounds containing Coenzyme Q, for example, Coenzyme Q10 (also called CoQ10, ubiquinone, ubidecarenone, ubiquinol and vitamin Q10). Coenzyme Q compounds are benzoquinone compounds containing isoprenyl units. The number of isoprenyl units in each of the different CoQ species is indicated with a number following CoQ. For example, CoQ10 contains 10 isoprenyl units. Coenzyme Q10 is a predominant Coenzyme Q species.

Coenzyme Q can exist in two different forms: an oxidized form and a reduced form. When the oxidized form of a Coenzyme Q species is reduced by one equivalent, it becomes a ubisemiquinone, denoted QH, which contains a free radical on one of the oxygens in the benzene ring of the benzoquinone. Both oxidized and reduced coenzyme Q containing compounds can be used as active ingredients in the provided compositions.

(1) Coenzyme Q10

Exemplary of the Coenzyme Q containing non-polar active ingredients that can be used in the provided compositions are active ingredients containing Coenzyme Q10. Coenzyme Q10 (also called CoQ10, ubiquinone, ubidecarenone, ubiquinol, and vitamin Q10) is a benzoquinone compound that contains 10 isoprenoid units. The "Q" in the name refers to Quinone and the 10 refers to the number of isoprenoid units. CoQ10 typically refers to the oxidized form of CoQ10, which also is referred to as ubidecarenone, as opposed to the reduced form of CoQ10. In the reduced and oxidized CoQ10 are exemplary of the coenzyme Q species that can be used as active ingredients in the provided compositions.

CoQ10 has electron-transfer ability and is present in cellular membranes, such as those of the endoplasmic reticulum, peroxisomes, lysosomes, vesicles and the mitochondria. A decrease in natural CoQ10 synthesis has been observed in sick and elderly people. Because of this observation and its potent antioxidant properties, CoQ10 is used as a dietary supplement and a treatment for diseases such as cancer and heart disease. CoQ10, however, exhibits relatively poor bioavailability.

CoQ10 containing compounds are available commercially. Any CoQ10 compound or reduced CoQ10 compound can be used with the provided composition. Exemplary of the CoQ10 compounds that can be used as active ingredients are coenzyme Q10 compounds containing greater than 98% or greater than about 98% ubidecarenone, for example, the compound sold under the name Kaneka Q10™ (USP Ubidecarenone) by Kaneka Nutrients, L.P., Pasadena, Tex. The compound sold under the name Kaneka Q10™ is fermented entirely from yeast and is identical to the body's own CoQ10 and free from the cis isomer found in some synthetically produced CoQ10 compounds. Any CoQ10 compound can be used in the provided compositions.

iii. Phytosterol-Containing Active Ingredients

Exemplary of the non-polar compounds used as active ingredients in the provided compositions are phytosterol (plant sterol)-containing compounds. Plant sterols are structurally similar to cholesterol and have been found to reduce the absorption of dietary cholesterol, which can affect the levels of serum cholesterol. According to the U.S. Food and Drug Administration (FDA), two servings per day, each containing 0.4 grams of plant sterols, for a total daily intake of at least 0.8 grams, as part of a diet low in saturated fat and cholesterol, may reduce the risk of heart disease. Thus, plant sterols are used in nutritional supplements.

Any phytosterol-containing compound can be used as an active ingredient in the provided compositions. Exemplary of the phytosterol-containing compounds that can be used as active ingredients in the provided compositions are compounds containing plant sterols, for example, the compound sold under the name CardioAid™, distributed by B&D Nutrition and manufactured by ADM Natural Health and Nutrition, Decatur, Ill. This compound contains Kosher, Pareve, and Halal plant sterols that are produced under current food GMPs. The sterols are PCR negative and the material is derived from genetically modified organisms (GMOs). This phytosterol compound contains a minimum of 95% plant sterols, which can include up to 5 plant sterols. The compound can contain, for example, 40-58% Beta sitosterol, 20-30% Campesterol, 14-22% Stigmasterol, 0-6% Brassicasterol and 0-5% Sitostanol. The compound further can contain tocopherols, for example, 0-15 mg/g tocopherols. The compound is tested and is negative for *Salmonella, E. coli* and *Staphylococcus aureus*.

c. Surfactants

In addition to the one or more non-polar compound(s), each of the provided liquid concentrate compositions contains at least one surfactant. The surfactant can be added, using the provided methods, to the water phase and/or the oil phase of the concentrate. In one example, the compositions contain one or more additional surfactants, which are referred to as co-surfactants or emulsifiers.

Surfactants (and co-surfactants) are molecules that contain hydrophobic and hydrophilic portions. In one example, the hydrophobic portion is a hydrophobic tail and the hydrophilic portion is a hydrophilic head of the surfactant molecule.

Exemplary of surfactants that can be used in the provided methods and compositions are surfactants having an HLB value of between 14 or about 14 and 20 or about 20, typically between 16 or about 16 and 18 or about 18. Exemplary of suitable surfactants include, but are not limited to, PEG-derived surfactants, such as PEG-sorbitan fatty acid esters, such as polysorbates, including polysorbate 80 and analogs (e.g. homologs) of polysorbate 80, such as, for example, polysorbate 20, polysorbate 40 and polysorbate 60, and other polysorbates.

Polysorbates are compounds belonging to the family of oily liquids containing esters derived from PEGylated sorbitan (derivative of sorbitol) esterified with one or more fatty acids. Exemplary polysorbate surfactants are Polysorbate 20 (polyoxyethylene (20) sorbitan monolaurate; sold under the trade name Tween 20®); polysorbate 40 (Tween 40® or polyoxyethylene (20) sorbitan monopalmitate); polysorbate 60 (Tween 60® or polyoxyethylene (20) sorbitan monostearate); and polysorbate 80 (Tween 80® or polyoxyethylene (20) sorbitan monooleate). With the parenthetically indicated naming convention for the polysorbates above, the number 20 following "polyoxyethylene" refers to the number of oxyethylene —($CH_2CH_2O$)— groups in the molecule. With the naming convention beginning with "polysorbate" (e.g. "polysorbate 80), the number refers to the type of fatty acid used to esterify the polyoxyethylene sorbitan to generate the polysorbate. For example, the number 20 indicates monolaurate; the number 40 indicates monopalmitate; the number 60 indicates monostearate; and the number 80 indicates monooleate. In one example, the surfactant(s) used in the provided compositions are polysorbate surfactants, including polysorbate 80, for example, the polysorbate 80 sold under the trademark, Tween 80®.

In the provided compositions, the surfactants, aggregate in aqueous liquid dilution compositions to form micelles, which contain the non-polar compound(s). The hydrophilic portion(s) of the surfactant molecules are oriented toward the outside of the micelle, in contact with the aqueous medium, while the hydrophobic portion(s) of the surfactant molecules are oriented toward the center of the micelle, in contact with the non-polar compound(s), which is contained in the center of the micelle. The micelles can contain more than one surfactant.

In general, surfactants also are capable of forming "inverse micelles," which form in lipophilic medium, the hydrophobic tails being in contact with the lipophilic medium and the hydrophilic heads facing the center of the inverse micelle. Typically, however, the surfactants in the provided compositions form micelles in aqueous medium, for example, in aqueous liquids, containing the non-polar ingredient at their center.

Properties of the provided compositions, for example, the particle size of the compositions and desirable properties related to the particle size, are influenced by the choice of surfactant(s) and the relative amount (concentration) of surfactant. For example, the HLB of the surfactant(s) can affect particle size, clarity, taste, smell, crystal formation and other properties of the provided compositions. Similarly, the concentration of the surfactant compared with the concentration(s) of other ingredients, particularly compared with the concentration of water and the concentration of the non-polar compound(s), can affect various desirable properties, for example, the ability to disperse or dissolve in aqueous media, for example, to form a clear aqueous liquid dilution composition or pleasant taste and/or smell.

The PEG used in the PEG-derived surfactants can be any of a plurality of known PEG moieties. Exemplary of suitable PEG moieties are PEG moieties having varying chain lengths, and varying molecular weights, for example, PEG 1000, PEG 200, PEG 500, and PEG 20,000. The numbers following individual PEG moieties indicate the molecular weight (in kilodaltons (kDa) of the PEG moieties. The PEG moiety of the surfactant typically has a molecular weight of between 200 kDa or about 200 kDa and 20,000 kDa or about 20,000 kDa, typically between 200 kDa and 6000 kDa, for example, between 600 kDa or about 600 kDa and 6000 kDa or about 6000 kDa, typically between 200 kDa or about 200 kDa and 2000 kDa or about 2000 kDa, between 600 kDa or about 600 kDa and 1500 kDa or about 1500 kDa, or 200, 300, 400, 500, 600, 800, or 1000 kDa.

Also exemplary of suitable PEG moieties are PEG moieties that are modified, for example, methylated PEG (m-PEG), which is a PEG chain capped with a methyl group. Other known PEG analogs also can be used. The PEG moieties can be selected from among any reactive PEG, including, but not limited to, PEG-OH, PEG-NHS, PEG-aldehyde, PEG-SH, PEG-NH$_2$, PEG-CO$_2$H, and branched PEGs.

i. Concentration of the Surfactant

Typically, the concentration of the surfactant(s) in a particular concentrate composition is selected, as described hereinabove, by formulating an initial concentrate with a surfactant(s) concentration within a starting concentration range, followed by evaluation of the initial concentrate and, optionally, adjusting the surfactant(s) concentration. Alternatively, the surfactant concentration can be chosen based on the concentration of surfactant in one or more existing liquid concentrate formula. Typically, the concentration of the surfactant is between 16% or about 16% and 30% or about 30% (w/w), for example, 16%, 17%, 18%, 19%, 20%, 21% 22%, 23%, 24%, 25%, 26%, 27%, 28%, 29%, 30%, about 16%, about 17%, about 18%, about 19%, about 20%, about 21%, about 22%, about 23%, about 24%, about 25%, about 26%, about 27%, about 28%, about 29% or about 30%, (w/w) of the concentrate. Exemplary of surfactant concentrations within the appropriate concentration range are 17.75% and 25.2%. Typically, the concentration of surfactant is less than or equal to 30% or about 30%.

In one example, the concentration range of the surfactant is between 17% or about 17% and 25% or about 25% (w/w) of the concentrate. In another example, the concentration range of the surfactant is between 18% or about 18% and 25% or about 25% (w/w) of the concentrate. In another example, the concentration range of the surfactant is between 18% or about 18% and 20% or about 20% (w/w) of the concentrate. In another example, the concentration range of the surfactant is between 17% or about 17% and 20% or about 20% (w/w) of the concentrate. In another example, the concentration range of the surfactant is between 16% or about 16% and 20% or about 20% (w/w) of the concentrate.

ii. Hydrophilic Lipophilic Balance (HLB)

Exemplary of the properties of the surfactant(s) that contribute to the desirable properties of the compositions is the HLB (hydrophilic-lipophilic balance) of the surfactant(s). Generally, HLB is a value, derived from a semi-empirical formula, which is used to index surfactants according to their relative hydrophobicity/hydrophilicity. An HLB value is a numerical representation of the relative representation of hydrophilic groups and hydrophobic groups in a surfactant or mixture of surfactants. The weight percent of these respective groups indicates properties of the molecular structure. See, for example, Griffin, W. C. *J. Soc. Cos. Chem.* 1:311 (1949).

Surfactant HLB values range from 1-45, while the range for non-ionic surfactants typically is from 1-20. The more lipophilic a surfactant is, the lower its HLB value. Conversely, the more hydrophilic a surfactant is, the higher its HLB value. Lipophilic surfactants have greater solubility in oil and lipophilic substances, while hydrophilic surfactants dissolve more easily in aqueous media. In general, surfactants with HLB values greater than 10 or greater than about 10 are called "hydrophilic surfactants," while surfactants having HLB values less than 10 or less than about 10 are referred to as "hydrophobic surfactants." HLB values have been determined and are available for a plurality of surfactants (e.g. see U.S. Pat. No. 6,267,985). It should be appreciated that HLB values for a given surfactant or co-surfactant can vary, depending upon the empirical method used to determine the value. Thus, HLB values of surfactants and co-surfactants provide a rough guide for formulating compositions based on relative hydrophobicity/hydrophilicity. For example, a surfactant typically is selected from among surfactants having HLB values within a particular range of the surfactant or co-surfactant, that can be used to guide formulations. Table 1 lists HLB values of exemplary surfactants and co-surfactants.

The surfactants and HLB values set forth in Table 1 are exemplary. Any known surfactant or co-surfactant can be used with the provided compositions (e.g. see U.S. Pat. No. 6,267,985). The surfactant(s) contained in the provided compositions typically have an HLB value between 14 or about 14 and 20 or about 20, for example, 14, 15, 16, 17, 18, 19, 20, about 14, about 15, about 16, about 17, about 18, about 19 or about 20. Exemplary of the surfactants include, but are not limited to, non-ionic surfactants, such as polyethylene glycol (PEG)-Sorbitan fatty acid esters, for example, polysorbates, including PEG-sorbitan monooleates, such as Polyoxyethylene (20) sorbitan monooleate (also called polysorbate 80), as well as analogs of polysorbate 80, such as polysorbate 80 homologs and polysorbate 80 derivatives.

In one aspect, the surfactant is a polysorbate 80 homolog, such as, for example, a polysorbate 80 homolog that differs from a polysorbate 80 parent compound by the addition or removal of one or more methylene unit(s), e.g., —(CH$_2$)$_n$—.

Other known surfactants having HLB values between 14 or about 14 and 20 or about 20, typically between about 16 and 18, also can be suitable. For example, surfactants having similar properties to polysorbate 80 also can be used. Typically, the surfactant is a natural surfactant, for example, a surfactant that is G.R.A.S. (generally recognized as safe) by the FDA and/or Kosher certified.

(1) Co-Surfactants (Emulsifiers)

In one example, the liquid concentrate further contains one or more co-surfactants (emulsifiers). For example, a co-surfactant can be included to improve emulsification of the active ingredient and/or the stability of the composition, for example, by preventing or slowing oxidation of the non-polar compound. Exemplary of a co-surfactant used in the provided concentrates is a phospholipid, for example, phosphatidylcholine.

(a) Phospholipids

Exemplary of the co-surfactants that can be used in the provided compositions are phospholipids. Phospholipids are amphipathic lipid-like molecules, typically containing a hydrophobic portion at one end of the molecule and a hydrophilic portion at the other end of the molecule. A number of phospholipids can be used as ingredients in the provided compositions, for example, lecithin, including phosphatidylcholine (PC), phosphatidylethanolamine (PE), distearoylphosphatidylcholine (DSPC), phosphatidylserine (PS), phosphatidtylglycerol (PG), phosphatidic acid (PA), phosphatidylinositol (PI), sphingomyelin (SPM) or a combination thereof. Typically, the phospholipid is phosphatidylcholine (PC), which sometimes is referred to by the general name "lecithin." Exemplary of the phospholipids that can be used as co-surfactants in the provided compositions are the phospholipids sold by Lipoid, LLC, Newark, N.J., for example, Purified Egg Lecithins, Purified Soybean Lecithins, Hydrogenated Egg and Soybean Lecithins, Egg Phospholipids, Soybean Phospholipids, Hydrogenated Egg and Soybean Phospholipids. Synthetic Phospholipids, PEGylated Phospholipids and phospholipid blends sold by Lipoid, LLC. Exemplary of the phosphatidylcholine that can be used as a co-surfactant in the provided compositions is the phosphatidylcholine composition sold by Lipoid, LLC, under the name Lipoid S100, which is derived from soy extract and contains greater than 95% or greater than about 95% phosphatidylcholine.

In one example, the phospholipid, for example, PC, represents less than or equal to 1% or about 1%, by weight (w/w) of the concentrate. In one example, the phosphatidylcholine represents between 0.1% or about 0.1% and 1% or about 1%, for example, 0.1, 0.15, 0.2, 0.25, 0.3, 0.35, 0.4, 0.45, 0.5, 0.6, 0.65, 0.66, 0.6690, 0.7, 0.75, 0.8, 0.85, 0.9, 0.95 or 1%, per weight (w/w), of the concentrate. In one example, the phospholipid represents between 0.15% or about 0.15% and 0.7% or about 0.7%, by weight (w/w) of the concentrate.

iii. Water

Each of the provided liquid concentrates further contains water, typically a high concentration of water, for example, a concentration of water within a concentration range of between 60% or about 60% and 80% or about 80%, by weight (w/w), of the concentrate, for example, 60%, 61%, 62%, 63%, 64%, 65%, 66%, 67%, 68%, 69%, 70%, 71%, 72%, 73%, 74%, 75%, 76%, 77%, 78%, 79%, 80%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% (w/w) of the concentrate. Exemplary of water concentrations in the provided liquid concentrates are 71.74%, 75.8165%, 74.25%, 68.7865% and 68.29% (w/w) of the concentrate. In one example, the concentration range of the water is between 65% or about 65% and 80% or about 80% (w/w) of the concentrate. In one example, the concentration range of the water is between 65% or about 65% and 75% or about 75% (w/w) of the concentrate, for example, between 65% or about 65% and 76% or about 76%, by weight, of the concentrate. In another example, the amount of water is between 68% or about 68% and 75% or about 75%, by weight, of the concentrate.

The water is added, in the provided processes described below, to the water phase of the concentrate. In one example, the water is filtered water, for example, water that is filtered prior to adding it to the concentrate formula, for example, by charcoal filter, ion exchange, reverse osmosis, UV sterilization and/or filtering using a filter, for example, a 50-100 micron filter. Typically, when a filter is used, it is an end point of use filter, which filters the water before it reaches the tank in the provided process. Alternatively, previously filtered water can be added to the concentrates.

iv. Preservatives and Sterilizers

In one example, the provided liquid concentrate further comprises one or more preservatives (or preservativers) and/or sterilizers. The preservative(s) can be included to improve the stability of the concentrate, and the compositions made by diluting the concentrate, over time. Preservatives, particularly food and beverage preservatives, are well known. Any known preservative can be used in the provided compositions. Exemplary of the preservatives that can be used in the provided compositions are oil soluble preservatives, for example, benzyl alcohol, Benzyl Benzoate, Methyl Paraben, Propyl Paraben, antioxidants, for example, Vitamin E, Vitamin A Palmitate and Beta Carotene. Typically, a preservative is selected that is safe for human consumption, for example, in foods and beverages, for example, a GRAS certified and/or Kosher-certified preservative, for example, benzyl alcohol.

The preservative typically represents less than 1%, less than about 1%, 1% or about 1%, by weight (w/w), of the liquid nanoemulsion concentrate or between 0.1% or about 0.1% and 1% or about 1%, by weight, of the concentrate, for example, 0.1%, 0.2%, 0.3%, 0.4%, 0.5%, 0.6%, 0.7%, 0.725%, 0.75%, 0.8%, 0.9%, 1%, about 0.1%, about 0.2%, about 0.3%, about 0.4%, about 0.5%, about 0.6%, about 0.7%, about 0.8%, about 0.9%, about 1%, by weight (w/w), of the liquid concentrate.

v. Emulsion Stabilizers (Co-Emulsifier)

In one example, the provided liquid concentrates further contain one or more emulsion stabilizers (co-emulsifiers), which can be used to stabilize the liquid nanoemulsion concentrate and/or the aqueous compositions containing the diluted concentrates. In one example, the emulsion stabilizer increases the viscosity of the liquid concentrate. In one example, one or more emulsion stabilizers is added, during formulation, after evaluation of an initial concentrate, particularly if the oil and water phases of the initial concentrate (or the aqueous liquid dilution composition resulting from dilution of the initial concentrate) appear to be separating. Addition of the emulsion stabilizer can prevent separation of the oil and water phases.

Exemplary of an emulsion stabilizer that can be used in the provided compositions is a composition containing a blend of gums, for example, gums used as emulsifying agents, for example, a blend containing one or more of xanthan gum, guar gum and sodium alginate, for example, the emulsion stabilizer sold under the brand name SALADIZER®, available from TIC Gums, Inc. (Belcamp, Md.). Other gums can be included in the emulsion stabilizer, for example, gum acacia and sugar beet pectin. Other blends of similar gums can also be used as emulsion stabilizers.

The emulsion stabilizer can be added to the water phase, the oil phase, and typically to the water and the oil phase, during formation of the liquid concentrates. In one example, the emulsion stabilizer is added to the water phase at a concentration, such that it represents less than 1% or about 1% w/w of the liquid concentrate. In one example, the emulsion stabilizer is added to the water phase for a final concentration of between 0.1% or about 0.1% and 1% or about 1%, for example, 0.1%, 0.12%, 0.13%, 0.14%, 0.15%, 0.16%, 0.17%, 0.18%, 0.19%, 0.2%, 0.25%, 0.3%, 0.31%, 0.32%, 0.33%, 0.34%, 0.35%, 0.36%, 0.37%, 0.38%, 0.39%, 0.4%, 0.5%, 0.6%, 0.7%, 0.8%, 0.9% or 1% w/w of the liquid concentrate. In one example, the emulsion stabilizer is added to the oil phase such that it represents less than 0.1% or about 0.1%, for example, between 0.01% or about 0.01% and 0.1% or about 0.1%, for example, 0.01%, 0.02%, 0.03%, 0.04%, 0.05%, 0.06%, 0.061%, 0.062%, 0.063%, 0.0635%, 0.07%, 0.08%, 0.09% or 0.1%, by weight (w/w) of the concentrate. In one example, the emulsion stabilizer is added to the water phase and the oil phase, for example, at a concentration within the oil and water phase concentration ranges listed above. In one such example, the emulsion stabilizer represents less than 1%, for example, between 0.01% or about 0.01% and 1% or about 1% (w/w), emulsion stabilizer, for example, 0.01%, 0.02%, 0.03%, 0.04%, 0.05%, 0.06%, 0.061%, 0.062%, 0.063%, 0.0635%, 0.07%, 0.08%, 0.09%, 0.1%, 0.12%, 0.13%, 0.14%, 0.15%, 0.16%, 0.17%, 0.18%, 0.19%, 0.2%, 0.25%, 0.3%, 0.31%, 0.32%, 0.33%, 0.34%, 0.35%, 0.36%, 0.37%, 0.38%, 0.39%, 0.4%, 0.5%, 0.6%, 0.7%, 0.8%, 0.9% or 1%, by weight (w/w), of the liquid concentrate.

vi. Solvents

In one example, the liquid concentrates further contain a solvent, for example, an oil. Typically, the solvent is included in the composition in addition to the non-polar active ingredient, and is used to dissolve the non-polar active ingredient. In one example, the solvent is an oil that is not contained in the non-polar active ingredient. When a solvent is included in the concentrate, it typically is used to dissolve the non-polar compound before mixing with the other ingredients, for example, before mixing with the other oil phase ingredients. In one example, use of a solvent reduces the crystal size and/or increase the clarity of the aqueous liquid dilution composition containing the diluted concentrate. Exemplary of solvents that can be used in the provided concentrates are oils (in addition to the non-polar active ingredient), for example, Vitamin E oil, flaxseed oil, CLA, Borage Oil, D-limonene, Canola oil, corn oil, MCT oil and oat oil. Other oils also can be used. Exemplary of the Vitamin E oil, used as a solvent in the provided compositions, is the oil sold by ADM Natural Health and Nutrition, Decatur, Ill., under the name Novatol™ 5-67 Vitamin E (D-alpha-Tocopherol; ADM product code 410217). This Vitamin E oil contains at least 67.2% Tocopherol and approximately 32.8% soybean oil.

In one example, the concentration of the solvent is within a concentration range of between 1% or about 1% and 10% or about 10%, for example, 1%, 2%, 3%, 3.25%, 3.5%, 3.75%, 4%, 5%, 5.25%, 5.5% or 5.75%, w/w, of the concentrate. In another example, the concentration is within the concentration range of between 3% or about 3% and 6% or about 6%, w/w, of the liquid concentrate. In another example, it is between 3.75% and 5.25% w/w, of the liquid concentrate.

vii. Flavors

In one example, the concentrate further contains one or more flavors or flavoring agents, for example, any compound to add flavor to the concentrate and/or to the aqueous liquid dilution composition containing the diluted concentrate, for example, the food or beverage containing the concentrate. Several flavors are well known. Any flavor can be added to the concentrates, for example, any flavor sold by Mission Flavors, Foothill Ranch, Calif. Exemplary of flavors that can be used are fruit flavors, such as guava, kiwi, peach, mango, papaya, pineapple, banana, strawberry, raspberry, blueberry, orange, grapefruit, tangerine, lemon, lime and lemon-lime; cola flavors, tea flavors, coffee flavors, chocolate flavors, dairy flavors, root beer and birch beer flavors, methyl salicylate (wintergreen oil, sweet birch oil), citrus oils and other flavors. Typically, the flavors are safe and/or desirable for human consumption, for example, GRAS or Kosher-certified flavors. Exemplary of flavoring agents that can be used in the compositions are lemon oil, for example lemon oil sold by Mission Flavors, Foothill Ranch, Calif.; and D-limonene, for example, 99% GRAS certified D-Limonene, sold by Florida Chemical, Winter Haven, Fla. Typically, the flavor is added, using the provided methods, to the nanoemulsion concentrates after combining the oil and water phases. Alternatively, flavor(s) can be added to the water and/or oil phase directly.

Typically, the concentration of flavoring agent added to the provided concentrates is less than 5% or about 5%, typically less than 1% or about 1%, for example, 0.1%, 0.2%, 0.3%, 0.4%, 0.5%, 0.6%, 0.7%, 0.8%, 0.9%, 0.37% or 0.525%.

viii. pH Adjusters

In one example, one or more pH adjusters are added to the provided concentrates, typically to the emulsion that is formed after combining the water and oil phases according to the provided methods. Alternatively, the pH adjuster can be added, at an appropriate concentration to achieve a desired pH, to the oil phase and/or the water phase. Typically, the pH adjuster is added to adjust the pH of the concentrate to within a range of 2.0 or about 2.0 to 4.0 or about 4.0. One or more of a plurality of pH adjusting agents can be used. Typically, the pH adjusting agent is safe for human consumption, for example, GRAS certified. Exemplary of the pH adjuster is citric acid, for example, the citric acid sold by Mitsubishi Chemical, Dublin, Ohio.

Typically, the concentration of pH adjuster added to the provided concentrates is less than 5% or about 5%, typically less than 1% or about 1%, for example, 0.1%, 0.2%, 0.3%, 0.4%, 0.5%, 0.6%, 0.7%, 0.8%, 0.9%, 0.28% or 0.19%.

2. Powder Forms of the Compositions

The compositions also can be provided in powder form, i.e. powder that is made by converting the provided nanoemulsion concentrates into a powder, using one of several well-known methods (e.g. spray-drying and/or milling). The powder compositions include, but are not limited to, coated or uncoated swallowable or chewable tablets, dry powders in hard or soft gelatin capsules, and dry powders in individual or multiple use packages for reconstituted suspensions or sprinkles. Preferable solid dosage forms are coated or uncoated swallowable or chewable tablets. Suitable methods for manufacturing the powder compositions are well known in the art.

Additionally, the powder composition can further comprise at least one excipient. Excipients include, but are not limited to, diluents (sometimes referred to as fillers) including, for example, microcrystalline cellulose, mannitol, lactose, calcium phosphate, dextrates, maltodextrin, starch, sucrose, and pregelatinized starch; disintegrants including, for example, crospovidone, sodium starch glycolate, croscarmellose sodium, starch, pregelatinized starch, and carboxymethylcellulose sodium; binders including, for example, starch, hydroxypropyl cellulose, hydroxypropylmethyl cellulose, pregelatinized starch, guar gum, alginic acid, acacia, carboxymethylcellulose sodium, and polyvinyl pyrrolidone; glidants including, for example, colloidal silicon dioxide and talc; and lubricants/antiadherents including, for example, magnesium stearate, calcium stearate, stearic acid, sodium stearyl fumarate, glyceryl monostearate, hydrogenated vegetable oil, and talc.

The powder forms may be used for any convenient dosage amount the non-polar compound. Generally, the level of non-polar compound may be increased or decreased according to the judgment of the physician, pharmacist, pharmaceutical scientist, or other person of skill in the art. The amount of the remaining non-active ingredients can be adjusted as needed.

Typically, the concentration of the excipients is within a concentration range of between 50% or about 50% and 85% or about 85%, for example, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 or more, %, by weight, of the free flowing powder.

In one example, the powder form is a free-flowing powder. Free-flowing powders can be obtained using techniques well known in the art, such as, but not limited to, spray drying, freeze drying or absorption plating. In one example, in order to achieve a free flowing powder, the protein derivative is formulated with an excipient such as lactose or starch. For example, the formulation can be a spray-dried lactose formulation (see e.g., U.S. Pat. No. 4,916,163).

The methods for forming the powders include spray drying. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50 Chem. Eng. Prog. Monogr. Series 2 (1954), and Masters, Spray Drying Handbook (Fourth Edition 1985). Methods for spray drying are well known (see, e.g. U.S. Pat. Nos. 5,430, 021; 6,534,085 and U.S. Application Publication No. 2007/

0184117). In general, spray drying is used to dry a heated liquid by passing it through hot gas. One or more spray nozzles is used to atomize the liquid in a cooling tower or chamber. As the material is atomized (sprayed), the surface tension causes a uniform spherical particle to form, which is passed through the cooling chamber and hardens into a solid intact sphere. The spray dried particles can be between at or about 0.5 microns and at or about 100 microns, and typically are less than at or about 10 microns, typically less than at or about 5 microns, and typically less than at or about, or at or about, 1 micron.

Provided are methods for spray drying the liquid nanoemulsion compositions to form powder compositions. In the spray drying methods, the liquid nanoemulsion compositions can be heated, e.g. to a temperature between at or about 100 and at or about 150° F., typically between 110° F. and 140° F., e.g. at or about 110, 115, 120, 125, 130, 135 or 140° F. The compositions can be mixed while heating, such as with any of the mixers described herein, for example, homogenizers (e.g. reversible homogenizers and piston-driven homogenization).

For spray-drying, one or more excipients are mixed with a polar solvent, typically water, and heated, e.g. to a temperature between at or about 100° F. and at or about 150° F., typically between 110° F. and 140° F., e.g. at or about 110, 115, 120, 125, 130, 135 or 140° F. In one example, the excipient is mixed with water in an amount of one part excipient (by weight) to two parts water (by weight). The excipient-solvent (e.g. water) mixture can be mixed while heating, e.g. using any of the mixers described herein, for example, homogenizers (e.g. reversible homogenizers and piston-driven homogenization) with heating during the mixing. The heated liquid nanoemulsion composition and the heated water-excipient mixture then are mixed together, such as by transferring one mixture to the other, e.g. by any of the transfer means provided herein. Typically, the two mixtures are homogenized, e.g. with a reversible homogenizer or piston-driven homogenizer or any other homogenizer. The homogenized mixture then is subject to spray drying using a spray dryer.

Exemplary of the spray dryers are cyclone spray dryers. During spray drying with cyclone spray dryers, the homogenized mixture is pumped into an atomizing device where it is broken into small droplets. Upon contact with a stream of hot air, the moisture is removed very rapidly from the droplets while still suspended in the drying air. The dry powder is separated from the moist air in cyclones by centrifugal action. The centrifugal action is caused by the great increase in air speed when the mixture of particles and air enters the cyclone system. The dense powder particles are forced toward the cyclone walls while the lighter, moist air is directed away through the exhaust pipes. The powder settles to the bottom of the cyclone where it is removed through a discharging device. Sometimes the air-conveying ducts for the dry powder are connected with cooling systems which admit cold air for transport of the product through conveying pipes. Cyclone dryers have been designed for large production schedules capable of drying ton-lots of powder per hour.

As will be appreciated by one of skill in the art, the inlet temperature and the outlet temperature of the spray drier are not critical but will be of such a level to provide the desired particle size, of less than at or about 1 micron, and to result in a powder that has a desired property. Typically, the ability of the free flowing powder to yield a clear (or relatively clear) liquid dilution composition upon dilution in an aqueous medium is the desired property that is evaluated. In this regard, the inlet and outlet temperatures are adjust depending on the melting characteristics of the liquid nanoemulsion components and the composition of the homogenized liquid nanoemulsion concentrate/excipient mixture. The inlet temperature is between at or about 60° C. and at or about 170° C. with outlet temperatures between at or about 40° C. to at or about 120° C. Preferably inlet temperatures are from at or about 90° C. to at or about 120° C. and outlet temperatures are from at or about 60° C. to at or about 90° C. The flow rate which is used in the spray drying equipment will generally be at or about 3 mL per minute to at or about 15 mL per minute. The atomizer air flow rate will very between values of at or about 25 L per minute to at or about 50 L per minute. Commercially available spray dryers are well known to those of skill in the art, and suitable settings for any particular dispersion can be readily determined by one of skill in the art without undue experimentation. Operating conditions such as inlet temperature and outlet temperature, feed rate, atomization pressure, flow rate of the drying air, and nozzle configuration can be adjusted in accordance with the manufacturer's guidelines.

In some examples, the dry powder is stored into a capsule form or is pressed into a tablet. For use as tablets, the compositions typically contain multiple other excipients. These excipients include tablet disintegrants, such as the corn starch, glidants, such as the silicon dioxide, and lubricants such as the magnesium stearate. Ordinarily these compositions contain minor amounts by weight of glidants and lubricants, e.g., each two percent (2%) or less by weight. Tablet disintegrants are optionally present, and, if present, are included in sufficient amounts to assure that the tablet disintegrates upon ingestion. According materials, such as corn starch are employed at concentrations of from about zero to about 30 percent by weight of the composition.

Free flowing powders also can be used to administer the active agent by inhalation using a dry powder inhaler. Such dry powder inhalers typically administer the active agent as a free-flowing powder that is dispersed in a patient's air-stream during inspiration. In order to achieve a free flowing powder, the active agent is typically formulated with a suitable excipient such as lactose or starch. For example, such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device. Examples of dry powder inhaler delivery devices include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519); Turbuhaler (AstraZeneca, Wilmington, Del.) (see, e.g., U.S. Pat. No. 4,524,769); Rotahaler (GlaxoSmithKline) (see, e.g., U.S. Pat. No. 4,353,365); and Handihaler (Boehringer Ingelheim). Further examples of suitable DPI devices are described in U.S. Pat. Nos. 5,415,162, 5,239,993, and 5,715,810 and references cited therein.

3. Liquid Dilution Compositions Containing the Diluted Concentrates

Among the compositions provided herein are liquid dilution compositions, typically aqueous liquid dilution compositions, containing the non-polar compounds. The aqueous liquid dilution compositions are made by diluting the provided liquid nanoemulsion concentrates into aqueous media, for example, beverages, for example, water, flavored water, soda, milk, juices, including fruit juices, sauces, syrups, soups, sports drinks, nutritional beverages, energy drinks, vitamin-fortified beverages, or any beverage.

In one example, the aqueous liquid dilution compositions contains between 0.05 grams (g) or about 0.05 g and 10 g or about 10 g, typically between 0.05 g and 5 g, of the liquid concentrate per 8 fluid ounces or about 8 fluid ounces, at least 8 fluid ounces or at least about 8 fluid ounces, or less than 8 fluid ounces or less than about 8 fluid ounces, or per serving size, of the aqueous medium, for example, 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1 g, 2 g, 3 g, 4 g, 5 g, 6 g, 7 g, 8 g, 9 g, or 10 g of the concentrate per 8 fluid ounces, about 8 fluid ounces, or at least 8 fluid ounces or at least about 8 fluid ounces of the aqueous medium, for example 8, 9, 10, 11, 12, 13, 14, 15, 16, 17, 18, 19, 20, 25, 30, 35, 40, 45, 50, 100, 200 or more fluid ounces, of aqueous medium.

In another example, the aqueous liquid dilution composition contains between 1 mL or about 1 mL and 10 mL or about 10 mL of the liquid concentrate, for example, 1 mL, 2 mL, 3 mL, 4 mL, 5 mL, 6 mL, 7 mL, 8 mL, 9 mL or 10 mL of the concentrate, per 8 fluid ounces, about 8 fluid ounces, at least 8 fluid ounces or at least about 8 fluid ounces, or less than 8 fluid ounces or less than about 8 fluid ounces, or per serving size, of the aqueous medium, for example 8, 9, 10, 11, 12, 13, 14, 15, 16, 17, 18, 19, 20, 25, 30, 35, 40, 45, 50, 100, 200 or more fluid ounces, of aqueous medium.

In another example, the aqueous liquid dilution composition contains at least 10 mg or about 10 mg, typically at least 25 mg or about 25 mg, typically at least 35 mg, of the non-polar compound, for example, the non-polar active ingredient, per 8 fluid ounces or about 8 fluid ounces, at least 8 fluid ounces or at least about 8 fluid ounces of the aqueous medium, or less than 8 ounces or less than about 8 ounces, or per serving size, of the aqueous medium; for example, 10, 11, 12, 13, 14, 15, 16, 17, 18, 19, 20, 21, 22, 23, 25, 25, 26, 27, 28, 29, 30, 31, 32, 33, 34, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000 mg, or more, of the non-polar compound per at least 8 fluid ounces or at least about 8 fluid ounces of aqueous medium.

In another example, the aqueous liquid dilution composition contains the concentrate diluted at a dilution factor of between 1:10 or about 1:10 and 1:1000 or about 1:1000 or more, typically between 1:10 or about 1:10 and 1:500 or about 1:500 or more, for example, diluted not more than 1:10 or about 1:10, 1:20 or about 1:20, 1:25 or about 1:25, 1:50 or about 1:50, 1:100 or about 1:100, 1:200 or about 1:200, 1:250 or about 1:250, 1:300 or about 1:300, 1:400 or about 1:400, 1:500 or about 1:500, for example, 1:10, 1:20, 1:25, 1:30, 1:35, 1:40, 1:50, 1:55, 1:60, 1:65, 1:70, 1:75, 1:80, 1:90, 1:100, 1:110, 1:120, 1:130, 1:140, 1:150, 1:160, 1:170, 1:180, 1:190, 1:200, 1:210, 1:220, 1:230, 1:235, 1:240, 1:250, 1:260, 1:270, 1:280, 1:290, 1:300, 1:350, 1:400, 1:450, 1:500 or more. In another example, the aqueous liquid dilution compositions contain the liquid concentrate diluted to any amount. In another example the dilution is less than 1:10 or about 1:10.

Properties of the provided liquid concentrates that are diluted into the aqueous medium contribute to various properties of the provided resulting aqueous liquid dilution compositions, for example, clarity; desirability for human consumption, for example, pleasant taste, and/or smell, for example, lack of "fishy" taste/smell, lack of "ringing" and lack of crystal formation; stability, for example, lack of oxidation, "ringing" and/or precipitation over time; and safety for human consumption. As described above, the liquid concentrates are formulated according to the desired properties of the aqueous liquid dilution compositions containing the concentrates.

a. Clarity

In one example, the aqueous liquid dilution compositions are clear aqueous liquid dilution compositions or non-turbid aqueous liquid dilution compositions, for example, as determined, as described below, empirically or by measuring turbidity and/or particle size. In another example, the aqueous liquid dilution compositions are not clear, or not completely clear. The liquids may be more or less clear, or have the same clarity as another liquid, for example, an aqueous liquid dilution composition made according to the provided methods or a beverage, for example, a beverage that does not contain the diluted concentrate. Properties of the liquid concentrates can affect the clarity of the liquid. A number of parameters can vary the clarity of the liquids, for example, the relative concentration of surfactant, non-polar compound and/or water; the type of non-polar ingredient; the concentration of excipient(s) in the particular non-polar compound; and the purity of the non-polar compound, for example, whether it has been standardized to a high purity, or whether it is an extract or a filtered extract. For example, an aqueous liquid dilution composition made by diluting a concentrate containing a non-polar active ingredient that contains lecithin, for example a high amount of lecithin, may be less clear than one made with a concentrate containing a non-polar compound that does not contain lecithin. In another example, a liquid concentrate containing a non-polar compound that is a filtered extract may produce a clearer aqueous liquid dilution composition when diluted than a concentrate containing a crude extract.

i. Clarity Determined by Empirical Evaluation

In one example, the clarity/turbidity of the aqueous liquid dilution composition containing the diluted concentrate is evaluated qualitatively, by observation. In one example, a liquid can be considered clear if it does not have a cloudy appearance and/or if no or few particles are visible when viewing the liquid with the naked eye or if it is the same or substantially similar in clarity to another liquid, for example, a beverage, for example, water, fruit juice, soda or milk. In some cases, the aqueous liquid dilution composition is as clear or about as clear as water or another liquid, for example a beverage. For example, the liquid (containing the liquid concentrate diluted in an aqueous medium, for example, a beverage) can be as clear or about as clear as the aqueous medium not containing the liquid concentrate. In a related example, there is no substantial difference, for example, no observable difference, between the aqueous liquid dilution composition containing the concentrate and the aqueous medium without the concentrate. A clear liquid is not necessarily colorless, for example, a yellow liquid that contains no visible particles or cloudiness can be considered clear. In another example, the liquid is clear or partially clear or substantially clear if no crystals are visible and/or if no "ringing" is observed on the container containing the liquid.

ii. Clarity Determined by Particle Size or Number of Particles

In another example, clarity of the aqueous liquid dilution composition is evaluated by measuring the particle size and/or number of particles of the liquid.

In one example, the aqueous liquid dilution compositions have a particle size less than 200 nm or less than about 200 nm, for example, 5, 10, 15, 20, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. In another example, the aqueous liquid dilution composition has a particle size less than 100 nm or about 100 nm, less than 50 nm or about 50 nm or less than 25 or about 25 nm. Typically, the particle size of the aqueous liquid dilution composition is between 5 nm or about 5 nm and 200 nm or about 200 nm, or between 5 nm or about 5 nm and 50 nm or about 50 nm.

Typically, the particle size of the provided aqueous liquid dilution composition containing the liquid concentrate, which contains the non-polar compound, is smaller than the particle size of a liquid containing the non-polar compound (not formulated in a liquid concentrate).

iii. Turbidity

In another example, the clarity of the liquid is evaluated and/or expressed using a turbidity measurement, for example, Nephelometric Turbidity Units (NTU), as measured using the provided methods, described below. In this example, turbidity is measured optically, to get value indicating the cloudiness or haziness of the liquid, which correlates with particles in suspension in the liquid. The more clear a liquid is, the lower its turbidity value.

In one example, the clear aqueous liquid dilution composition has a turbidity value (NTU) of 30 or about 30; or an NTU value of less than 30 or about 30, for example, less than 29 or about 29, less than 28 or about 28, less than 27 or about 27, less than 26 or about 26, less than 25 or about 25, less than 24 or about 24, less than 23 or about 23, less than 22 or about 22, less than 21 or about 21, less than 20 or about 20, less than 19 or about 19, less than 18 or about 18, less than 17 or about 17, less than 16 or about 16, less than 15 or about 15, less than 14 or about 14, less than 13 or about 13, less than 12 or about 12, less than 11 or about 11, less than 10 or about 10, less than 9 or about 9, less than 8 or about 8, less than 7 or about 7, less than 6 or about 6, less than 5 or about 5, less than 4 or about 4, less than 3 or about 3, less than 2 or about 2, less than 1 or about 1; or 29 or about 29, 28 or about 28, 27 or about 27, 26 or about 26, 25 or about 25, 24 or about 24, 23 or about 23, 22 or about 22, 21 or about 21, 20 or about 20, 19 or about 19, 18 or about 18, 17 or about 17, 16 or about 16, 15 or about 15, 14 or about 14, 13 or about 13, 12 or about 12, 11 or about 11, 10 or about 10, 9 or about 9, 8 or about 8, 7 or about 7, 6 or about 6, 5 or about 5, 4 or about 4, 3 or about 3, 2 or about 2, 1 or about 1, or 0 or about 0.

In another example, the turbidity value of the aqueous liquid dilution composition is less than 200 or less than about 200, for example, 200, 175, 150, 100, 50, 25 or less.

In another example, it is desirable that the aqueous liquid dilution composition contains a turbidity value that is comparable, for example, about the same as, the same as, or less than or greater than, the turbidity value of another liquid, for example, a beverage not containing the liquid concentrate or an aqueous liquid dilution composition made by the provided methods.

b. Stability

Typically, the provided aqueous liquid dilution compositions containing the concentrates are stable, for example, free from one or more changes over a period of time, for example, 1, 2, 3, 4, 5, 6, 7, 8, 9, 10, 11 or 12 months, 1, 2, 3, 4 or more years.

In one example, the compositions are stable because they are free from oxidation or substantial oxidation over time. In another example, they are stable because they remain clear over time. In another example, the stable compositions remain safe and/or desirable for human consumption over time. In one example, stability refers to the lack of precipitates forming in the compositions over the period of time. In a related example, the compositions are stable because they do not exhibit "ringing," formation of a whitish or opaque ring around the perimeter of the container holding the liquid, typically at the surface of the liquid. Ringing typically is undesirable, particularly in the case of a liquid for human consumption, for example, a beverage.

In another example, the composition is stable if it does not exhibit any visible phase separation over a period of time, for example, after 24 hours, after one week or after one month. In one example, the compositions are stable if they exhibit one or more of these described characteristics, over time, when kept at a particular temperature. In one example, the compositions remain stable at room temperature, for example, 25° C. or about 25° C. In another example, the compositions remain stable at between 19° C. and 25° C. In another example, the compositions remain stable at refrigerated temperatures, for example, 4° C. or about 4° C., or at frozen temperature, for example, at −20° C. or about −20° C.

Stability refers to a desirable property of the provided compositions, for example, the ability of the provided compositions to remain free from one or more changes over a period of time, for example, 1, 2, 3, 4, 5, 6, 7, 8, 9, 10, 11 or 12 months, 1, 2, 3, 4 or more years. In one example, the composition is stable if it is formulated such that it remains free from oxidation or substantial oxidation over time. In another example, the stable compositions remain clear over time. In another example, the stable compositions remain safe and/or desirable for human consumption over time. In one example, stability refers to the lack of precipitates forming in the compositions over the period of time. In a related example, stability refers to the lack of "ringing" over the period of time. In another example, the composition is stable if it does not exhibit any visible phase separation over a period of time, for example, after 24 hours, after one week or after one month. In one example, the compositions are stable if they exhibit one or more of these described characteristics, over time, when kept at a particular temperature.

In one example, the compositions are stable at room temperature, for example, 25° C. or about 25° C. In another example, the compositions remain stable at between 19° C. and 25° C. In another example, the compositions remain stable at refrigerated temperatures, for example, 4° C. or about 4° C., or at frozen temperature, for example, at −20° C. or about −20° C.

c. Desirable Characteristics for Human Consumption

In one example, the liquid dilution composition is desirable for human consumption, for example, for use in a food or beverage. Different properties of the liquid dilution composition can contribute to its desirability as a consumable product. For example, taste, smell, clarity, color, crystal formation, precipitation and "ringing," all can relate to desirability.

In one example, the liquid dilution composition has a pleasant taste and/or smell, for example, due to one or more flavors added to the concentrate and/or to the aqueous medium. In another example, the liquid dilution composition containing the concentrate is free from an unpleasant taste or smell, for example, a "fishy" taste or smell. In one example, the concentrate smells or tastes less unpleasant, for example, fishy, compared to another aqueous liquid dilution composition.

In another example, the aqueous liquid dilution composition is desirable because it does not have crystals or has fewer crystals compared with another aqueous liquid dilution composition. In another example, the aqueous liquid dilution composition is desirable because it does not exhibit ringing.

d. Safety

Typically, the aqueous liquid dilution compositions containing the concentrates are safe for human consumption, for example, containing only ingredients approved by the FDA for human consumption, for example GRAS-certified ingredients. In one example, one or more of the ingredients, for example, all the ingredients, are Kosher-certified. Safety of the compositions also relates to stability over time. Lack of or minimum oxidation of the compositions over time can contribute to the safety of the compositions.

e. Oral Bioavailability

In one example, the non-polar compounds, for example, the non-polar active ingredients, contained in the aqueous liquid dilution compositions exhibit a high or relatively high bioavailability, for example, a bioavailability that is higher than a liquid containing the non-polar active ingredient alone (i.e. not formulated in the liquid concentrate). Bioavailability relates to the ability of the body to absorb the non-polar active ingredient into a particular space, tissue cell and/or cellular compartment. Typically, non-polar active ingredients in liquids having small particle sizes are better absorbed than those with larger particle sizes.

C. METHODS FOR MAKING LIQUID NANOEMULSION CONCENTRATES CONTAINING NON-POLAR COMPOUNDS

Also provided are methods for making the liquid nanoemulsion concentrates. General equipment and steps of the methods are detailed below. In one example, the general methods for making the concentrates are performed using a bench-top manufacturing process, which is used for making relatively smaller-sized batches of the concentrates. In another example, the general methods for making the concentrates are performed using a scaled-up manufacturing processes, which is used for making relatively larger batches of the concentrates. The bench-top process can be scaled up to the scaled-up process. Any concentrate made using the bench-top method can be made using the scaled-up process, by scaling up the method.

1. Equipment for Making the Concentrates

Various equipment, for example, vessels for mixing the oil phase, water phase and emulsion, for example, tanks; scales; mixers, including standard mixers and homogenizers; heating and cooling apparatuses, including water-jacketed tanks, hot plates, water baths and chillers (coolers), including recirculating coolers; transfer apparatuses, for example, transfer means, for example, pumps, hoses, sanitary fittings; ball valves; purifiers, for example, filters, for example, carbon filters, ion exchange equipment, reverse osmosis equipment, end-point filters and end product filters; evaluation means, for example, pH and temperature meters; and other equipment, is used in various steps of the provided methods for making the concentrates. The choice of equipment depends on a plurality of factors, including batch size and manufacturing process.

a. Scales

One or more scales typically is used to measure the ingredients before adding them to the appropriate vessel. Alternatively, the ingredients can be weighed in the vessel, for example, in a tank on top of a scale.

Any of a plurality of well-known, commercially sold scales can be used to weigh the ingredients. Choice of scale(s) can depend on a number of factors, including the mass of the final concentrate being made and the ingredient being weighed. In one example, multiple scales are used to weigh the various ingredients of the concentrate. In general, relatively larger capacity (weight) scale(s) are used in making larger batches of concentrate while relatively smaller capacity scale(s) are used in making smaller batches.

Exemplary of the scales used with the provided methods to weigh the ingredients are a Toledo Scale (Model GD13x/USA), a Sartorius Basic Analytical Scale (Model BA110S) which is a basic series analytical scale with a 110 g capacity and a resolution of 0.1 mg; and an OHAUS Scale (Model CS2000), which is a compact portable digital scale having a 2000 g capacity and a resolution of I g.

b. Purifiers, Including Filters

Purifiers, typically more than one purifier, for example, filters, are used in the provided methods to remove impurities in the ingredients prior to their addition to the concentrate and/or from the final concentrate and/or an intermediate phase of the concentrate. For example, the water added to the water phase typically is filtered water. In one example, one or more purifiers, for example, carbon filters, ion exchange purifiers, reverse osmosis purifiers, and/or end point filters are used to filter water, for example, city water, prior to its addition to the water phase, for example, to remove impurities, for example, sediment, from the water.

Exemplary of the purifiers that can be used with the provided methods are filters, for example, 100 micron filters and carbon filters, which are filters that use activated carbon to remove impurities by chemical adsorption. Carbon filtering typically is used for water purification and are particularly effective at filtering out chlorine, sediment, volatile organic compounds and other impurities. Typically, the particles removed by carbon filters are between about 0.5 microns and about 50 microns. Other filters are well known and can be used with the provided methods.

Also exemplary of the purifiers that can be used in the provided methods are reverse osmosis purifiers, which use mechanical pressure to purify liquids, for example, water. In one example, the pressure forces the water through a semipermeable membrane to remove impurities.

Also exemplary of the purifiers that can be used in the provided methods are ion exchange purifiers, for example, an ion exchange purifier using a resin bed, for example, a zeolite resin bed, to replace salts, e.g. cations, for example, magnesium and calcium, with other cations, for example, sodium and potassium cations. Such purifiers can be purchased, for example, from Aquapure Filters, Clarkston, Mich.

In another example, an end product filter (e.g. a 100 micron FSI filter, Product Number BPEM 100-5GP). This filter is used to filter any impurities out of the final product (e.g. the final liquid nanoemulsion concentrate). Other filters are known and can be used with the provided methods.

c. Vessels for Mixing the Ingredients

One or more, typically two or more, vessels, for example, tanks, for example, water-jacketed tanks; pots; and/or beakers, for example, Pyrex® beakers, are used in the provided methods to contain the ingredient(s) of the liquid concentrates, for example, during mixing and/or heating or cooling. Typically, separate vessels (an oil phase tank and a water phase tank) are used for mixing and heating the ingredients of the oil phase and the water phase, prior to combining the two phases to form an emulsion. In another example, an additional vessel, for example, a holding and/or packaging tank, is used for holding and/or packaging the emulsion and/or for addition/mixing of additional ingredients to the emulsion.

A number of vessels are available for mixing ingredients. Typically, the vessels are cleaned, for example, rinsed, soaped and/or sanitized according to known procedures, prior to use and between uses.

In one example, typically used with the bench-top process, the vessel is a container, for example, a bench-top container, for example, flasks, beakers, for example, Pyrex® beakers, vials, measuring containers, bottles and/or other bench-top containers.

In another example, typically used with the scaled-up manufacturing process, the vessels are tanks, for example, water phase tanks, oil phase tanks and holding/packaging tanks. Typically, the tanks are equipped with one or more mixers, for example, a standard mixer and/or homogenizer, which are used to mix the ingredients added to the tank. In one example, the tank further is equipped with a heating and/or cooling device. For example, the tank can be a water-jacketed tank. The temperature of the water-jacketed tank is controlled through the water-jacket, for example, to heat the contents, for example, while mixing.

Exemplary of the tanks that can be used with the provided methods are water-jacketed tanks, for example, the Overly 550 Gallon water jacketed tank (Model 10576501G), which has a 550 gallon capacity and typically is used as a water-phase tank, the Schweitzers 450 gallon tank (Model #5214-C), which has a 450 gallon capacity and typically is used as an oil phase tank and the Royal 190 gallon water jacketed tank (Model 9977-5), which has a 190 gallon capacity and can be used as a water or oil phase tank when mixing smaller volumes. Other tanks are well known and can be used with the provided methods for mixing the concentrates, for example, the phases of the concentrates.

d. Mixers

Mixers are used in the provided methods to blend, mix and/or emulsify the liquid concentrates and/or various ingredients and/or phases of the liquid concentrates. In one example, the mixers are used to keep the ingredients and/or mixture circulating to maintain temperature, viscosity and/or other parameters of the mixture. Exemplary of the mixers that can be used in the provided methods are standard mixers, for example, standard mixers, which can be used, for example, to mix the ingredients in the water and/or oil phases, to maintain a homogeneous mixture while heating. Exemplary of the standard mixers is a LIGHTNIN® mixer (LIGHTNIN, Rochester, N.Y.), for example, Model Numbers XJC117 and ND-2. In one example, the LIGHTNIN® mixers are fixed-mount, gear drive high-flow mixers, for use with closed tanks. Another example of a standard mixer is a mixer sold by IKA®, for example, overhead IKA® mixers, for example, model Nos. RW-14 Basic and RE-16S, which are laboratory stirrers and can be used to mix ingredients, for example, to generate the oil and water phases. In one example, the mixer(s) are attached to the vessels, for example, the tanks, for example, mounted or clamped onto the tanks, for example, the top of the tanks. In another example, the mixers are placed in the vessels for mixing.

Also exemplary of the mixers used with the provided methods are homogenizers (also called shears), which typically are used to form the emulsion by emulsifying the oil and water phases after they are combined. The homogenizers typically provide high shear dispersion of solids and emulsification of immiscible liquids at high shear rates. Exemplary of the homogenizers that can be used in the provided methods are high-shear homogenizers, for example, reverse homogenizers sold by Arde Barinco, Inc., Norwood, N.J., for example, Model CJ-50, which is a 3600 rpm mixer having a 6 inch rotor diameter, a tip speed of 5575 ft/minute and an emersion depth of 33 inches and has six separate openings at the bottom and top, which concentrates the liquid into six chambers, reducing the surface volume and creating a shear effect; and Model CJ-4E, which is a 10,000 rpm mixer with fan-cooled motor, optimized for 1 to 5 gallon batch sizes, having a 1.875 inch rotor diameter, a tip speed of 4920 rpm and an immersion depth of 16 inches. Other homogenizers, for example, other reversible homogenizers sold by Arde Barinco Inc., can be used with the provided methods.

In one example, the homogenizer is attached to the top of the vessel, for example, the tank, for example, by clamps or by channel locks and an electrical hoist. In another example, the homogenizer is placed in the vessel. The Arde Barinco reversible homogenizers contain axial flow impellers, which create two distinct mixing actions, depending on direction. Downward "vortex flow" pulls solids from top and bottom of the mixture, while upward "umbrella flow" controls mixing at the highest shear and recirculation rates without splashing or incorporation of air. The reversible homogenizers typically are equipped with an adjustable baffle plate, which can be adjusted to control the type of mixing, for example at different times during emulsification. The speed of homogenization can also be adjusted accordingly to control or reduce the incorporation of air into the emulsion.

A number of additional mixers are well known and can be used with the provided methods. Exemplary of the mixers that can be used with the provided methods are shears, inline mixers/mixing, Ribbon, Plow/Paddle Blenders Forberg Mixers, Conveyors, Bag Dumps & Compactors, V-Blenders, Blade Mixers, Double Cone Mixers, Continuous Mixers, Speedflow Mixers, Batch Mixers, Double Ribbon Blenders, Paddle and Ribbon Mixers with Choppers, Plow Blenders/Turbulent Mixers, Fluidizing Forberg-Type Mixers, Air Mixers, Active Mixers, Passive Mixers, Top Entry Mixers, Side Entry Mixers, Static Mixers, Fixed Entry Mixers, Portable Mixers—direct and gear drive, Sanitary Mixers, Drum Mixers, Bulk Container (IBC) Mixers, Lab Stirrers, Variable Speed Mixers, dough mixer, vertical mixer, spiral mixer, twin arm mixer, fork mixer, double spiral mixer, all agitators, agitator mixers, Banbury Mixers, Rubber Mixers, Blondheim Mixers, Chum Mixers, Conical Mixers, Continuous Mixers, Disperser Mixers, Pan Mixers, Emulsifier Mixers, Hobart Mixers, Liquifier Mixers, Littleford Mixers, Meat Mixers, Plow Mixers, Mixmuller Mixers, Nauta Mixers, Oakes Mixers, Planetary Mixers, Pony Mixers, PUG Mixers, Ribbon Mixers, Ross Mixers, Rotary Mixers, Sigma Mixers, Single Arm Mixers, Tote Bin Mixers, Tumble Mixers, Vacuum Mixers, Turbolizer Mixers, Twin Shell Mixers, V-Type Mixers, Zig-Zag Mixers side arm mixers, hand-held mixers, stir rods, stir bars, magnetic mixers and overhead mixers, for example, mechanical and/or electric overhead mixers.

e. Heating Apparatuses

One or more, typically more than one, heating apparatuses are used in the provided methods to control the temperature of the ingredients, phases and/or concentrate, typically while mixing.

In one example, the heating apparatuses are water-jackets. In this example, the vessels used to mix the ingredients and/or emulsify the phases are water jacketed tanks. The water jacket can be controlled, for example, using a control panel, to adjust the temperature of the contents of the vessel.

Alternatively, other heating apparatuses can be used to heat the ingredients, phases, and/or concentrates. Exemplary of heating apparatuses that can be used with the provided methods are immersible and/or submersible heaters, for example, 12 KW or 13 KW sanitary heaters, which are food-grade heaters that are immersed into the tanks while mixing, typically for applications requiring high heat, for example, temperatures greater than about 60° C. or 60° C., or greater than 80° C. or about 80° C. Also exemplary of heating apparatuses are stoves, for example, propane stoves. Also exemplary of the heating apparatuses are hot plates, for example, the Thermolyne hot plate, model number 846925 and model number SP46615. Typically, the heater is capable of heating the mixture to between 45° C. or about 45° C. and 85° C. or about 85° C., for example, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85° C. Typically, the heater is capable of heating the mixture to 60° C. or 60° C., for example, providing low heat.

f. Cooling Apparatuses

One or more cooling apparatuses can be used with the provided methods, for example, to cool the ingredients during mixing, for example, to chill the mixture while emulsifying the oil and water phases. Exemplary of the cooling apparatuses are chillers, for example, recirculating coolers, which can be attached to the vessel, for example, remotely or by a tank mounted in the cooler, to recirculate fluid from the tank, through the chiller and back to the tank, in order to rapidly cool and maintain the temperature of the mixture during mixing. Exemplary of an open-loop chiller that can be attached to the tank and used with the provided methods are chillers sold by Turmoil, West Swanzey, N.H., for example, open or closed-loop coolers, for example, model No. OC-1000 RO. Other cooling apparatuses are well known and can be used with the provided methods.

Also exemplary of the cooling apparatuses are water baths and ice baths, for example, water baths and/or ice baths in which the vessel(s) are placed, for example, during homogenizing.

Typically, the cooling apparatus can be used to cool the liquid to between 25° C. or about 25° C. and 45° C. or about 45° C., for example, 25, 26, 27, 28, 29, 30, 31, 32, 33, 34, 35, 36, 37, 38, 39, 40, 41, 42, 43, 44 or 45° C., typically between 25° C. and 43° C., typically between 35° C. and 43° C., for example, 26.5° C. Typically, the cooling is rapid cooling, for example, cooling to between 25° C. or about 25° C. and 45° C. or about 45° C., for example, between 35° C. and 43° C., for example, 26.5° C., in between 15 minutes or about 15 minutes and 2 hours or about 2 hours, typically, between 30 minutes or about 30 minutes and 60 minutes or about 60 minutes, for example, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes.

g. Transfer Means

Transfer means are used with the provided methods to transfer liquid from one vessel to another vessel, for example, to transfer the contents of one or more vessels to one or more other vessels, for example, to transfer the water phase to the oil phase vessel (e.g. the oil phase tank) or to transfer the oil phase to the water phase vessel (e.g. the water phase tank), in order to form the emulsion. Exemplary of the equipment used for the transfer means are transfer pumps and associated accessories, for example, ball valves, sanitary fittings (for example, sanitary fittings sold by Granger, Inc., Lake Forrest Ill.) and transfer hoses (for example, hoses sold by Sani-Tech West, Oxnard, Calif.), for example, food grade hoses attached to the transfer pumps. Exemplary of the transfer pumps that can be used with the provided methods is the Teel Pump (Model 2P377B), Granger, Inc. Lake Forrest Ill., a self-priming pump having a power rating of 2 HP, 60 Hz voltage 208-230/460 AC, speed of 3450 rpm. Other pumps, for example, other self-priming pumps from Grainger, Inc., can be used as part of the transfer means in the provided methods. Alternatively, transfer means can include means for manually transferring the liquid to another vessel, for example, by pouring, pipetting and/or other well-known methods of manually transferring liquids.

h. Evaluation Equipment

Evaluation equipment is used to evaluate one or more properties of the compositions, for example, the phases of the compositions and/or the final concentrates. For example, evaluation equipment can be used to measure one or more parameters of the concentrates and/or the phases, for example, the temperature and the pH of the liquids. Exemplary of the evaluation equipment are pH meters and temperature meters. Exemplary of the pH/temperature meters is the pH and temperature meter sold by Hanna Instruments, (model number HI 8314), which can be used to measure the temperature and the pH of the mixture(s). Also exemplary of temperature meters are temperature probes, for example, digital and/or water-proof temperature probes, for example, temperature probes sold by Cooper-Atkins, Middlefield, Conn., for example, the digital waterproof temperature probe (Model #DPP400W) from Cooper-Atkins. Other evaluation equipment for evaluating liquids and/or emulsions is well known and can be used with the provided methods.

2. General Methods for Making the Liquid Nanoemulsion Concentrates

In general, the provided methods for making the concentrates include steps for generating phases (e.g. oil phase(s) and water phase(s)) and steps for combining and emulsifying the phases, to form the liquid nanoemulsion concentrates. In some examples, the methods include additional steps, such as evaluation, addition of further ingredients, packaging and filtering. The provided methods can be performed using a bench-top manufacturing process (typically for small batch sizes). Alternatively, the methods can be performed using a scaled-up manufacturing process (typically for larger batch sizes). Each of the provided concentrates can be made using either a scaled-up process or a bench-top process. In one example, after the concentrate first is made using the bench-top process, the method is scaled up to make larger quantities of the concentrate using the scaled-up process. When formulating the concentrates according to the provided methods, the initial concentrate typically is made by a bench-top method. In one example of the formulation methods, a selected formulation then is made using a scaled-up process. Any of the concentrates provided herein can be made with the provided methods, using either manufacturing process. Any method described herein, where the bench-top method is used, can be scaled-up for production of the concentrates using the scaled-up process.

Generally, the provided methods for making the liquid nanoemulsion concentrates include first generation steps, whereby one or more oil phases and one or more water phases are produced. Generation of the water phase and generation of the oil phase typically are performed in at least two separate vessels, for example, an oil phase vessel and a water phase vessel. Each of the generation steps typically includes a mixing step and a heating step, which can be performed simultaneously, sequentially in any order, or partially simultaneously.

To generate the water phase, water phase ingredient(s) (e.g. water and, in some examples, additional water phase ingredients) are added to a water phase vessel. The ingredient(s) are mixed, typically using a standard mixer, and heated, for example, using a heating apparatus. Typically, the water phase ingredients are heated to a low heat temperature, for example, to 60° C. or about 60° C. To make the oil phase, the oil phase ingredients (e.g. non-polar compound(s), surfactant(s) and, in some examples, other oil phase ingredient(s)) are added to an oil phase vessel. The oil phase ingredient(s) are mixed, typically using a standard mixer, and heated, for example, using a heating apparatus. Typically, the ingredients are heated to a low heat temperature, for example, to 60° C. or about 60° C. The mixing/heating of the water and oil phase can be performed simultaneously or sequentially, in any order. In one example, generation of the oil phase is performed subsequently to generation of the water phase, for example, to preserve the non-polar active ingredient, for example, to prevent its oxidation. Typically, both phases are heated to the desired temperature, for example, low heat temperature, and/or until the ingredients dissolve, prior to combining the oil and the water phases in a subsequent emulsification step.

In general, the methods further include an emulsifying step. For the emulsifying step, the oil and water phases are combined, for example, using one or more transfer means. The oil and water phases are emulsified, typically with mixing, typically homogenizing, for example, using high shear, in order to generate an emulsion (e.g. the liquid nanoemulsion concentrate). The emulsifying step can be performed in the water phase vessel, the oil phase vessel, or a separate vessel.

Typically, during the emulsifying step, the forming emulsion is cooled, for example, rapidly cooled, for example, using one or more cooling apparatuses. Typically, the cooling step is performed simultaneously with the emulsifying step. In one example, the cooling is performed until the emulsion reaches a temperature of between 25 or about 25° C. and 43 or about 43° C.

The provided methods can include additional steps, for example, evaluation steps, steps for adding additional ingredients, purification (e.g. filtration) steps, and/or packaging/holding steps, as detailed below.

a. Generating the Water Phase

Typically the water phase ingredients are weighed and/or measured, for example, using one or more scales (e.g. one or more of the scales described herein), before addition to the water phase vessel (e.g. any vessel described herein). In one example, the amount of each ingredient to be added to the water phase vessel is determined according to the provided methods for formulating the concentrates. Typically, the desired concentration, by weight (w/w), of the final nanoemulsion concentrate is used to calculate the amount of each water phase ingredient that is added to the water phase vessel. Alternatively, the desired volume per weight, volume per volume or weight per volume can be used to calculate the correct amount of an ingredient to be measured and added to the vessel.

In one example, impurities in the water, for example, city water, are removed using one or more purifiers (e.g. one or more purifiers as described herein) above, before adding the water to the water phase tank. In one example, the water is purified by passage through the following purifiers, sequentially: a carbon filter, an ion exchange purifier, a reverse osmosis purifier and an end-point filter, for example, a 100 micron end-point filter, before being added to the water phase vessel.

Typically, the water phase ingredient(s) are mixed in the water phase vessel using a mixer (e.g. any of the standard mixers described herein or a homogenizer) and heated, typically simultaneously or, in part, simultaneously, using a heating apparatus (e.g. any of the heating apparatuses described herein). Typically, the water phase is heated such that the water phase ingredients reach a low heat temperature, for example, between about between 45° C. or about 45° C. and 85° C. or about 85° C., for example, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85° C., typically, 60° C. or 60° C., for example, to prevent oxidation of the non-polar ingredients and/or maintain the stability of the ingredients. Typically, mixing and/or heating of water phase ingredients in the water phase vessel is continued, for example, prior to combining the water phase and the oil phase. In one example, the water phase is mixed and/or heated until the water phase ingredients have dissolved. Typically, the temperature of the water phase is maintained with mixing prior to combining the oil and water phases.

i. Water Phase Ingredients

The water phase includes water and, in some examples, other water phase ingredients. Typically, water phase ingredients are hydrophilic and/or amphipathic ingredients of the liquid nanoemulsion concentrate. For example, oils and other lipophilic ingredients typically are not added to the water phase. Certain ingredients, for example, ingredients having hydrophobic and hydrophilic moieties, for example, surfactants and co-surfactants, can be added to either the oil or the water phase, or to the oil and the water phase. Exemplary of water phase ingredients are water, typically filtered water; emulsion stabilizers; pH adjusters, for example, phosphoric acid and/or citric acid; flavors; surfactants; co-surfactants, for example, phosphatidylcholine and/or quillaja saponin; preservatives and other water phase ingredients.

Water phase ingredients can be added to the water phase simultaneously and/or sequentially, in a specific order. In one example, one or more water phase ingredients is added first and heated, prior to addition of further ingredient(s). In one example, when the water phase ingredients include water and an emulsion stabilizer, these ingredients are added sequentially, in the following order: 1) water; 2) emulsion stabilizer. In another example, when the water phase ingredients include a surfactant, water and an emulsion stabilizer, these ingredients are added to the water phase vessel sequentially, in the following order: 1) surfactant; 2) water; 3) emulsion stabilizer. Alternatively, the water phase ingredients can be added in any other order. Typically, when the water phase includes a surfactant, particularly when the surfactant is a surfactant that is solid at room temperature, for example, polysorbate 80 or polysorbate 80 analog surfactant, the surfactant is the first water phase ingredient added to the water phase vessel. Typically, when the water phase ingredients include an emulsion stabilizer, the emulsion stabilizer is the last ingredient added to the water phase vessel.

b. Generating the Oil Phase

Typically the oil phase ingredient(s) are weighed and/or measured, for example, using one or more scales (e.g. one or more of the scales described herein), before addition to the oil phase vessel (e.g. any of the vessels described herein). In one example, the amount of each oil phase ingredient to be added is determined according to the provided methods for formulating the concentrates. Typically, the desired concentration, by weight (w/w), of the final nanoemulsion concentrate is used to calculate the amount of each oil phase ingredient that should be added to the oil phase vessel. Alternatively, the volume per weight, volume per volume or weight per volume can be used to calculate the correct amount of an ingredient to be measured and added to the vessel.

Typically, the oil phase ingredients are mixed in the oil phase vessel using a mixer (e.g. any of the standard mixers described herein or a homogenizer) and heated, typically simultaneously, using a heating apparatus (e.g. any of the heating apparatuses described herein). Typically, the oil phase is heated such that it reaches a low heat temperature, for example, between 45° C. or about 45° C. and 85° C. or about 85° C., for example, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85° C., typically 60° C. or 60° C., for example, to prevent oxidation of the non-polar ingredients and/or maintain the stability of the ingredients. In one example, one or more of the oil phase ingredients are mixed and heated according to the provided methods, prior to addition of the rest of the oil phase ingredients. For example, the non-polar compound can be mixed and heated with one or more solvent, for example, an oil, for example, flaxseed oil and/or Vitamin E oil, until the non-polar compound is dissolved in the oil, prior to addition of the other oil ingredients. Typically, the oil phase ingredients are mixed in the oil phase vessel until dissolved. Typically, the temperature of the oil phase is maintained with mixing prior to combining the oil and water phases.

In some examples the oil and/or the water phase can be made in more than one vessels, for example, by mixing one or more of the oil phase ingredients in one vessel and mixing the one or more other oil ingredients in another vessel. In this example, the mixed oil phase ingredients in the separate vessels either can be mixed together prior to emulsifying with the water phase, or alternatively, can be added separately, during emulsification, to the water phase.

i. Oil Phase Ingredients

The oil phase includes the non-polar compound, for example, the non-polar active ingredient and, in some examples, other oil phase ingredients. Typically, oil phase ingredients include one or more lipophilic and/or amphipathic ingredients of the liquid nanoemulsion concentrate. Oil phase ingredients typically do not include aqueous ingredients or hydrophilic ingredients. Certain ingredients, for example, ingredients having hydrophobic and hydrophilic moieties, for example, surfactants and co-surfactants, can be added to either the oil or the water phase, or to the oil and the water phase. Exemplary of ingredients used in the oil phase of the provided concentrates are non-polar compounds, for example, non-polar active ingredients, including any of the non-polar active ingredients provided herein; emulsion stabilizers; pH adjusters, for example, phosphoric acid and/or citric acid; surfactants; co-surfactants, for example, phosphatidylcholine and/or quillaja saponin; preservatives; and oils, for example, solvents and other oil phase ingredients.

Oil phase ingredients can be added to the oil phase simultaneously and/or sequentially, for example, in any order or in a specific order. In one example, one or more oil phase ingredients is added first and heated, prior to addition of further ingredient(s). In one example, when the oil phase ingredients include a surfactant, a preservative, a solvent, a co-surfactant, and a non-polar compound, these ingredients are added sequentially, in the following order: 1) surfactant; 2) preservative; 3) solvent; 4) co-surfactant; 5) non-polar compound; and 6) emulsion stabilizer. In another example, when the oil phase ingredients include a surfactant, a preservative and a non-polar compound, the ingredients are added sequentially, in the following order: 1) surfactant; 2) preservative; 3) non-polar compound. In another example, when the oil phase ingredients include a surfactant, a preservative, a non-polar compound and an emulsion stabilizer, the ingredients are added sequentially, in the following order: 1) surfactant; 2) preservative; 3) non-polar compound; and 4) emulsion stabilizer. Alternatively, the oil phase ingredients can be added in a different order, for example, any order. Two or more oil phase ingredients can be added simultaneously.

Typically, when the oil phase includes a surfactant, particularly when the surfactant is a surfactant that is solid at room temperature, for example, polysorbate 80 or polysorbate 80 analog surfactant, the surfactant is the first oil phase ingredient added to the oil phase vessel. Typically, when the oil phase ingredients include an emulsion stabilizer, the emulsion stabilizer is the last ingredient added to the oil phase vessel. Typically, the non-polar compound either is the last ingredient added to the oil phase vessel, or is added immediately prior to addition of the emulsion stabilizer, which is the last ingredient added to the oil phase vessel.

c. Combining and Emulsifying the Oil Phase and the Water Phase

Generally, in the provided methods, following the generation of the oil phase and the water phase, the oil and water phases are combined, for example, using one or more transfer means (e.g. any of the transfer means described herein). The combined phases are emulsified, for example, by mixing, for example, homogenizing, to form an emulsion (e.g. the liquid nanoemulsion concentrate). Typically, the phases are mixed during the combining and the emulsifying steps, for example, using a homogenizer (e.g. any of the homogenizers described herein). In one example, the oil and water phases (e.g. the forming emulsion) further are cooled, for example, rapidly cooled, during the emulsifying and/or combining steps.

i. Combining the Oil and Water Phases

In order to emulsify them, the oil and water phases first are combined, typically by transfer, using one or more transfer means (e.g. any of the transfer means described herein). In one example, the oil phase is transferred to the water phase vessel. In another example, the water phase is transferred to the oil phase vessel. In another example, a plurality of oil phases or water phases are transferred to a water phase or an oil phase vessel. In another example, the water phase(s) and the oil phase(s) are transferred to another vessel, for example, an emulsification vessel.

Any transfer means can be used to combine the phases. For example, any means for transferring the contents of one vessel to another vessel as described above, for example, transfer pumps and associated equipment, for example, sanitary fittings, hoses and/or ball valves; and manual transfer means, for example, pouring and/or pipetting means or other known transfer means. In some examples, the phases are kept clean, for example, sterile during transfer, for example, by using transfer means with sanitary fittings and/or combining the phases in a sterile environment.

ii. Emulsifying the Oil and Water Phases

Simultaneous to and/or subsequent to the combination of the phases, the phases are mixed (e.g. homogenized), for example, using a homogenizer (e.g. any of the described homogenizer), to form an emulsion. Typically, the emulsifying is performed in the vessel containing the combined liquids, for example, the oil phase or the water phase vessel. For this emulsifying step, the oil and water phases are mixed, for example, after the combining step, typically during and after the combining step, using a mixer that is capable of emulsifying liquids, for example, a homogenizer, for example, a reversible homogenizer. Typically, the liquids are homogenized using the mixer (e.g. homogenizer) at low speed, for example, low rpm, for example, between 850 or about 850 rpm and 1200 or about 1200 rpm, for example, 850, 900, 950, 1000, 1050, 1100, 1150 or 1200 rpm. Lower speeds can reduce the incorporation of air into the nanoemulsion. In some examples, the homogenization can be performed at speeds less than 850 rpm, such as, for example, between 25 or about 25 rpm and 50 rpm or about 50 rpm, for example at or about 30 rpm, to further reduce incorporation of air into the nanoemulsion.

The liquids typically are mixed, continuously or intermittently, until the liquids are emulsified, for example, in a nanoemulsion. In one example, the mixing speed is maintained in order to emulsify the oil and water phases. In one example, the baffle plate of the mixer is adjusted, for example, by moving the baffle plate further down into the mixture or further up out of the mixture, to control the type of mixing, for example, to switch from downward flow to upward flow and vice versa, during mixing of the emulsion. In another example, the homogenizer can be adjusted to increase or decrease shear or to maintain the shear at a particular speed. Methods for homogenizing oil and water phases are well known and other methods can be used to homogenize the oil and water phases in the provided methods.

iii. Cooling

Typically, the emulsion is cooled during mixing, for example, by rapid cooling. In one example, the emulsion is cooled to promote stability of the emulsion and emulsification of the phases, for example, by preventing or minimizing oxidization, for example, oxidization of the non-polar compound. The cooling, for example, rapid cooling, typically is performed using one or more cooling apparatuses, for example, any of the cooling apparatuses described herein or any known cooling apparatus. In one example, the cooling apparatus is a recirculating cooler. In another example, the cooling apparatus is a water bath or an ice bath. In one example, when the apparatus is a recirculating cooler, fluid from the vessel being used for the emulsifying step is recirculated through the cooler, and then back to the vessel, to rapidly cool and maintain the temperature of the mixture during mixing. Typically, the forming emulsion is mixed and cooled until the phases are emulsified and the temperature reaches between 25 or about 25° C. and 43 or about 43° C., for example, 25, 26, 27, 28, 29, 30, 31, 32, 33, 34, 35, 36, 37, 38, 39, 40, 41, 42 or 43° C. Typically, when the cooling is rapid cooling, the temperature is reached in less than 2 hours or about 2 hours, typically less than 1 hour or about 1 hour, for example, in at least between 30 minutes or about 30 minutes and 60 minutes or about 60 minutes, for example, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes.

Once the oil and water phases have been emulsified, thereby forming an emulsion, for example, a liquid nanoemulsion concentrate, the emulsion can be used, for example, in the provided dilution methods to make a liquid dilution composition, for example, a beverage, containing the concentrate. Alternatively, one or more additional steps can be performed before using the concentrate.

d. Additional Steps

Typically, one or more additional steps is carried out, following emulsifying the phases, prior to use of the concentrate. For example, the emulsion can be evaluated (e.g. by measuring pH and/or temperature of the concentrate). In another example, one or more additional ingredients can be added to the emulsion. In another example, the nanoemulsion concentrate is transferred to a holding vessel or a packaging vessel, for example, a holding/packaging vessel, for example, a holding/packaging tank. In another example, the nanoemulsion is purified, for example, filtered, prior to use. In one example, addition of additional ingredients, evaluation and/or purification, can be performed in the holding/packaging vessel. Other additional steps can be performed prior to use.

i. Additional Ingredients

In one example, additional ingredients, for example pH adjusters and/or flavors, can be added to the emulsion after it is formed. In one example, citric acid and/or phosphoric acid is added to adjust the pH, for example, until the pH reaches a pH between 2.5 and 3.5, typically, between 2.6 or about 2.6 and 3.2 or about 3.2, for example, 2.6, 2.7, 2.8, 2.9, 3.0, 3.1, or 3.2. In another example, one or more flavors is added to the concentrate, for example, to improve the taste and/or smell of the concentrate and/or beverages containing the concentrate. In another example, additional water can be added to the emulsion, for example, in the case of evaporation, to bring the concentrate to the appropriate volume. Other additional ingredients also can be added to the emulsion. Typically, the additional ingredients are added to the vessel containing the emulsion, for example, the water phase vessel, the oil phase vessel, the emulsion vessel, or another vessel, for example, a holding/packaging vessel. Typically, the emulsion is mixed (e.g. using any of the described mixers, typically standard mixers or a homogenizer), while the additional ingredients are added.

ii. Evaluation of the Concentrate

Typically, the concentrate is evaluated prior to use. Typically, the pH and/or temperature are measured, for example, using a pH and temperature meter. In one example, the pH and/or temperature are evaluated after additional ingredients have been added. In one example, further ingredients can be added to adjust the parameters after evaluation.

iii. Filtering the Concentrate

In one example, the concentrate is purified (e.g. with any of the described purifiers), for example, using an end product filter, prior to use of the concentrate, for example, prior to diluting the concentrate in an aqueous medium.

3. Bench-Top Process

In one example of the provided methods for making the liquid nanoemulsion concentrates, the steps of the methods are performed using a bench-top manufacturing process, which is performed on a bench, counter, table or other surface. Typically, the bench-top process is used to make emulsions having relatively smaller volumes than those made with the scaled-up process, for example, volumes less than 1 L or about 1 L or less than 1 gallon or about 1 gallon, for example, less than about 500 mL, for example, 1000, 900, 800, 700, 600, 500, 450, 400, 350, 300, 250, 200, 150, 100, 50 or less.

For the bench-top process, the equipment typically is sufficiently compact to be used on a bench top or other similar surface, typically sufficiently compact to be moved, for example, lifted, by the artisan using the methods. For example, the vessels, for example, water phase vessels, oil phase vessels, holding vessels, and packaging vessels typically are bench-top vessels, for example, flasks, beakers, vials, measuring containers, bottles and/or other bench-top containers. In one example, the vessels in the bench-top process is a Pyrex® beaker. Typically, the mixers are mixers that can be used in the bench-top vessels, for example, standard mixers, including hand-held mixers, stir rods, stir bars, magnetic mixers and overhead mixers, for example, mechanical and/or electric overhead mixers and/or other mixers that can be used in the vessels. Exemplary of appropriate bench-top mixers are standard mixers, for example, standard mixers sold by IKA®, for example, overhead IKA® mixers, for example, model Nos. RW-14 Basic and RE-16S, which are laboratory stirrers and can be used to mix ingredients, for example, to generate the oil and water phases. Also exemplary of appropriate bench-top mixers are homogenizers, for example, reversible homogenizers, including The Arde Barinco reversible homogenizer, Model no. CJ-4E, which can be used to emulsify the phases. Typically, the heating apparatuses are those that can be used with the bench-top vessels, for example, hot plates. The cooling apparatuses typically are apparatuses suited for use with the smaller bench-top vessels, for example, ice baths and/or water baths into which the vessels can be placed, for example, for rapid cooling. The evaluation means used in the bench-top process, for example, the temperature and/or pH meters, typically are capable of being placed in the bench-top vessels.

Generally, for the bench-top process, the oil phase and water phase are generated by mixing and heating in separate bench-top vessels, for example, flasks, beakers, vials, measuring containers, bottles and/or other bench-top containers. The mixing typically is performed using an appropriate bench-top mixer, for example, a standard mixer, such as a hand-held mixer, stir rod, stir bar, magnetic mixer and/or overhead mixer, for example, the mixer sold by IKA®, for example, overhead IKA® mixers, for example, model Nos. RW-14 Basic and RE-16S, which are laboratory stirrers. Typically, heating the oil and water phases is performed using a heating apparatus appropriate to the bench-top method, for example, a heating apparatus that one or more of the vessels can be placed upon, for example, a hot plate. For combining the oil phase and the water phase, one or more phases, typically one phase, typically is transferred manually to another vessel, for example, by pouring, pipetting and/or another manual transfer means. For emulsifying the oil and water phases, a reverse homogenizer typically is used. For cooling the forming emulsion, for example, for rapidly cooling the emulsion, a cooling apparatus appropriate to the bench-top method typically is used, for example, a cooling apparatus that the vessel can be placed upon or inside, for example, a water bath or an ice bath.

4. Scaled-Up Manufacturing Process

In another example of the provided methods for making the liquid nanoemulsion concentrates, the steps of the methods are performed using a scaled-up manufacturing process, which typically is used when making emulsions having relatively larger volumes than those made with the bench-top process, for example, volumes greater than 1 L or about 1 L or greater than 1 gallon or about 1 gallon, for example, greater than about 500 mL, for example, at least 0.5 L, 1 L, 2 L, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, 500, 550, 600, 650, 700, 800, 900, 1000 or more gallons. In general, equipment used for the scaled-up process is compatible with these larger volume batches (batch sizes) of the concentrates. For example, the vessels typically are tanks, for example, water jacketed tanks, which are equipped with water jackets that can be used as heating apparatuses to heat the oil and water phase ingredients during generation of the oil and water phases. The water jackets typically are controlled via control panels. Similarly, the transfer means typically include transfer pumps and associated fittings, for example, ball valves and hoses. Exemplary of mixers that are used in the scaled-up process are standard mixers (for example, mounted mixers, for example LIGHTNIN® mixers, for example, Model XJC117 (a fixed-mount, gear drive high-flow mixer, and Model ND2. An exemplary scaled-up process is set forth in FIG. 1 and described in this section, below. The provided methods for making the concentrates can be performed using this exemplary scaled-up process, or any variation of the scaled-up process, for example, eliminating one or more steps of the exemplary process, adding one or more steps according to the provided method, and/or substituting steps and/or equipment according to the methods provided herein.

FIG. 1 sets forth a an exemplary scaled-up process 100 for making the liquid concentrate. This exemplary scaled-up process includes the following steps:

a. Water Purification

Water 101, for example, city water, is purified before addition to the water phase vessel. As shown in FIG. 1, water purification in this example is performed by passing the water through the following purifiers, sequentially, in the following order: a carbon filter 105, ion exchange equipment 106, reverse osmosis equipment 107, a 100 micron end-point filter 108, and a 50 micron point-of-use filter 109.

b. Generation of the Water Phase and Oil Phase:

To generate the water phase, the water and any additional water phase ingredients are weighed/measured and added to the water phase vessel. In this example, set forth in FIG. 1, the water phase vessel is a water phase tank 103. Typically, in the scaled-up method, the water phase tank is a water-jacketed tank. The water phase ingredient(s) are mixed using a standard mixer 111, for example, a LIGHTNIN® mixer (for example, model no. XJC117, a fixed-mount gear drive high-flow mixer), attached to the tank, for example, mounted on the top of the tank. In this example, the heating apparatus, for heating the water phase ingredients during water phase generation, is the water jacket of the water-jacketed tank; temperature on the water-jacket is controlled via a control pane. The water phase is generated with mixing and heating, typically to low heat (e.g. 60° C.), according to the provided methods.

To generate the oil phase, the oil phase ingredient(s) are weighed/measured and added to the oil phase vessel. In this example, set forth in FIG. 1, the oil phase vessel is an oil phase tank 102. Typically, the oil phase tank in the scaled-up method is a water-jacketed oil phase tank. The oil phase ingredients are mixed using a standard mixer 111, for example, a LIGHTNIN® mixer (e.g. model ND2), attached to the oil phase tank, for example, mounted on the tank. In this example, the heating apparatus, for heating the oil phase ingredients during water phase generation, is the water jacket of the water-jacketed tank; temperature on the water-jacket is controlled via a control pane. The oil phase is generated with mixing and heating, typically to low heat (e.g. 60° C.) according to the provided methods.

c. Combining and Emulsifying the Phases

In this example, set forth in FIG. 1, once the oil and water phases reach 60° C., and after oil phase components have dissolved, the oil and water phases are combined, via transfer, and emulsified, via homogenization.

Combining the phases is performed by transferring the oil phase to the water phase vessel, via transfer means 112, which include a transfer pump (e.g. a Teel pump, model 2P377B, sold by Granger, Inc.), sanitary fittings, transfer hose(s) (e.g. food grade hoses sold by Sani-Tech West) and ball valve(s). In the example set forth in FIG. 1, to begin the combining/emulsifying steps, a homogenizer 110 (e.g. an Arde Barinco, Inc. reversible homogenizer), mounted on the water phase tank, is turned on for homogenization of the mixture. The ball valves then are opened and the transfer pump turned on, thereby effecting transfer of the oil phase liquid to the water phase tank via the transfer hose(s). As the phases are combined, the mixture is homogenized by continued mixing with the homogenizer 110. The homogenizer can be adjusted, for example, by adjusting the baffle plate on the homogenizer to achieve and maintain an emulsion, for example, by moving the baffle plate further into the forming emulsion and/or further out of the forming emulsion.

d. Cooling

In the example illustrated in FIG. 1, during the emulsifying step, the forming emulsion is cooled, typically rapidly cooled, by repeatedly passing the forming emulsion through a recirculating cooler 115 (e.g. Model No. OC-1000 RO, sold by Turmoil, West Swanzey, N.H.), which is attached to the water phase tank. Homogenization continues during the cooling step, for example, at between 850 and 1200 rpm, or at lower speeds, such as for example, 30 rpm. The cooling continues, for example, until the temperature of the emulsion reaches between 25° C. and 43° C., for example for between about 30 and about 60 minutes.

e. Additional Steps

In the example set forth in FIG. 1, additional steps are performed following the emulsification of the oil and water phases.

The emulsion is transferred, via transfer means 112, which include a transfer pump (e.g. a Teel pump, model 2P377B, sold by Granger, Inc.), sanitary fittings, transfer hose(s) (e.g. food grade hoses sold by Sani-Tech West) and ball valve(s), to a holding/packaging tank 104. Transfer is performed by turning on the transfer pump and opening the ball valves. Additional ingredients can be added, for example, pH adjusters, for example, while monitoring pH, sufficient to bring the nanoemulsion to an appropriate pH, for example, between about 2.6 and 3.2. Flavors can also be added. The additional ingredients are mixed into the concentrate using a standard mixer 111. The addition and mixing of additional ingredients, and/or evaluation can be performed in the holding/packaging tank 104; alternatively it can be performed prior to transfer to the holding/packaging tank, for example, in the water phase tank 103.

Variations of this exemplary scaled-up process (FIG. 1) also can be performed using the provided methods, to make the concentrates. For example, by elimination and/or modification of one or more steps and/or equipment, according to the general methods provided herein.

D. METHODS FOR MAKING THE LIQUID DILUTION COMPOSITIONS CONTAINING THE DILUTED CONCENTRATES

Also provided herein are methods for diluting the liquid nanoemulsion concentrates to make liquid dilution compositions, typically, aqueous liquid dilution compositions, containing the non-polar compounds. Generally, the nanoemulsion concentrate is diluted into an aqueous medium, for example, a beverage, for example, soda, water milk, juice, fitness drinks, nutritional beverage, nutritional supplement, or other aqueous food or beverage. The concentrate and the aqueous medium can be mixed, for example, by stirring and/or blending or by any known mixing means. The concentrate disperses into the aqueous medium to form an aqueous liquid dilution composition, for example, a clear or partially clear aqueous liquid dilution composition. The aqueous liquid dilution composition can be evaluated, for example, to assess the clarity, taste, smell, and/or stability of the liquid.

In one example, the liquid nanoemulsion concentrate is diluted in the aqueous medium, for example, water by heating the aqueous medium, for example, by heating the aqueous medium, for example, to at least 40° C. or at least about 40° C., for example, 41, 42, 43, 44, 45, 46, 47, 48, 49, 50 or more ° C., for example, 48.9° C. In this example, the liquid nanoemulsion concentrate is added, at an appropriate dilution, as described herein, to the heated aqueous medium, and stirred until dispersed or dissolved in the solution. The resulting liquid dilution composition can then be cooled, for example, to room temperature, for example, 25° C. or about 25° C. Following dilution, the aqueous liquid dilution composition can be packaged, for example, by transferring to containers, for example, vials or beverage containers. In one example, a portion of the liquid dilution composition is transferred to vials for analysis, for example, evaluation of properties, such as clarity, turbidity, taste, smell, ringing, crystal formation and/or other properties.

Exemplary of equipment used for diluting the liquid nanoemulsion concentrates to form the liquid dilution compositions containing the diluted concentrates are beakers, for example, Pyrex® glass beakers, hot plates, for example, the Thermolyne hot plate, model number 846925 or model number SP46615, stir rods, temperature meters, for example, temperature probes, for example, Cooper Temperature Probes (model no. DPP400W) and scales, for example, the OHUAS 2.0 Kg scale (Model # CS2000) and/or the Sartorius Analytical Scale (model BA110S.

1. Dilutions

Typically, the provided concentrates can be diluted into aqueous media to form aqueous liquid dilution compositions over a wide range of dilutions. In one example, the concentrate can be diluted so that the aqueous liquid dilution composition contains between 0.05 g or about 0.05 g and 10 g or about 10 g, typically between 0.05 g and 5 g, of the liquid concentrate per 8 fluid ounces of the liquid, at least 8 fluid ounces of the liquid or less than 8 fluid ounces of the liquid, or per single serving of the liquid. For example, the concentrate can be diluted so that the aqueous liquid dilution composition contains 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1 g, 2 g, 3 g, 4 g, 5 g, 6 g, 7 g, 8 g, 9 g, or 10 g of the concentrate per 8 fluid ounces, about 8 fluid ounces, or at least 8 fluid ounces or at least about 8 fluid ounces of the aqueous medium, for example 8, 9, 10, 11, 12, 13, 14, 15, 16, 17, 18, 19, 20, 25, 30, 35, 40, 45, 50, 100, 200 or more fluid ounces, of aqueous medium.

In another example, the concentrate is diluted so that the aqueous liquid dilution composition contains between 1 mL or about 1 mL and 10 mL or about 10 mL of the liquid concentrate, for example, 1 mL, 2 mL, 3 mL, 4 mL, 5 mL, 6 mL, 7 mL, 8 mL, 9 mL or 10 mL of the concentrate, per 8 fluid ounces, about 8 fluid ounces, at least 8 fluid ounces or at least about 8 fluid ounces, or less than 8 fluid ounces or less than about 8 fluid ounces, or per serving size, of the aqueous medium, for example 8, 9, 10, 11, 12, 13, 14, 15, 16, 17, 18, 19, 20, 25, 30, 35, 40, 45, 50, 100, 200 or more fluid ounces, of aqueous medium.

In another example, the liquid concentrate is diluted so that the aqueous liquid dilution composition contains at least 10 mg or about 10 mg, typically at least 25 mg or about 25 mg, typically at least 35 mg or about 35 mg, of the non-polar compound, for example, the non-polar active ingredient, per 8 fluid ounces (0.236588 liters) or about 8 fluid ounces, at least 8 fluid ounces or at least about 8 fluid ounces (0.236588 liters) of the aqueous medium, or less than 8 ounces or less than about 8 ounces, or per serving size, of the aqueous medium; for example, 10, 11, 12, 13, 14, 15, 16, 17, 18, 19, 20, 21, 22, 23, 25, 25, 26, 27, 28, 29, 30, 31, 32, 33, 34, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000 mg, or more, of the non-polar compound per at least 8 fluid ounces (0.236588 liters) or at least about 8 fluid ounces of aqueous medium.

2. Analyzing the Aqueous Liquid Dilution Compositions Containing the Liquid Concentrates Properties of the aqueous liquid dilution compositions containing the liquid concentrates can be evaluated using a number of different evaluation means. For example, the clarity; desirability for human consumption, for example, pleasant taste, and/or smell, for example, lack of "fishy" taste/smell, lack of "ringing" and lack of crystal formation; stability, for example, lack of oxidation, "ringing," precipitation and/or visible phase separation, over time; and safety for human consumption, can be evaluated. Several of these properties can be evaluated empirically, for example, by observing the liquids immediately or over time, or by smelling and/or tasting the liquids. In one example, after evaluation of the aqueous liquid dilution compositions, the concentrates are re-formulated to adjust one or more parameters. In another example, the dilution factor can be adjusted.

a. Clarity/Turbidity

Clarity of the aqueous liquid dilution compositions can be evaluated using one or more of several approaches, or example, empirical observation, measurement of particle size and/or measurement of a turbidity value. The measurement can be qualitative or quantitative. In one example, a particular quantitative or qualitative clarity value is specified. In another example, the clarity of a liquid can be expressed in relation to the clarity of another liquid, for example, an aqueous liquid dilution composition made according to the provided methods, or a beverage, for example, a beverage that does not contain the liquid concentrate. In this example, the liquid can be as clear as, less clear, or more clear than the other liquid. For example, an aqueous liquid dilution composition containing the liquid concentrate diluted in a beverage can be as clear or about as clear as the same beverage that does not contain the concentrate. Either type of evaluation can be done qualitatively, for example, by empirical evaluation, or quantitatively, for example, by taking a measurement of particle size or turbidity.

i. Empirical Evaluation

In one example, the clarity/turbidity of the aqueous liquid dilution composition is evaluated qualitatively, for example, by observation. In one example, a liquid is considered clear if it does not have a cloudy appearance and/or if it contains no particles or few particles that are observable with the naked eye. In another example, the liquid can be considered relatively clear or relatively turbid based on comparison to other liquids, for example, water, fruit juice, soda, and/or milk and/or other aqueous liquid dilution composition(s) made according to the provided methods. For example, the aqueous liquid dilution composition can be as clear or about as clear as water or another liquid, for example, a beverage. For example, the liquid containing the liquid concentrate diluted in a beverage can be as clear or about as clear as the beverage that does not contain the liquid concentrate. In a related example, the liquid can be clear or partially clear when there is no substantial difference, for example, no observable difference, between the aqueous liquid dilution composition containing the concentrate and the aqueous medium that does not contain the concentrate. A clear liquid is not necessarily colorless. For example, a yellow liquid that contains no (or few) visible particles or cloudiness can be clear. In another example, the lack of crystal formation or of "ringing" can be indicative of a clear liquid.

ii. Particle Size

In another example, clarity/turbidity are assessed by quantitatively measuring particle size and/or number of particles, in the aqueous liquid dilution composition. In this example, the clarity can be expressed as a numerical representation of the particle size, or as a comparison to the particle size of another liquid.

Methods for measuring particle size of liquids are well known. Any method for measuring particle size can be used, provided that it is sensitive to the particle size in the expected and/or appropriate ranges of the provided aqueous liquid dilution compositions. For example, particle size analysis is available commercially, for example, from Delta Analytical Instruments, Inc., North Huntingdon, Pa. In one example, the particle size of the aqueous liquid dilution composition is measured, for example, by Delta Analytical Instruments, Inc., using a light-scattering analyzer, for example, a dynamic light scattering analyzer, for example, the Horiba® LB-550, which can measure particle sizes within a range of 0.001 micron to 6 micron and uses a Fourier-Transform/Iterative Deconvolution technique for reporting data and can measure sample concentrations from ppm to 40% solids; the Horiba® LA-920, which is a laser light-scattering instrument having an He—Ne laser and a tungsten lamp that can determine particle sizes from 0.02 micron to 2000 micron using Mie Theory; and other analyzers available from Delta Analytical Instruments, Inc.

Alternatively, particle size can be measured by viewing the liquid under a microscope under magnification, for example, a 640× magnification. Particle size then can be measured by comparison to a measuring standard, for example, a ruler, which also is viewed under the magnification. In one example, particles about 25 nm or greater than about 25 nm are visible, while particles less than 25 nm are not visible, for example under a 640× magnification.

iii. Turbidity Measurement

In another example, the clarity/turbidity of the liquid is evaluated and/or expressed using a turbidity measurement, for example, Nephelometric Turbidity Units (NTU). In this example, turbidity is measured optically, to obtain a value indicating the cloudiness or haziness of the liquid, which correlates with the number and size of particles suspended in the liquid. The more clear a liquid is, the lower its turbidity value. Turbidity can be measured optically, for example, using a nephelometer, an instrument with a light and a detector. The nephelometer measures turbidity by detecting scattered light resulting from exposure of the aqueous liquid dilution composition to an incident light. The amount of scattered light correlates with the amount and size of particulate matter in liquid, and thus, the clarity. For example, a beam of light will pass through a sample having low turbidity with little disturbance, creating very little scattered light, resulting in a low turbidity (NTU) value reading. Other methods for measuring turbidity can be used, including commercial services for measuring turbidity, for example, the services available through ACZ Laboratories, Inc., Steamboat Springs, Colo.

The following examples are included for illustrative purposes only and are not intended to limit the scope of the invention.

E. EXAMPLES

Example 1

General Exemplary Procedures Used to Make the Liquid Nanoemulsion Concentrates Using Exemplary Formulations in Examples 2-3

Tables 2(A-E) and 3A, below, set forth ingredients that were used to make a plurality of liquid nanoemulsion concentrates, described in further detail in Examples 2 through 3 (and subsections thereof), according to the provided methods. Each of the nanoemulsion concentrates contained one or more non-polar active ingredients.

Each of Tables 2(A-E) and 3A sets forth the milligrams (mg) per serving (serving size is indicated) of each ingredient in the concentrate, the percentage, by weight (of the total concentrate), for each ingredient and the amount (g) of each ingredient per batch of the indicated batch size (g). Also indicated in each table, in the "phase" column, is whether each ingredient was added to the water phase ("water"), the oil phase ("oil") or was added later, to the emulsion that was formed by emulsifying the oil and water phases ("emulsion").

Each of the liquid nanoemulsion concentrates set forth in Examples 2-3 was made using a bench-top process according to the provided methods, as described in this Example. Alternatively, each of these concentrates can be made by scaling up the bench-top process, to make the concentrates using a scaled-up manufacturing process of the provided methods, for example, to make larger batch sizes of the concentrates in the following Examples. Accordingly, each of the concentrates in Examples 2-3 also can be made with the provided methods, using the scaled-up process.

The bench-top process for making the concentrates in Examples 2-3 was performed using the following general steps, except where indicated in the specific examples. Further details for each concentrate are provided in each individual example.

To make each of the liquid nanoemulsion concentrates set forth in Examples 2-3 below, the indicated amount of each ingredient was weighed using a Toledo Scale (Model GD13x/USA), Sartorius Basic Analytical Scale (Model BA110S) or an OHAUS Scale (Model CS2000). Selection of scale(s) depended on the weight of the particular ingredient(s).

To make the water phase, water phase ingredients (indicated by "water" in each table in the "phase" column) were added, in the indicated amounts (g/batch), to a water phase vessel (a Pyrex® beaker), and mixed using a standard mixer (IKA® model No. RE-16 1 S, which is an overhead mixer (laboratory stirrer) compatible with the bench-top process). The water phase of each exemplary concentrate contained water, which was purified city water, purified according to the provided methods by passage through the following purifiers, sequentially: a carbon filter, an ion exchange purifier, a reverse osmosis purifier and an end-point filter, for example, a 100 micron end-point filter, before being added to the water phase tank.

While mixing, the water phase ingredients were heated using a heating apparatus. The heating apparatus was a hot plate (a Thermolyne hot Plate Model # SP46615, Barnstead International, Dubuque, Iowa). Except where indicated, when the water phase included water and an emulsion stabilizer, these ingredients were added sequentially, in the following order: 1) water; 2) emulsion stabilizer.

The water phase ingredients were heated with the hot plate until the temperature reached 60° C. The water phase then was maintained at 60° C. before combining and emulsifying the water and oil phases. A temperature meter (temperature probe (Model # DPP400W, Cooper-Atkins)) was used to evaluate (measure) the temperature of the water phase.

The oil phase ingredients (indicated by "oil" in each table in the "phase" column) were added to an oil phase vessel (a Pyrex® beaker), and mixed using a standard mixer (IKA® model No. RE-16 1S, which is an overhead mixer (laboratory stirrer) compatible with the bench-top process). In general, unless otherwise indicated, when the oil phase included two or more of a surfactant, preservative, solvent, co-surfactant, non-polar compound and emulsion stabilizer, these ingredients were added sequentially, in the following order: 1) surfactant; 2) preservative; 3) solvent; 4) co-surfactant; 5) non-polar compound; and 6) emulsion stabilizer. For example, when the oil phase included surfactant, preservative and non-polar compound, these ingredients were added in the following order (unless otherwise indicated): 1) surfactant, 2) preservative; 3) non-polar compound.

As the oil phase ingredients were mixed, they were heated using a heating apparatus. The heating apparatus was a hot plate (a Thermolyne hot Plate Model # SP46615, Barnstead International, Dubuque, Iowa). The oil phase ingredients were heated until the mixture reached 60° C. The oil phase was mixed at this temperature until all the ingredients had dissolved, and maintained at 60° C. before mixing with the water phase. A temperature meter (temperature probe (Model # DPP400W, Cooper-Atkins)) was used to evaluate (measure) the temperature of the oil phase.

After both phases had reached 60° C. and the oil phase components had dissolved, the phases were combined and emulsified using the following steps. A reversible homogenizer (Arde Barinco, Inc.; Model CJ-4E) was placed in the water phase vessel and turned on at 850-1200 RPM. The oil phase then was transferred to the water phase vessel by pouring the oil phase from the oil phase vessel into the water phase vessel. Mixing with the homogenizer was continued, with adjustment of the baffle plate on the homogenizer to achieve and maintain an emulsion, for example, by moving the baffle plate further into the forming emulsion and/or out of the forming emulsion.

Homogenization of the forming emulsion was continued at between 850 and 1200 rpm, with rapid cooling. Rapid cooling was effected by placing the water phase vessel (beaker), containing the forming emulsion, in a water bath, to cool the forming emulsion until the temperature of the liquid reached between 25° C. and 43° C. (typically taking between about 30 and about 60 minutes).

After emulsifying and rapidly cooling, additional ingredients were added, where indicated in the individual Examples/Tables. For example, any ingredient that was added subsequent to the emulsifying step (instead of to one of the individual phases) is indicated by the word "emulsion" in the "phase" column. The emulsion was mixed while adding any additional ingredients, using the standard mixer (IKA® model No. RE-16 1S). Exemplary of additional ingredients that were added in the following examples are flavors (D-limonene and lemon oil), and pH adjusters (e.g. citric acid). In several examples (where indicated), the pH of the emulsion was measured using a pH and temperature meter (Hanna Instruments, model HI 8314). When needed, the pH was adjusted with the appropriate amount of a pH adjuster (amount indicated in tables), for example, citric acid or phosphoric acid, until the emulsion reached a pH of between 2.6 and 3.2. Each of the concentrates produced in the following Examples had a pH of between about 2.6 and 3.2.

As a final step, the concentrates were filtered using a 100 micron end-product filter, before further evaluation, dilution and/or use.

Example 2

Liquid Nanoemulsion Concentrates with PUFA-Containing Non-Polar Compounds

Examples 2A-2E set forth the details of liquid nanoemulsion concentrates that were made and contained non-polar compounds that include polyunsaturated fatty acids (PUFAs). The concentrates made in this example contained omega-3 fatty acid non-polar active ingredients (e.g. ingredients containing DHA, EPA, ALA and combinations thereof). The same formulations can be used to make concentrates containing other non-polar active ingredients, for example, non-polar active ingredients containing ingredients selected from any one or more of omega-3 fatty acids, omega-6 fatty acids, conjugated fatty acids and other fatty acids. The concentrates in Examples 2A-2E below were made using the general procedure outlined in Example 1, above.

Example 2A

Liquid Nanoemulsion Concentrates with 5% of a DHA-Containing Non-Polar Compound (Fish Oil)

Table 2A, below, sets forth the ingredients used to make a 500 g batch of a DHA-containing liquid nanoemulsion concentrate (2 mL serving size), which was made according to the procedure set forth in Example 1 above, with the following details and modifications:

To make the oil phase using the method described in Example 1, above, the following oil phase ingredients were added sequentially, in the following order, to the oil phase vessel: 1) surfactant; 2) preservative; 3) co-surfactant; 4) non-polar active ingredient; and 5) emulsion stabilizer.

The non-polar active ingredient was fish oil, containing about 70% (74% DHA and about 10% (9.3%) EPA (Omega-3 Fish Oil EE, made by O3C Nutraceuticals, supplied by Jedwards International Inc., Quincy, Mass.). The non-polar active ingredient was added at an amount such that the active ingredient would be 5%, by weight of the final concentrate. The surfactant was polysorbate 80 (purchased from Univar, Inc., Seattle, Wash.). The co-surfactant was a phosphatidylcholine co-surfactant, sold under the trade name S-100, by Lipoid, LLC, Newark, N.J. This phosphatidylcholine was derived from soy extract and contained greater than 95% phosphatidylcholine. The preservative was a natural (GRAS-certified) preservative, benzyl alcohol. The emulsion stabilizer was the SALADIZER® brand emulsion stabilizer, obtained from TIC Gums, Inc., Belcamp, Md.

To make the water phase using the method described in Example 1 above, the following water phase ingredients were added sequentially, in the following order, to the water phase vessel: 1) Water; 2) emulsion stabilizer. The emulsion stabilizer was the SALADIZER® brand emulsion stabilizer, obtained from TIC Gums, Inc., Belcamp, Md.

Flavors (lemon oil, sold by Mission Flavors, Foothill Ranch, Calif.; and 99% GRAS certified D-Limonene, sold by Florida Chemical, Winter Haven, Fla.) were added after emulsifying and rapidly cooling the oil and water phases. After forming the emulsion, an appropriate amount of citric acid (set forth in Table 2A) was added in order to adjust the pH of the emulsion to between 2.6 and 3.4 as described in Example 1 above.

TABLE 2A

Liquid Nanoemulsion Concentrate with 5% of a DHA-containing Non-Polar Compound (Fish Oil)

| Ingredient | mg/2 mL serving | Phase | Percent (by weight) of concentrate | g/batch |
|---|---|---|---|---|
| Fish Oil (10.0% EPA and 70% DHA) (non-polar active ingredient) | 100 | Oil | 5 | 25 |
| Water | 1485.05 | Water | 74.2525 | 371.2625 |
| SALADIZER ® brand emulsion stabilizer (blend of xanthan gum, guar gum and sodium alginate | 6.8 | Water | 0.34 | 1.7 |
| Polysorbate 80 (surfactant) | 360 | Oil | 18 | 90 |
| SALADIZER ® brand emulsion stabilizer (blend of xanthan gum, guar gum and sodium alginate) | 1.27 | Oil | 0.0635 | 0.3175 |
| Benzyl alcohol (preservative) | 10 | Oil | 0.5 | 2.5 |
| D-limonene (flavor) | 10.5 | Emulsion | 0.525 | 2.625 |
| lemon Oil (flavor) | 7.4 | Emulsion | 0.37 | 1.85 |
| Phosphatidylcholine S100 (co-surfactant) | 13.38 | Oil | 0.669 | 3.345 |
| Citric Acid (pH adjuster) | 5.6 | Emulsion | 0.28 | 1.4 |
| Totals | 2000.000 | | 100.0000 | 500 |

Example 2B

Liquid Nanoemulsion Concentrate with 5% of a DHA-Containing Non-Polar Compound (Fish Oil)

Table 2B, below, sets forth the ingredients used to make a 250 g batch of a DHA-containing liquid nanoemulsion concentrate (2 mL serving size), which was made according to the procedure set forth in Example 1 above, with the following details and modifications:

To make the oil phase using the method described in Example 1, above, the following oil phase ingredients were added sequentially, in the following order, to the oil phase vessel: 1) surfactant; 2) preservative; 3) non-polar active ingredient; and 4) emulsion stabilizer.

The non-polar active ingredient was fish oil containing about 70% (74%) DHA and about 10% (9.3%) EPA (Omega-3 Fish Oil EE, made by O3C Nutraceuticals, supplied by Jedwards International Inc., Quincy, Mass.). The non-polar active ingredient was added at an amount such that the active ingredient would be 5%, by weight of the final concentrate. The surfactant was polysorbate 80 (purchased from Univar, Inc., Seattle, Wash.). The preservative was a natural (GRAS-certified) preservative, benzyl alcohol. The emulsion stabilizer was the SALADIZER® brand emulsion stabilizer, obtained from TIC Gums, Inc., Belcamp, Md.

To make the water phase using the method described in Example 1, above, the following water phase ingredients were added sequentially, in the following order, to the water phase vessel: 1) water; 2) emulsion stabilizer. The emulsion stabilizer was the SALADIZER® brand emulsion stabilizer, obtained from TIC Gums, Inc., Belcamp, Md.

After forming the emulsion, an appropriate amount of citric acid (set forth in Table 2B) was added in order to adjust the pH of the emulsion to between 2.6 and 3.4 as described in Example 1, above.

added at an amount such that the ingredient would be 5%, by weight, of the final concentrate.

The surfactant was polysorbate 80 (purchased from Univar, Inc., Seattle, Wash.). The co-surfactant was a phosphatidylcholine co-surfactant, sold under the trade name S-100, by Lipoid, LLC, Newark, N.J. This phosphatidylcholine co-surfactant was derived from soy extract and contained

TABLE 2B

Liquid Nanoemulsion Concentrate with 5% of a DHA-containing Non-Polar Compound (Fish Oil)

| Ingredient | mg/2 mL serving | Phase | Percent (by weight) of concentrate | g/batch |
| --- | --- | --- | --- | --- |
| Fish Oil (10% EPA; 70% DHA) | 100 | Oil | 5 | 12.5 |
| Water | 1375.73 | Water | 68.7865 | 171.96625 |
| SALADIZER ® brand emulsion stabilizer (blend of xanthan gum, guar gum and sodium alginate) | 3.4 | Water | 0.17 | 0.425 |
| Polysorbate 80 (surfactant) | 504 | Oil | 25.2 | 63 |
| SALADIZER ® brand emulsion stabilizer (blend of xanthan gum, guar gum and sodium alginate) | 1.27 | Oil | 0.0635 | 0.15875 |
| Benzyl alcohol (preservative) | 10 | Oil | 0.5 | 1.25 |
| Citric Acid (pH adjuster) | 5.6 | Emulsion | 0.28 | 0.7 |
| Totals | 2000.000 | | 100.0000 | 250 |

Example 2C

Liquid Nanoemulsion Concentrate with 5% of an ALA-Containing Non-Polar Compound (Flaxseed Oil)

Table 2C, below, sets forth the ingredients used to make a 500 g batch of alpha-linolenic acid (ALA)-containing liquid nanoemulsion concentrate (2 mL serving size), which was made according to the procedure set forth in Example 1 above, with the following details and modifications:

To make the oil phase using the method described in Example 1, above, the following oil phase ingredients were added sequentially, in the following order, to the oil phase vessel: 1) surfactant; 2) preservative; 3) solvent; 4) co-surfactant; 5) non-polar active ingredient; and 6) emulsion stabilizer.

The non-polar active ingredient, added to the oil phase, was a flaxseed oil compound, obtained from Sanmark LLC, Greensboro, N.C. (Sanmark Limited, Dalian, Liaoning Province, China), which contains not less than (NLT) 50% C18:3 alpha-linolenic acid. The non-polar active ingredient was greater than 95% phosphatidylcholine. The solvent was a Vitamin E oil, sold by ADM Natural Health and Nutrition, Decatur, Ill., under the name Novatol™ 5-67 Vitamin E (D-alpha-Tocopherol; ADM product code 410217). This oil contained at least 67.2% Tocopherol and approximately 32.8% soybean oil. The preservative was a natural (GRAS-certified) preservative, benzyl alcohol. The emulsion stabilizer was the SALADIZER® brand emulsion stabilizer, obtained from TIC Gums, Inc., Belcamp, Md.

To make the water phase using the method described in Example 1, above, the following water phase ingredients were added sequentially, in the following order, to the water phase vessel: 1) water; 2) emulsion stabilizer. The emulsion stabilizer was the SALADIZER® brand emulsion stabilizer, obtained from TIC Gums, Inc., Belcamp, Md.

After forming the emulsion, an appropriate amount of citric acid (set forth in Table 2C) was added in order to adjust the pH of the emulsion to between 2.6 and 3.4 as described in Example 1, above.

TABLE 2C

Liquid Nanoemulsion Concentrate with 5% of an ALA-containing Non-Polar Compound (Flaxseed Oil)

| Ingredient | mg/2 mL serving | Phase | Percent (by weight) of concentrate | g/batch |
| --- | --- | --- | --- | --- |
| Vitamin E oil (5-67) (solvent) | 75.00 | Oil | 3.750 | 18.75 |
| SALADIZER ® brand emulsion stabilizer (blend of xanthan gum, guar gum and sodium alginate) | 1.270 | Oil | 0.06 | 0.3 |
| Water | 1435 | Water | 71.74 | 358.7 |
| SALADIZER ® brand emulsion stabilizer (blend of xanthan gum, guar gum and sodium alginate) | 6.800 | Water | 0.34 | 1.7 |
| Polysorbate 80 (surfactant) | 355.0 | Oil | 17.75 | 88.75 |

TABLE 2C-continued

Liquid Nanoemulsion Concentrate with 5% of an ALA-containing Non-Polar Compound (Flaxseed Oil)

| Ingredient | mg/2 mL serving | Phase | Percent (by weight) of concentrate | g/batch |
|---|---|---|---|---|
| Phosphatidylcholine S-100 (co-surfactant) | 13.38 | Oil | 0.6690 | 3.345 |
| Benzyl Alcohol (preservative) | 10.00 | Oil | 0.5000 | 2.5000 |
| Flax Seed Oil 50% Omega 3 | 100.0 | Oil | 5.0000 | 25.000 |
| Citric Acid (pH adjuster) | 3.800 | Emulsion | 0.1900 | 0.9500 |
| Totals | 2000.00 | | 100.000 | 500 |

Example 2D

Liquid Nanoemulsion Concentrate with 5% of an ALA-Containing Non-Polar Compound (Flaxseed Oil)

Table 2D, below, sets forth the ingredients used to make a 250 g batch of alpha-linolenic acid (ALA)-containing liquid nanoemulsion concentrate (2 mL serving size), which was made according to the procedure set forth in Example 1 above, with the following details and modifications:

To make the oil phase using the method described in Example 1, above, the following oil phase ingredients were added sequentially, in the following order, to the oil phase vessel: 1) surfactant; 2) preservative; 3) non-polar active ingredient; and 4) emulsion stabilizer.

The non-polar active ingredient was a flaxseed oil compound, obtained from Sanmark LLC, Greensboro, N.C. (Sanmark Limited, Dalian, Liaoning Province, China), which contained not less than (NLT) 50% C18:3 alpha-linolenic acid (ALA). The non-polar active ingredient was added at an amount such that the ingredient would be 5%, by weight, of the final concentrate. The surfactant, polysorbate 80 surfactant (purchased from Univar, Inc., Seattle, Wash.) also was added to the oil phase. The preservative was a natural (GRAS-certified) preservative, benzyl alcohol. The emulsion stabilizer was the SALADIZER® brand emulsion stabilizer, obtained from TIC Gums, Inc., Belcamp, Md.

To make the water phase using the method described in Example 1, above, the following water phase ingredients were added sequentially, in the following order, to the water phase vessel: 1) water; 2) emulsion stabilizer. The emulsion stabilizer was the SALADIZER® brand emulsion stabilizer, obtained from TIC Gums, Inc., Belcamp, Md.

After forming the emulsion, an appropriate amount of citric acid (set forth in Table 2D) was added in order to adjust the pH of the emulsion to between 2.6 and 3.4 as described in Example 1, above.

TABLE 2D

Liquid Nanoemulsion Concentrate with 5% of an ALA-containing Non-Polar Compound (Flaxseed Oil)

| Ingredient | mg/2 mL serving | Phase | Percent (by weight) of concentrate | g/batch |
|---|---|---|---|---|
| Flaxseed Oil 50% Omega-3 | 100 | Oil | 5 | 12.5 |
| Water | 1375.73 | Water | 68.7865 | 171.96625 |
| SALADIZER ® brand emulsion stabilizer (blend of xanthan gum, guar gum and sodium alginate) | 3.4 | Water | 0.17 | 0.425 |
| Polysorbate 80 (surfactant) | 504 | Oil | 25.2 | 63 |
| SALADIZER ® brand emulsion stabilizer (blend of xanthan gum, guar gum and sodium alginate) | 1.27 | Oil | 0.0635 | 0.15875 |
| Benzyl Alcohol (preservative) | 10 | Oil | 0.5 | 1.25 |
| Citric Acid (pH adjuster) | 5.6 | Emulsion | 0.28 | 0.7 |
| Totals | 2000.000 | | 100.0000 | 250 |

Example 2E

Liquid Nanoemulsion Concentrate with 10% of an ALA-Containing Non-Polar Compound (Flaxseed Oil)

Table 2E, below, sets forth the ingredients used to make a 250 g batch of alpha-linolenic acid (ALA)-containing liquid nanoemulsion concentrate (2 mL serving size), which was made according to the procedure set forth in Example 1 above, with the following details and modifications:

To make the oil phase using the method described in Example 1, above, the following oil phase ingredients were added sequentially, in the following order, to the oil phase vessel: 1) surfactant; 2) preservative; 3) non-polar active ingredient; and 4) emulsion stabilizer.

The non-polar active ingredient was a flaxseed oil compound, obtained from Sanmark LLC, Greensboro, N.C. (Sanmark Limited, Dalian, Liaoning Province, China), which contained not less than (NLT) 50% C18:3 alpha-linolenic acid (ALA). The non-polar active ingredient was added at an amount such that the ingredient would be 10%, by weight, of the final concentrate. The surfactant was polysorbate 80 surfactant (purchased from Univar, Inc., Seattle, Wash.). The preservative was a natural (GRAS-certified) preservative, benzyl alcohol. The emulsion stabilizer was the SALADIZER® brand emulsion stabilizer, obtained from TIC Gums, Inc., Belcamp, Md.

To make the water phase using the method described in Example 1, above, the following water phase ingredients were added sequentially, in the following order, to the water phase vessel: 1) water; 2) emulsion stabilizer. The emulsion stabilizer was the SALADIZER® brand emulsion stabilizer, obtained from TIC Gums, Inc., Belcamp, Md.

After forming the emulsion, an appropriate amount of citric acid (set forth in Table 2E) was added in order to adjust the pH of the emulsion to between 2.6 and 3.4 as described in Example 1, above.

added sequentially, in the following order, to the oil phase vessel: 1) surfactant; 2) preservative; 3) solvent; 4) co-surfactant; 5) non-polar active ingredient; and 6) emulsion stabilizer.

The non-polar active ingredient was a Coenzyme Q 10 (CoQ10) compound, sold under the name Kaneka Q10™ (USP Ubidecarenone) by Kaneka Nutrients, L.P., Pasadena, Tex., which contains greater than 98% ubidecarenone (ubiquinone). The non-polar active ingredient was added at an amount such that the ingredient would be 5%, by weight, of the final concentrate. The surfactant was a polysorbate 80 surfactant (purchased from Univar, Inc., Seattle, Wash.). The co-surfactant was a phosphatidylcholine co-surfactant, sold under the trade name S-100, by Lipoid, LLC, Newark, N.J. This phosphatidylcholine co-surfactant was derived from soy extract and contained greater than 95% phosphatidylcholine. The solvent was a Vitamin E oil, sold by ADM Natural Health and Nutrition, Decatur, Ill., under the name Novatol™ 5-67 Vitamin E (D-alpha-Tocopherol; ADM product code 410217). This oil contained at least 67.2% Tocopherol and approximately 32.8% soybean oil. The preservative was a natural (GRAS-certified) preservative, benzyl alcohol. The emulsion stabilizer was SALADIZER® brand emulsion stabilizer, obtained from TIC Gums, Inc., Belcamp, Md.

TABLE 2E

Liquid Nanoemulsion Concentrate with 10% of an ALA-containing Non-Polar Compound (Flaxseed Oil)

| Ingredient | mg/2 mL serving | Phase | Percent (by weight) of concentrate | g/batch |
| --- | --- | --- | --- | --- |
| Flaxseed Oil 50% Omega-3 | 200 | Oil | 10 | 25 |
| Water | 1375.73 | Water | 68.7865 | 171.96625 |
| SALADIZER ® brand emulsion stabilizer (blend of xanthan gum, guar gum and sodium alginate) | 3.4 | Water | 0.17 | 0.425 |
| Polysorbate 80 (surfactant) | 404 | Oil | 20.2 | 50.5 |
| SALADIZER ® brand emulsion stabilizer (blend of xanthan gum, guar gum and sodium alginate) | 1.27 | Oil | 0.0635 | 0.15875 |
| Benzyl Alcohol (preservative) | 10 | Oil | 0.5 | 1.25 |
| Citric Acid (pH adjuster) | 5.6 | Emulsion | 0.28 | 0.7 |
| Totals | 2000.000 | | 100.0000 | 250 |

Example 3

Liquid Nanoemulsion Concentrates with Coenzyme Q10 (CoQ10)-Containing Non-Polar Compounds Table 3A below, sets forth the ingredients used to make a 650 g batch of CoQ10-containing liquid nanoemulsion concentrate (2 mL serving size), which was made according to the procedure set forth in Example 1 above, with the following details and modifications:

To make the oil phase using the method described in Example 1, above, the following oil phase ingredients were To make the water phase using the method described in Example 1, above, the following water phase ingredients were added sequentially, in the following order, to the water phase vessel: 1) water, 2) emulsion stabilizer. The emulsion stabilizer was SALADIZER® brand emulsion stabilizer, obtained from TIC Gums, Inc., Belcamp, Md.

After forming the emulsion, an appropriate amount of citric acid (set forth in Table 3A) was added in order to adjust the pH of the emulsion to between 2.6 and 3.4 as described in Example 1, above.

TABLE 3A

Liquid Nanoemulsion Concentrate with 5% Coenzyme Q-containing Non-Polar Compound (CoQ10)

| Ingredient | mg/2 mL serving | Phase | Percent (by weight) of concentrate | g/batch |
|---|---|---|---|---|
| Vitamin E oil (5-67) (solvent) | 75.00 | Oil | 3.750 | 24.375 |
| SALADIZER ® brand emulsion stabilizer (blend of xanthan gum, guar gum and sodium alginate) | 1.270 | Oil | 0.06 | 0.4 |
| Water | 1435 | Water | 71.74 | 466.3 |
| SALADIZER ® brand emulsion stabilizer (blend of xanthan gum, guar gum and sodium alginate) | 6.800 | Water | 0.34 | 2.2 |
| Polysorbate 80 (surfactant) | 355.0 | Oil | 17.75 | 115.38 |
| Phosphatidylcholine S-100 (co-surfactant) | 13.38 | Oil | 0.6690 | 4.349 |
| Benzyl Alcohol (preservative) | 10.00 | Oil | 0.5000 | 3.2500 |
| CoQ10 | 100.0 | Oil | 5.0000 | 32.500 |
| Citric Acid (pH adjuster) | 3.800 | Emulsion | 0.1900 | 1.2350 |
| Totals | 2000.00 | | 100.000 | 650 |

Example 4

Liquid Nanoemulsion Concentrates with PUFA-Containing Non-Polar Compounds

Examples 4A-4D (and subsections thereof) set forth the details of formulations for making liquid nanoemulsion concentrates containing non-polar compounds that include polyunsaturated fatty acids (PUFAs) (e.g. non-polar active ingredients containing omega-3 fatty acids, omega-6 fatty acids, conjugated fatty acids and other fatty acids). These concentrates can be made using the general procedure outlined in Example 1, above.

Example 4A

Liquid Nanoemulsion Concentrates with Omega-3 Containing Non-Polar Compounds Examples 4A(i)-4A(vii) set forth the details of formulations for making liquid nanoemulsion concentrates containing non-polar compounds that contain omega-3 fatty acids (e.g. DHA, EPA, ALA). These concentrates can be made using the general procedure outlined in Example 1, above.

Example 4A(i)

Liquid Nanoemulsion Concentrate with 5% of a DHA-Containing Non-Polar Compound (Algae Oil) and 18% Polysorbate 80

Table 4A(i), below, sets forth ingredients that are used to make a 200 g batch of an exemplary DHA-containing liquid nanoemulsion concentrate (2 mL serving size), which is made according to the procedure set forth in Example 1 above, with the following details and modifications:

To make the oil phase using the method described in Example 1, above, the following oil phase ingredients are added sequentially, in the following order, to the oil phase vessel: 1) surfactant, 2) preservative; 3) non-polar active ingredient; and 4) emulsion stabilizer.

The non-polar active ingredient is algae oil, containing 35% DHA. The non-polar active ingredient is added at an amount such that the ingredient is 5%, by weight, of the final concentrate. The surfactant is polysorbate 80 (which is purchased from Univar, Inc., Seattle, Wash.). The preservative is a natural (GRAS-certified) preservative, benzyl alcohol. The emulsion stabilizer is the SALADIZER® brand emulsion stabilizer, which is purchased from TIC Gums, Inc., Belcamp, Md.

To make the water phase using the method described in Example 1, the following water phase ingredients are added, in the following order, to the water phase vessel: 1) water; 2) emulsion stabilizer. The emulsion stabilizer is the SALADIZER® brand emulsion stabilizer, which is purchased from TIC Gums, Inc., Belcamp, Md.

After forming the emulsion, an appropriate amount of citric acid (set forth in Table 4A(i)) is added in order to adjust the pH of the emulsion to between 2.6 and 3.4 as described in Example 1 above.

TABLE 4A(i)

Liquid Nanoemulsion Concentrate with 5% of a DHA-containing non-polar compound (Algae Oil) and 18% polysorbate 80

| Ingredient | mg/2 mL serving | Phase | Percent (by weight) of concentrate | g/batch |
|---|---|---|---|---|
| Algae Oil (35% DHA) | 100 | Oil | 5 | 10 |
| Water | 1516.33 | Water | 75.8165 | 151.633 |
| SALADIZER ® brand emulsion stabilizer (blend of xanthan gum, guar gum and sodium alginate) | 6.8 | Water | 0.34 | 0.68 |
| Polysorbate 80 (surfactant) | 360 | Oil | 18 | 36 |

TABLE 4A(i)-continued

Liquid Nanoemulsion Concentrate with 5% of a DHA-containing non-polar compound (Algae Oil) and 18% polysorbate 80

| Ingredient | mg/2 mL serving | Phase | Percent (by weight) of concentrate | g/batch |
|---|---|---|---|---|
| SALADIZER ® brand emulsion stabilizer (blend of xanthan gum, guar gum and sodium alginate) | 1.27 | Oil | 0.0635 | 0.127 |
| Benzyl Alcohol (preservative) | 10 | Oil | 0.5 | 1 |
| Citric Acid (pH adjuster) | 5.6 | Emulsion | 0.28 | 0.56 |
| Totals | 2000.000 | | 100.0000 | 200 |

Example 4A(ii)

Liquid Nanoemulsion Concentrate with 5% of a DHA-Containing Non-Polar Compound (Algae Oil) and 25.2% Polysorbate 80

Table 4A(ii), below, sets forth the ingredients for making a 150 g batch of an exemplary DHA-containing liquid nanoemulsion concentrate (2 mL serving size), which can be made according to the procedure set forth in Example 1 above, with the following details and modifications:

To make the oil phase using the method described in Example 1, above, the following oil phase ingredients are added sequentially, in the following order, to the oil phase vessel: 1) surfactant, 2) preservative; 3) non-polar active ingredient; and 4) emulsion stabilizer. The non-polar active ingredient is algae oil, containing 35% DHA. The non-polar active ingredient is added at an amount such that the active ingredient is 5%, by weight, of the final concentrate. The surfactant is polysorbate 80 (which is purchased from Univar, Inc., Seattle, Wash.). The preservative is a natural (GRAS-certified) preservative, benzyl alcohol. The emulsion stabilizer is the SALADIZER® brand emulsion stabilizer, which is purchased from TIC Gums, Inc., Belcamp, Md.

To make the water phase using the methods described in Example 1, above, the following water phase ingredients are added sequentially, in the following order, to the water phase vessel: 1) water; 2) emulsion stabilizer. The emulsion stabilizer is the SALADIZER® brand emulsion stabilizer, which is purchased from TIC Gums, Inc., Belcamp, Md.

After forming the emulsion, an appropriate amount of citric acid (set forth in Table 4A(ii)) is added in order to adjust the pH of the emulsion to between 2.6 and 3.4 as described in Example 1 above.

TABLE 4A(ii)

Liquid Nanoemulsion Concentrate with 5% of a DHA-containing non-polar compound (Algae Oil) with 25.2% polysorbate 80

| Ingredient | mg/2 mL serving | Phase | Percent (by weight) of concentrate | g/batch |
|---|---|---|---|---|
| Algae Oil (35% DHA) | 100 | Oil | 5 | 7.5 |
| Water | 1375.73 | Water | 68.7865 | 103.17975 |
| SALADIZER ® brand emulsion stabilizer (blend of xanthan gum, guar gum and sodium alginate) | 3.4 | Water | 0.17 | 0.255 |
| Polysorbate 80 (surfactant) | 504 | Oil | 25.2 | 37.8 |
| SALADIZER ® brand emulsion stabilizer (blend of xanthan gum, guar gum and sodium alginate) | 1.27 | Oil | 0.0635 | 0.09525 |
| Benzyl Alcohol (preservative) | 10 | Oil | 0.5 | 0.75 |
| Citric Acid (pH adjuster) | 5.6 | Emulsion | 0.28 | 0.42 |
| Totals | 2000.000 | | 100.0000 | 150 |

Example 4A(iii)

Liquid Nanoemulsion Concentrate with 10% of a DHA-Containing Non-Polar Compound (Algae Oil)

Table 4A(iii), below, sets forth the ingredients for making a 500 g batch of an exemplary DHA-containing liquid nanoemulsion concentrate (2 mL serving size), which is made according to the procedure set forth in Example 1 above, with the following details and modifications:

To make the oil phase using the method described in Example 1, above, the following oil phase ingredients are added sequentially, in the following order, to the oil phase vessel: 1) surfactant; 2) preservative; 3) non-polar active ingredient; and 4) emulsion stabilizer.

The non-polar active ingredient is algae oil, containing 35% DHA. The non-polar active ingredient is added at an amount such that the ingredient is 10%, by weight, of the final concentrate. The surfactant is polysorbate 80 (which is purchased from Univar, Inc., Seattle, Wash.). The preservative is natural (GRAS-certified) preservative, benzyl alcohol. The emulsion stabilizer is the SALADIZER® brand emulsion stabilizer, which is purchased from TIC Gums, Inc., Belcamp, Md.

To make the water phase using the method described in Example 1, above, the following water phase ingredients are added sequentially, in the following order, to the water phase vessel: 1) water; 2) emulsion stabilizer. The emulsion stabilizer is the SALADIZER® brand emulsion stabilizer, which is purchased from TIC Gums, Inc., Belcamp, Md.

After forming the emulsion, an appropriate amount of citric acid (set forth in Table 4A(iii)) is added in order to adjust the pH of the emulsion to between 2.6 and 3.4 as described in Example 1, above.

vessel: 1) surfactant; 2) preservative; 3) non-polar active ingredient; and 4) emulsion stabilizer.

The non-polar active ingredient is Denomega™ 100, fish oil, which contains about 13% DHA and about 13% EPA. The non-polar active ingredient is added at an amount such that the active ingredient is 5%, by weight of the final concentrate. The surfactant is polysorbate 80 (which is purchased from Univar, Inc., Seattle, Wash.). The preservative is a natural (GRAS-certified) preservative, benzyl alcohol. The emulsion stabilizer is the SALADIZER® brand emulsion stabilizer, which is purchased from TIC Gums, Inc., Belcamp, Md. To make the water phase using the method described in Example 1, above, the following water phase ingredients are added sequentially, in the following order, to the water phase vessel: I) water; 2) emulsion stabilizer. The emulsion stabilizer is the TABLE 4A(iii)

Liquid Nanoemulsion Concentrate With 10% of a DHA-Containing Non-Polar Compound (Algae Oil)

| Ingredient | mg/2 mL serving | Phase | Percent (by weight) of concentrate | g/batch |
|---|---|---|---|---|
| Algae Oil (35% DHA) | 200 | Oil | 10 | 50 |
| Water | 1278.76 | Water | 63.938 | 319.69 |
| SALADIZER ® brand emulsion stabilizer (blend of xanthan gum, guar gum and sodium alginate) | 1.2 | Water | 0.06 | 0.3 |
| Polysorbate 80 (surfactant) | 504 | Oil | 25.2 | 126 |
| SALADIZER ® brand emulsion stabilizer (blend of xanthan gum, guar gum and sodium alginate) | 0.44 | Oil | 0.022 | 0.11 |
| Benzyl Alcohol (preservative) | 10 | Oil | 0.5 | 2.5 |
| Citric Acid (pH adjuster) | 5.6 | Emulsion | 0.28 | 1.4 |
| Totals | 2000.000 | | 100.0000 | 500 |

Example 4A(iv)

Liquid Nanoemulsion Concentrate with 5% of a DHA-Containing Non-Polar Compound (Fish Oil)

Table 4A(iv), below, sets forth the ingredients for making a 250 g batch of an exemplary DHA-containing liquid nanoemulsion concentrate (2 mL serving size), which is made according to the procedure set forth in Example 1 above, with the following details and modifications:

To make the oil phase using the method described in Example 1, above, the following oil phase ingredients are added sequentially, in the following order, to the oil phase SALADIZER® brand emulsion stabilizer, which is purchased from TIC Gums, Inc., Belcamp, Md.

To make the water phase using the method described in Example 1, above, the following water phase ingredients are added sequentially, in the following order, to the water phase vessel: 1) water; 2) emulsion stabilizer. The emulsion stabilizer is the SALADIZER® brand emulsion stabilizer, which is purchased from TIC Gums, Inc., Belcamp, Md.

After forming the emulsion, an appropriate amount of citric acid (set forth in Table 4A(iv)) is added in order to adjust the pH of the emulsion to between 2.6 and 3.4 as described in Example 1, above.

TABLE 4A(iv)

Liquid Nanoemulsion Concentrate with 5% of a DHA-containing Non-Polar Compound (Fish Oil)

| Ingredient | mg/2 mL serving | Phase | Percent (by weight) of concentrate | g/batch |
|---|---|---|---|---|
| Fish Oil (about 13% EPA; 13% DHA) | 100 | Oil | 5 | 12.5 |
| Water | 1375.73 | Water | 68.7865 | 171.96625 |
| SALADIZER ® brand emulsion stabilizer (blend of xanthan gum, guar gum and sodium alginate) | 3.4 | Water | 0.17 | 0.425 |
| Polysorbate 80 (surfactant) | 504 | Oil | 25.2 | 63 |
| SALADIZER ® brand emulsion stabilizer (blend of xanthan gum, guar gum and sodium alginate) | 1.27 | Oil | 0.0635 | 0.15875 |

TABLE 4A(iv)-continued

Liquid Nanoemulsion Concentrate with 5% of a DHA-containing Non-Polar Compound (Fish Oil)

| Ingredient | mg/2 mL serving | Phase | Percent (by weight) of concentrate | g/batch |
|---|---|---|---|---|
| Benzyl alcohol (preservative) | 10 | Oil | 0.5 | 1.25 |
| Citric Acid (pH adjuster) | 5.6 | Emulsion | 0.28 | 0.7 |
| Totals | 2000.000 | | 100.0000 | 250 |

Example 4A(v)

Liquid Nanoemulsion Concentrate with 10% of a DHA-Containing Non-Polar Compound (Fish Oil)

Table 4A(v), below, sets forth the ingredients for making a 250 g batch of an exemplary DHA-containing liquid nanoemulsion concentrate (2 mL serving size), which is made according to the procedure set forth in Example 1 above, with the following details and modifications:

To make the oil phase using the method described in Example 1, above, the following oil phase ingredients are added sequentially, in the following order, to the oil phase vessel: 1) surfactant; 2) preservative; 3) non-polar active ingredient; and 4) emulsion stabilizer.

The non-polar active ingredient is Denomega® 100, fish oil, which contains about 13% DHA and about 13% EPA. The non-polar active ingredient is added at an amount such that the active ingredient is 10%, by weight of the final concentrate. The surfactant is polysorbate 80 (which is purchased from Univar, Inc., Seattle, Wash.). The preservative is a natural (GRAS-certified) preservative, benzyl alcohol. The emulsion stabilizer is the SALADIZER® brand emulsion stabilizer, which is purchased from TIC Gums, Inc., Belcamp, Md.

To make the water phase using the method described in Example 1, above, the following water phase ingredients are added sequentially, in the following order, to the water phase vessel: 1) water; 2) emulsion stabilizer. The emulsion stabilizer is the SALADIZER® brand emulsion stabilizer, obtained from TIC Gums, Inc., Belcamp, Md.

After forming the emulsion, an appropriate amount of citric acid (set forth in Table 4A(v)) is added in order to adjust the pH of the emulsion to between 2.6 and 3.4 as described in Example 1, above.

Example 4A(vi)

Liquid Nanoemulsion Concentrate with 10% of a DHA-Containing Non-Polar Compound (Fish Oil)

Table 4A(vi), below, sets forth the ingredients for making a 250 g batch of an exemplary DHA-containing liquid nanoemulsion concentrate (2 mL serving size), which is made according to the procedure set forth in Example 1 above, with the following details and modifications:

To make the oil phase using the method described in Example 1, above, the following oil phase ingredients are added sequentially, in the following order, to the oil phase vessel: 1) surfactant; 2) preservative; 3) non-polar active ingredient; and 4) emulsion stabilizer.

The non-polar active ingredient is fish oil, containing about 70% (74%) DHA and about 10% (9.3%) EPA (Omega-3 Fish Oil EE, made by O3C Nutraceuticals, supplied by Jedwards International Inc., Quincy, Mass.). The non-polar active ingredient is added at an amount such that the active ingredient is 10%, by weight of the final concentrate. The surfactant is polysorbate 80 (which is purchased from Univar, Inc., Seattle, Wash.). The preservative is a natural (GRAS-certified) preservative, benzyl alcohol. The emulsion stabilizer is the SALADIZER® brand emulsion stabilizer, which is obtained from TIC Gums, Inc., Belcamp, Md.

To make the water phase using the method described in Example 1, above, the following water phase ingredients are added sequentially, in the following order, to the water phase vessel: 1) water; 2) emulsion stabilizer. The emulsion stabilizer is the SALADIZER® brand emulsion stabilizer, obtained from TIC Gums, Inc., Belcamp, Md.

TABLE 4A(v)

Liquid Nanoemulsion Concentrate with 10% of a DHA-containing Non-Polar Compound (Fish Oil)

| Ingredient | mg/2 mL serving | Phase | Percent (by weight) of concentrate | g/batch |
|---|---|---|---|---|
| Fish Oil (about 13% EPA; 13% DHA) | 200 | Oil | 10 | 25 |
| Water | 1375.73 | Water | 68.7865 | 171.96625 |
| SALADIZER ® brand emulsion stabilizer (blend of xanthan gum, guar gum and sodium alginate) | 3.4 | Water | 0.17 | 0.425 |
| Polysorbate 80 (surfactant) | 404 | Oil | 20.2 | 50.5 |
| SALADIZER ® brand emulsion stabilizer (blend of xanthan gum, guar gum and sodium alginate) | 1.27 | Oil | 0.0635 | 0.15875 |
| Benzyl alcohol (preservative) | 10 | Oil | 0.5 | 1.25 |
| Citric Acid (pH adjuster) | 5.6 | Emulsion | 0.28 | 0.7 |
| Totals | 2000.000 | | 100.0000 | 250 |

After forming the emulsion, an appropriate amount of citric acid (set forth in Table 4A(vi)) is added in order to adjust the pH of the emulsion to between 2.6 and 3.4 as described in Example 1, above.

TABLE 4A(vi)

Liquid Nanoemulsion Concentrate with 10% of a DHA-containing non-polar compound (Fish Oil)

| Ingredient | mg/2 mL serving | Phase | Percent (by weight) of concentrate | g/batch |
|---|---|---|---|---|
| Fish Oil (10% EPA; 70% DHA) | 200 | Oil | 10 | 25 |
| Water | 1375.73 | Water | 68.7865 | 171.96625 |
| SALADIZER ® brand emulsion stabilizer (blend of xanthan gum, guar gum and sodium alginate) | 3.4 | Water | 0.17 | 0.425 |
| Polysorbate 80 (surfactant) | 404 | Oil | 20.2 | 50.5 |
| SALADIZER ® brand emulsion stabilizer (blend of xanthan gum, guar gum and sodium alginate) | 1.27 | Oil | 0.0635 | 0.15875 |
| Benzyl alcohol (preservative) | 10 | Oil | 0.5 | 1.25 |
| Citric Acid (pH adjuster) | 5.6 | Emulsion | 0.28 | 0.7 |
| Totals | 2000.000 | | 100.0000 | 250 |

Example 4A(vii)

Liquid Nanoemulsion Concentrate with 5% of a DHA-Containing Non-Polar Compound (Fish Oil)

Table 4A(vii), below, sets forth the ingredients for making a 250 g batch of an exemplary DHA-containing liquid nanoemulsion concentrate (2 mL serving size), which is made according to the procedure set forth in Example 1 above, with the following details and modifications:

To make the oil phase using the method described in Example 1, above, the following oil phase ingredients are added sequentially, in the following order, to the oil phase vessel: 1) surfactant; 2) preservative; 3) non-polar active ingredient; and 4) emulsion stabilizer.

The non-polar active ingredient is a fish oil, which contains about 20% DHA and about 40% EPA (made by O3C Nutraceuticals, supplied by Jedwards International Inc., Quincy, Mass.). The non-polar active ingredient is added at an amount such that the active ingredient is 5%, by weight of the final concentrate. The surfactant is polysorbate 80 surfactant (which is purchased from Univar, Inc., Seattle, Wash.). The preservative is a natural (GRAS-certified) preservative, benzyl alcohol. The emulsion stabilizer is the SALADIZER® brand emulsion stabilizer, obtained from TIC Gums, Inc., Belcamp, Md.

To make the water phase using the method described in Example 1, above, the following water phase ingredients are added sequentially, in the following order, to the water phase vessel: 1) water; 2) emulsion stabilizer. The emulsion stabilizer is the SALADIZER® brand emulsion stabilizer, which is obtained from TIC Gums, Inc., Belcamp, Md.

After forming the emulsion, an appropriate amount of citric acid (set forth in Table 4A(vii)) is added in order to adjust the pH of the emulsion to between 2.6 and 3.4 as described in Example 1, above.

TABLE 4A(vii)

Liquid Nanoemulsion Concentrate with 5% of a DHA-containing Non-Polar Compound (Fish Oil)

| Ingredient | mg/2 mL serving | Phase | Percent (by weight) of concentrate | g/batch |
|---|---|---|---|---|
| Fish Oil (40% EPA; 20% DHA) | 100 | Oil | 5 | 12.5 |
| Water | 1375.73 | Water | 68.7865 | 171.96625 |
| SALADIZER ® brand emulsion stabilizer (blend of xanthan gum, guar gum and sodium alginate) | 3.4 | Water | 0.17 | 0.425 |
| Polysorbate 80 (surfactant) | 504 | Oil | 25.2 | 63 |
| SALADIZER ® brand emulsion stabilizer (blend of xanthan gum, guar gum and sodium alginate) | 1.27 | Oil | 0.0635 | 0.15875 |
| Benzyl alcohol (preservative) | 10 | Oil | 0.5 | 1.25 |
| Citric Acid (pH adjuster) | 5.6 | Emulsion | 0.28 | 0.7 |
| Totals | 2000.000 | | 100.0000 | 250 |

Example 4B

Liquid Nanoemulsion Concentrates with Omega-6 Containing Non-Polar Compounds Examples 4B(i)-4B(iii) set forth the details of formulations for making liquid nanoemulsion concentrates containing non-polar compounds that contain omega-6 fatty acids (e.g. GLA). These concentrates can be made using the general procedure outlined in Example 1, above.

Example 4B(i)

Liquid Nanoemulsion Concentrate with 5% GLA-Containing Non-Polar Compound (Borage Oil)

Table 4B(i), below, sets forth the ingredients used for making a 500 g batch of an exemplary GLA (Gamma Linoleic Acid)-containing liquid nanoemulsion concentrate (2 mL serving size), which is made according to the procedure set forth in Example 1 above, with the following details and modifications:

To make the oil phase using the method described in Example 1, above, the following oil phase ingredients are added sequentially, in the following order, to the oil phase vessel: 1) surfactant; 2) preservative; 3) solvent; 4) co-surfactant; 5) non-polar active ingredient; and 6) emulsion stabilizer.

The non-polar active ingredient is a borage oil compound, which is obtained from Sanmark LLC, Greensboro, N.C. (Sanmark Limited, Dalian, Liaoning Province, China), which is derived by pressing and isolating oil from the seeds of *Borago officinalis* L. This oil contains not less than (NLT) 22% C18:3 gamma-linolenic acid (GLA). The non-polar active ingredient is added at an amount such that the ingredient is 5%, by weight, of the final concentrate. The surfactant is a polysorbate 80 surfactant (which is purchased from Univar, Inc., Seattle, Wash.). The co-surfactant is a phosphatidylcholine co-surfactant, sold under the trade name S-100, by Lipoid, LLC, Newark, N.J. This phosphatidylcholine co-surfactant is derived from soy extract and contains greater than 95% phosphatidylcholine. The solvent is a Vitamin E oil, sold by ADM Natural Health and Nutrition, Decatur, Ill., under the name Novatol™ 5-67 Vitamin E (D-alpha-Tocopherol; ADM product code 410217). This oil contains at least 67.2% Tocopherol and approximately 32.8% soybean oil. The preservative is a natural (GRAS-certified) preservative, benzyl alcohol, and SALADIZER® brand emulsion stabilizer, which is obtained from TIC Gums, Inc., Belcamp, Md.

To make the water phase using the method described in Example 1, above, the following water phase ingredients are added sequentially, in the following order, to the water phase vessel: 1) water, 2) emulsion stabilizer. The emulsion stabilizer is the SALADIZER® brand emulsion stabilizer, which is obtained from TIC Gums, Inc., Belcamp, Md.

After forming the emulsion, an appropriate amount of citric acid (set forth in Table 4B(i)) is added in order to adjust the pH of the emulsion to between 2.6 and 3.4 as described in Example 1, above.

TABLE 4B(i)

Liquid Nanoemulsion Concentrate with 5% GLA-containing Non-Polar Compound (Borage Oil)

| Ingredient | mg/2 mL serving | Phase | Percent (by weight) of concentrate | g/batch |
|---|---|---|---|---|
| Vitamin E Oil (5-67) (solvent) | 75.00 | Oil | 3.750 | 18.75 |
| SALADIZER ® brand emulsion stabilizer (blend of xanthan gum, guar gum and sodium alginate) | 1.270 | Oil | 0.06 | 0.3 |
| Water | 1435 | Water | 71.74 | 358.7 |
| SALADIZER ® brand emulsion stabilizer (blend of xanthan gum, guar gum and sodium alginate) | 6.800 | Water | 0.34 | 1.7 |
| Polysorbate 80 (surfactant) | 355.0 | Oil | 17.75 | 88.75 |
| Phosphatidylcholine S-100 (co-surfactant) | 13.38 | Oil | 0.6690 | 3.345 |
| Benzyl Alcohol (preservative) | 10.00 | Oil | 0.5000 | 2.5000 |
| 22% GLA Borage oil | 100.0 | Oil | 5.0000 | 25.000 |
| Citric Acid (pH adjuster) | 3.800 | Emulsion | 0.1900 | 0.9500 |
| Totals | 2000.00 | | 100.000 | 500 |

Example 4B(ii)

Liquid Nanoemulsion Concentrate with 5% GLA-Containing Non-Polar Compound (Borage Oil)

Table 4B(ii), below, sets forth the ingredients for making a 250 g batch of an exemplary(Gamma Linoleic Acid) GLA-containing liquid nanoemulsion concentrate (2 mL serving size), which is made according to the procedure set forth in Example 1 above, with the following details and modifications:

To make the oil phase using the method described in Example 1, above, the following oil phase ingredients are added sequentially, in the following order, to the oil phase vessel: 1) surfactant; 2) preservative; 3) non-polar active ingredient; and 4) emulsion stabilizer.

The non-polar active ingredient is a borage oil compound, which is obtained from Sanmark LLC, Greensboro, N.C. (Sanmark Limited, Dalian, Liaoning Province, China), which is derived by pressing and isolating oil from the seeds of *Borago officinalis* L. This oil contains not less than (NLT) 22% C18:3 gamma-linolenic acid (GLA). The non-polar active ingredient is added at an amount such that the ingredient is 5%, by weight, of the final concentrate. The surfactant is a polysorbate 80 surfactant (which is purchased from Univar, Inc., Seattle, Wash.). The preservative is a natural (GRAS-certified) preservative, benzyl alcohol. The emulsion stabilizer is the SALADIZER® brand emulsion stabilizer, which is obtained from TIC Gums, Inc., Belcamp, Md.

To make the water phase using the method described in Example 1, above, the following water phase ingredients are added sequentially, in the following order, to the water phase vessel: 1) water, 2) emulsion stabilizer. The emulsion stabilizer is the SALADIZER® brand emulsion stabilizer, which is obtained from TIC Gums, Inc., Belcamp, Md.

After forming the emulsion, an appropriate amount of citric acid (set forth in Table 4B(ii)) is added in order to adjust the pH of the emulsion to between 2.6 and 3.4 as described in Example 1, above.

added sequentially, in the following order, to the oil phase vessel: 1) surfactant; 2) preservative; 3) non-polar active ingredient; and 4) emulsion stabilizer.

The non-polar active ingredient is a borage oil compound, which is obtained from Sanmark LLC, Greensboro, N.C. (Sanmark Limited, Dalian, Liaoning Province, China), which is derived by pressing and isolating oil from the seeds of *Borago officinalis* L. This oil contains not less than (NLT) 22% C18:3 gamma-linolenic acid (GLA). The non-polar active ingredient is added at an amount such that the ingredient is 10%, by weight, of the final concentrate. The surfactant is a polysorbate 80 surfactant (which is purchased from Univar, Inc., Seattle, Wash.). The preservative is a natural (GRAS-certified) preservative, benzyl alcohol. The emulsion stabilizer is the SALADIZER® brand emulsion stabilizer, which is obtained from TIC Gums, Inc., Belcamp, Md.

TABLE 4B(ii)

Liquid Nanoemulsion Concentrate with 5% GLA-containing Non-Polar Compound (Borage Oil)

| Ingredient | mg/2 mL serving | Phase | Percent (by weight) of concentrate | g/batch |
|---|---|---|---|---|
| Borage Oil (22% GLA) | 100 | Oil | 5 | 12.5 |
| Water | 1375.73 | Water | 68.7865 | 171.96625 |
| SALADIZER ® brand emulsion stabilizer (blend of xanthan gum, guar gum and sodium alginate) | 3.4 | Water | 0.17 | 0.425 |
| Polysorbate 80 (surfactant) | 504 | Oil | 25.2 | 63 |
| SALADIZER ® brand emulsion stabilizer (blend of xanthan gum, guar gum and sodium alginate) | 1.27 | Oil | 0.0635 | 0.15875 |
| Benzyl Alcohol (Preservative) | 10 | Oil | 0.5 | 1.25 |
| Citric Acid (pH adjuster) | 5.6 | Emulsion | 0.28 | 0.7 |
| Totals | 2000.000 | | 100.0000 | 250 |

Example 4B(iii)

Liquid Nanoemulsion Concentrate with 10% GLA-Containing Non-Polar Compound (Borage Oil)

Table 4B(iii), below, sets forth the ingredients for making a 250 g batch of an exemplary GLA-containing liquid nanoemulsion concentrate (2 mL serving size), which is made according to the procedure set forth in Example 1 above, with the following details and modifications:

To make the oil phase using the method described in Example 1, above, the following oil phase ingredients are To make the water phase using the method described in Example 1, above, the following water phase ingredients are added sequentially, in the following order, to the water phase vessel: 1) water, 2) emulsion stabilizer. The emulsion stabilizer is the SALADIZER® brand emulsion stabilizer, which is obtained from TIC Gums, Inc., Belcamp, Md.

After forming the emulsion, an appropriate amount of citric acid (set forth in Table 4B(iii)) is added in order to adjust the pH of the emulsion to between 2.6 and 3.4 as described in Example 1, above.

TABLE 4B(iii)

Liquid Nanoemulsion Concentrate with 10% GLA-containing Non-Polar Compound (Borage Oil)

| Ingredient | mg/2 mL serving | Phase | Percent (by weight) of concentrate | g/batch |
|---|---|---|---|---|
| Borage Oil (22% GLA) | 200 | Oil | 10 | 25 |
| Water | 1375.73 | Water | 68.7865 | 171.96625 |
| SALADIZER ® brand emulsion stabilizer (blend of xanthan gum, guar gum and sodium alginate) | 3.4 | Water | 0.17 | 0.425 |
| Polysorbate 80 (surfactant) | 404 | Oil | 20.2 | 50.5 |
| SALADIZER ® brand emulsion stabilizer (blend of xanthan gum, guar gum and sodium alginate) | 1.27 | Oil | 0.0635 | 0.15875 |
| Benzyl Alcohol (preservative) | 10 | Oil | 0.5 | 1.25 |

TABLE 4B(iii)-continued

Liquid Nanoemulsion Concentrate with 10% GLA-containing Non-Polar Compound (Borage Oil)

| Ingredient | mg/2 mL serving | Phase | Percent (by weight) of concentrate | g/batch |
|---|---|---|---|---|
| Citric Acid (pH adjuster | 5.6 | Emulsion | 0.28 | 0.7 |
| Totals | 2000.000 | | 100.0000 | 250 |

Example 4C

Liquid Nanoemulsion Concentrates with Conjugated Fatty Acid Containing Non-Polar Compounds Examples 4C(i)-4C(iii) set forth the details of formulations for making liquid nanoemulsion concentrates containing non-polar compounds that contain conjugated fatty acids (e.g. CLA). These concentrates can be made using the general procedure outlined in Example 1, above.

Example 4C(i)

Liquid Nanoemulsion Concentrate with 5% CLA-Containing Non-Polar Compound

Table 4C(i), below, sets forth the ingredients for making a 500 g batch of an exemplary CLA-containing liquid nanoemulsion concentrate (2 mL serving size), which is made according to the procedure set forth in Example 1 above, with the following details and modifications:

To make the oil phase using the method described in Example 1, above, the following oil phase ingredients are added sequentially, in the following order, to the oil phase vessel: 1) surfactant; 2) preservative; 3) solvent; 4) co-surfactant; 5) non-polar active ingredient; and 6) emulsion stabilizer.

The non-polar active ingredient is a conjugated linoleic acid (CLA) compound, which is obtained from Sanmark, LTD (Dalian, Liaoning Province, China; product code 01057-A80), containing 80% CLA. The non-polar active ingredient is added at an amount such that the ingredient is 5%, by weight, of the final concentrate. The surfactant is a polysorbate 80 surfactant (which is purchased from Univar, Inc., Seattle, Wash.). The co-surfactant is a phosphatidylcholine co-surfactant, sold under the trade name S-100, by Lipoid, LLC, Newark, N.J. This phosphatidylcholine co-surfactant is derived from soy extract and contains greater than 95% phosphatidylcholine. The solvent is a Vitamin E oil, sold by ADM Natural Health and Nutrition, Decatur, Ill., under the name Novatol™ 5-67 Vitamin E (D-alpha-Tocopherol; ADM product code 410217). This oil contains at least 67.2% Tocopherol and approximately 32.8% soybean oil. The preservative is a natural (GRAS-certified) preservative, benzyl alcohol. The emulsion stabilizer is the SALADIZER® brand emulsion stabilizer, which is obtained from TIC Gums, Inc., Belcamp, Md.

To make the water phase using the method described in Example 1, above, the following water phase ingredients are added sequentially, in the following order, to the water phase vessel: 1) water; 2) emulsion stabilizer. The emulsion stabilizer is the SALADIZER® brand emulsion stabilizer, which is obtained from TIC Gums, Inc., Belcamp, Md.

After forming the emulsion, an appropriate amount of citric acid (set forth in Table 4C(i)) is added in order to adjust the pH of the emulsion to between 2.6 and 3.4 as described in Example 1, above.

TABLE 4C(i)

Liquid Nanoemulsion Concentrate With 5% CLA-Containing Non-Polar Compound

| Ingredient | mg/2 mL serving | Phase | Percent (by weight) of concentrate | g/batch |
|---|---|---|---|---|
| Vitamin E Oil (5-67) (solvent) | 75.00 | Oil | 3.750 | 18.75 |
| SALADIZER ® brand emulsion stabilizer (blend of xanthan gum, guar gum and sodium alginate) | 1.270 | Oil | 0.06 | 0.3 |
| Water | 1435 | Water | 71.74 | 358.7 |
| SALADIZER ® brand emulsion stabilizer (blend of xanthan gum, guar gum and sodium alginate) | 6.800 | Water | 0.34 | 1.7 |
| Polysorbate 80 (surfactant) | 355.0 | Oil | 17.75 | 88.75 |
| Phosphatidylcholine S-100 (co-surfactant) | 13.38 | Oil | 0.6690 | 3.345 |
| Benzyl Alcohol (preservative) | 10.00 | Oil | 0.5000 | 2.5000 |
| 80% Conjugated Linoleic Acid Oil | 100.0 | Oil | 5.0000 | 25.000 |
| Citric Acid (pH adjuster) | 3.800 | emulsion | 0.1900 | 0.9500 |
| Totals | 2000.00 | | 100.000 | 500 |

Example 4C(ii)

Liquid Nanoemulsion Concentrate with 5% CLA-Containing Non-Polar Compound

Table 4C(ii), below, sets forth the ingredients for making a 250 g batch of an exemplary CLA-containing liquid nanoemulsion concentrate (2 mL serving size), which is made according to the procedure set forth in Example 1 above, with the following details and modifications:

To make the oil phase using the method described in Example 1, above, the following oil phase ingredients are added sequentially, in the following order, to the oil phase vessel: 1) surfactant; 2) preservative; 3) non-polar active ingredient; and 4) emulsion stabilizer.

The non-polar active ingredient is a conjugated linoleic acid (CLA) compound, which is obtained from Sanmark, LTD (Dalian, Liaoning Province, China; product code 01057-A80), containing 80% CLA. The non-polar active ingredient is added at an amount such that the ingredient is 5%, by weight, of the final concentrate. The surfactant is a polysorbate 80 surfactant (which is purchased from Univar, Inc., Seattle, Wash.). The preservative is a natural (GRAS-certified) preservative, benzyl alcohol. The emulsion stabilizer is the SALADIZER® brand emulsion stabilizer, which is obtained from TIC Gums, Inc., Belcamp, Md.

To make the water phase using the method described in Example 1, above, the following water phase ingredients are added sequentially, in the following order, to the water phase vessel: 1) water, 2) emulsion stabilizer. The emulsion stabilizer is the SALADIZER® brand emulsion stabilizer, which is obtained from TIC Gums, Inc., Belcamp, Md.

After forming the emulsion, an appropriate amount of citric acid (set forth in Table 4C(ii)) is added in order to adjust the pH of the emulsion to between 2.6 and 3.4 as described in Example 1, above.

Example 4C(iii)

Liquid Nanoemulsion Concentrate with 10% CLA-Containing Non-Polar Compound

Table 4C(iii), below, sets forth the ingredients for making a 250 g batch of an exemplary CLA-containing liquid nanoemulsion concentrate (2 mL serving size), which is made according to the procedure set forth in Example 1 above, with the following details and modifications:

To make the oil phase using the method described in Example 1, above, the following oil phase ingredients are added sequentially, in the following order, to the oil phase vessel: 1) surfactant; 2) preservative; 3) non-polar active ingredient; and 4) emulsion stabilizer.

The non-polar active ingredient is a conjugated linolenic acid (CLA) compound, which is obtained from Sanmark, LTD (Dalian, Liaoning Province, China; product code 01057-A80), containing 80% CLA. The non-polar active ingredient is added at an amount such that the ingredient is 10%, by weight, of the final concentrate. The surfactant is a polysorbate 80 surfactant (which is purchased from Univar, Inc., Seattle, Wash.). The preservative is a natural (GRAS-certified) preservative, benzyl alcohol. The emulsion stabilizer is the SALADIZER® brand emulsion stabilizer, which is obtained from TIC Gums, Inc., Belcamp, Md.

To make the water phase using the method described in Example 1, above, the following water phase ingredients are added sequentially, in the following order, to the water phase vessel: 1) water, 2) emulsion stabilizer. The emulsion stabilizer is the SALADIZER® brand emulsion stabilizer, which is obtained from TIC Gums, Inc., Belcamp, Md.

After forming the emulsion, an appropriate amount of citric acid (set forth in Table 4C(iii)) is added in order to adjust the pH of the emulsion to between 2.6 and 3.4 as described in Example 1, above.

TABLE 4C(ii)

Liquid Nanoemulsion Concentrate With 5% CLA-Containing Non-Polar Compound

| Ingredient | mg/2 mL serving | Phase | Percent (by weight) of concentrate | g/batch |
| --- | --- | --- | --- | --- |
| 80% Conjugated Linoleic Acid Oil | 100 | Oil | 5 | 12.5 |
| Water | 1375.73 | Water | 68.7865 | 171.96625 |
| SALADIZER ® brand emulsion stabilizer (blend of xanthan gum, guar gum and sodium alginate) | 3.4 | Water | 0.17 | 0.425 |
| Polysorbate 80 (surfactant) | 504 | Oil | 25.2 | 63 |
| SALADIZER ® brand emulsion stabilizer (blend of xanthan gum, guar gum and sodium alginate) | 1.27 | Oil | 0.0635 | 0.15875 |
| Benzyl Alcohol (preservative) | 10 | Oil | 0.5 | 1.25 |
| Citric Acid (pH adjuster) | 5.6 | Emulsion | 0.28 | 0.7 |
| Totals | 2000.000 | | 100.0000 | 250 |

TABLE 4C(iii)

Liquid Nanoemulsion Concentrate With 10% CLA-Containing Non-Polar Compound

| Ingredient | mg/2 mL serving | Phase | Percent (by weight) of concentrate | g/batch |
|---|---|---|---|---|
| 80% Conjugated Linoleic Acid Oil | 200 | Oil | 10 | 25 |
| Water | 1375.73 | Water | 68.7865 | 171.96625 |
| SALADIZER ® brand emulsion stabilizer (blend of xanthan gum, guar gum and sodium alginate) | 3.4 | Water | 0.17 | 0.425 |
| Polysorbate 80 (surfactant) | 404 | Oil | 20.2 | 50.5 |
| SALADIZER ® brand emulsion stabilizer (blend of xanthan gum, guar gum and sodium alginate) | 1.27 | Oil | 0.0635 | 0.15875 |
| Benzyl Alcohol (preservative) | 10 | Oil | 0.5 | 1.25 |
| Citric Acid (pH adjuster) | 5.6 | Emulsion | 0.28 | 0.7 |
| Totals | 2000.000 | | 100.0000 | 250 |

Example 4D

Liquid Nanoemulsion Concentrates with Saw Palmetto Extract Non-Polar Compounds

Examples 4D(i)-4D(iii) set forth the details of formulations for making liquid nanoemulsion concentrates containing non-polar compounds that contain Saw Palmetto Extract. These concentrates can be made using the general procedure outlined in Example 1, above.

Example 4D(i)

Liquid Nanoemulsion Concentrate with 5% of a Saw Palmetto Extract Non-Polar Compound Table 4D(i), below, sets forth the ingredients for making a 250 g batch of an exemplary Saw Palmetto extract-containing liquid nanoemulsion concentrate (2 mL serving size), which is made according to the procedure set forth in Example 1 above, with the following details and modifications:

To make the oil phase using the method described in Example 1, above, the following oil phase ingredients are added sequentially, in the following order, to the oil phase vessel: 1) surfactant; 2) preservative; 3) solvent; 4) co-surfactant; 5) non-polar active ingredient; and 6) emulsion stabilizer.

The non-polar active ingredient is a Saw Palmetto extract, the Saw Palmetto, Lipophilic Extract, commercially available from Natural Medicinals, Inc., Felda, Fla., which contains about 90% total fatty acids, including 0.8% Caproic acid, 2% Caprylic acid, 2.4% Capric acid, 27.1 Lauric acid, 10.3 Myristic acid, 8.1% Palmitic acid, 0.2% Palmitoleic acid, 2% Stearic acid, 26.7 Oleic acid, 4.9% Linoleic acid, 0.7% linolenic acid, 0.42%; 0.42% phytosterols, including 0.42% beta Sitosterol, 0.09% Campesterol, 0.03% Stigmasterol; and 0.2% moisture. The non-polar active ingredient is added at an amount such that the ingredient is 5%, by weight, of the final concentrate.

The surfactant is a polysorbate 80 surfactant (which is purchased from Univar, Inc., Seattle, Wash.). The co-surfactant is a phosphatidylcholine co-surfactant, sold under the trade name S-100, by Lipoid, LLC, Newark, N.J. This phosphatidylcholine co-surfactant is derived from soy extract and contains greater than 95% phosphatidylcholine. The solvent is a Vitamin E oil, sold by ADM Natural Health and Nutrition, Decatur, Ill., under the name Novatol™ 5-67 Vitamin E (D-alpha-Tocopherol; ADM product code 410217). This oil contains at least 67.2% Tocopherol and approximately 32.8% soybean oil. The preservative is a natural (GRAS-certified) preservative, benzyl alcohol. The emulsion stabilizer is the SALADIZER® brand emulsion stabilizer, which is obtained from TIC Gums, Inc., Belcamp, Md.

To make the water phase using the method described in Example 1, above, the following water phase ingredients are added sequentially, in the following order, to the water phase vessel: 1) water, 2) emulsion stabilizer. The emulsion stabilizer is SALADIZER® brand emulsion stabilizer, which is obtained from TIC Gums, Inc., Belcamp, Md.

After forming the emulsion, an appropriate amount of citric acid (set forth in Table 4D(i)) is added in order to adjust the pH of the emulsion to between 2.6 and 3.4 as described in Example 1, above.

TABLE 4D(i)

Liquid Nanoemulsion Concentrate with 5% of a Saw Palmetto Extract Non-Polar Compound

| Ingredient | mg/2 mL serving | Phase | Percent (by weight) of concentrate | g/batch |
|---|---|---|---|---|
| Vitamin Oil (5-67) | 75.00 | Oil | 3.750 | 9.375 |
| SALADIZER ® brand emulsion stabilizer (blend of xanthan gum, guar gum and sodium alginate) | 1.270 | Oil | 0.06 | 0.2 |
| Water | 1435 | Water | 71.74 | 179.3 |
| SALADIZER ® brand emulsion stabilizer (blend of xanthan gum, guar gum and sodium alginate) | 6.800 | Water | 0.34 | 0.9 |

TABLE 4D(i)-continued

Liquid Nanoemulsion Concentrate with 5% of a Saw Palmetto Extract Non-Polar Compound

| Ingredient | mg/2 mL serving | Phase | Percent (by weight) of concentrate | g/batch |
|---|---|---|---|---|
| Polysorbate 80 (surfactant) | 355.0 | Oil | 17.75 | 44.38 |
| Phosphatidylcholine S-100 (co-surfactant) | 13.38 | Oil | 0.6690 | 1.673 |
| Benzyl Alcohol (preservative) | 10.00 | Oil | 0.5000 | 1.2500 |
| Saw Palmetto Oil (90% Fatty acids) | 100.0 | Oil | 5.0000 | 12.500 |
| Citric Acid (pH adjuster) | 3.800 | Emulsion | 0.1900 | 0.4750 |
| Totals | 2000.00 | | 100.000 | 250 |

Example 4D(ii)

Liquid Nanoemulsion Concentrate with 5% of a Saw Palmetto Extract Non-Polar Compound Table 4D(ii), below, sets forth the ingredients for making a 250 g batch of an exemplary Saw Palmetto extract-containing liquid nanoemulsion concentrate (2 mL serving size), which is made according to the procedure set forth in Example 1 above, with the following details and modifications:

To make the oil phase using the method described in Example 1, above, the following oil phase ingredients are added sequentially, in the following order, to the oil phase vessel: 1) surfactant; 2) preservative; 3) non-polar active ingredient; and 4) emulsion stabilizer.

The non-polar active ingredient is a Saw Palmetto extract, the Saw Palmetto, Lipophilic Extract, commercially available from Natural Medicinals, Inc., Felda, Fla., which contains about 85-90% total fatty acids, including 0.8% Caproic acid, 2% Caprylic acid, 2.4% Capric acid, 27.1 Lauric acid, 10.3 Myristic acid, 8.1% Palmitic acid, 0.2% Palmitoleic acid, 2% Stearic acid, 26.7 Oleic acid, 4.9% Linoleic acid, 0.7% linolenic acid, 0.42%; 0.42% phytosterols, including 0.42% beta Sitosterol, 0.09% Campesterol, 0.03% Stigmasterol; and 0.2% moisture. The non-polar active ingredient is added at an amount such that the ingredient is 5%, by weight, of the final concentrate. The surfactant is a polysorbate 80 surfactant (which is purchased from Univar, Inc., Seattle, Wash.). The preservative is a natural (GRAS-certified) preservative, benzyl alcohol. The emulsion stabilizer is the SALADIZER® brand emulsion stabilizer, which is obtained from TIC Gums, Inc., Belcamp, Md.

To make the water phase using the method described in Example 1, above, the following water phase ingredients are added sequentially, in the following order, to the water phase vessel: 1) water, 2) emulsion stabilizer. The emulsion stabilizer is the SALADIZER® brand emulsion stabilizer, which is obtained from TIC Gums, Inc., Belcamp, Md.

After forming the emulsion, an appropriate amount of citric acid (set forth in Table 4D(ii)) is added in order to adjust the pH of the emulsion to between 2.6 and 3.4 as described in Example 1, above.

TABLE 4D(ii)

Liquid Nanoemulsion Concentrate with 5% of a Saw Palmetto Extract Non-Polar Compound

| Ingredient | mg/2 mL serving | Phase | Percent (by weight) of concentrate | g/batch |
|---|---|---|---|---|
| Saw Palmetto Oil 85-90% Fatty acids | 100 | Oil | 5 | 12.5 |
| Water | 1375.73 | Water | 68.7865 | 171.96625 |
| SALADIZER ® brand emulsion stabilizer (blend of xanthan gum, guar gum and sodium alginate) | 3.4 | Water | 0.17 | 0.425 |
| Polysorbate 80 (surfactant) | 504 | Oil | 25.2 | 63 |
| SALADIZER ® brand emulsion stabilizer (blend of xanthan gum, guar gum and sodium alginate) | 1.27 | Oil | 0.0635 | 0.15875 |
| Benzyl Alcohol (preservative) | 10 | Oil | 0.5 | 1.25 |
| Citric Acid (pH adjuster) | 5.6 | Emulsion | 0.28 | 0.7 |
| Totals | 2000.000 | | 100.0000 | 250 |

Example 4D(iii)

Liquid Nanoemulsion Concentrate with 10% of a Saw Palmetto Extract Non-Polar Compound Table 4D(iii), below, sets forth the ingredients for making a 250 g batch of an exemplary Saw Palmetto extract-containing liquid nanoemulsion concentrate (2 mL serving size), which is made according to the procedure set forth in Example 1 above, with the following details and modifications:

To make the oil phase using the method described in Example 1, above, the following oil phase ingredients are added sequentially, in the following order, to the oil phase vessel: 1) surfactant; 2) preservative; 3) non-polar active ingredient; and 4) emulsion stabilizer.

The non-polar active ingredient is a Saw Palmetto extract, the Saw Palmetto, Lipophilic Extract, commercially available from Natural Medicinals, Inc., Felda, Fla., which contains about 85-90% total fatty acids, including 0.8% Caproic acid, 2% Caprylic acid, 2.4% Capric acid, 27.1 Lauric acid, 10.3 Myristic acid, 8.1% Palmitic acid, 0.2% Palmitoleic acid, 2% Stearic acid, 26.7 Oleic acid, 4.9% Linoleic acid, 0.7% linolenic acid, 0.42%; 0.42% phytosterols, including 0.42% beta Sitosterol, 0.09% Campesterol, 0.03% Stigmasterol; and 0.2% moisture. The non-polar active ingredient is added at an amount such that the ingredient is 10%, by weight, of the final concentrate. The surfactant is a polysorbate 80 surfactant (which is purchased from Univar, Inc., Seattle, Wash.). The preservative is a natural (GRAS-certified) preservative, benzyl alcohol. The emulsion stabilizer is the SALADIZER® brand emulsion stabilizer, which is obtained from TIC Gums, Inc., Belcamp, Md.

To make the water phase using the method described in Example 1, above, the following water phase ingredients are added sequentially, in the following order, to the water phase vessel: 1) water, 2) emulsion stabilizer. The emulsion stabilizer is the SALADIZER® brand emulsion stabilizer, which is obtained from TIC Gums, Inc., Belcamp, Md.

After forming the emulsion, an appropriate amount of citric acid (set forth in Table 4D(iii)) is added in order to adjust the pH of the emulsion to between 2.6 and 3.4 as described in Example 1, above.

according to the procedure set forth in Example 1 above, with the following details and modifications:

To make the oil phase using the method described in Example 1, above, the following oil phase ingredients are added sequentially, in the following order, to the oil phase vessel: 1) surfactant; 2) preservative; 3) solvent; 4) co-surfactant; 5) non-polar active ingredient; and 6) emulsion stabilizer.

The non-polar active ingredient is a Phytosterols compound, sold under the name CardioAid™, distributed by B&D Nutrition and manufactured by ADM Natural Health and Nutrition, Decatur, Ill. This compound contains Kosher, Pareve, and Halal plant sterols that are produced under current food GMPs and contains a minimum of 95% plant sterols. The non-polar active ingredient is added at an amount such that the ingredient is 5.25%, by weight, of the final concentrate. The surfactant is a polysorbate 80 surfactant (which is purchased from Univar, Inc., Seattle, Wash.). The co-surfactant is a phosphatidylcholine co-surfactant, sold under the trade name S-100, by Lipoid, LLC, Newark, N.J. This phosphatidylcholine co-surfactant is derived from soy extract and contains greater than 95% phosphatidylcholine. The solvent is a Flaxseed oil, which is obtained from Sanmark TABLE 4D(iii)

Liquid Nanoemulsion Concentrate with 10% of a Saw Palmetto Extract Non-Polar Compound

| Ingredient | mg/2 mL serving | Phase | Percent (by weight) of concentrate | g/batch |
|---|---|---|---|---|
| Saw Palmetto Oil 85-90% Fatty acids | 200 | Oil | 10 | 25 |
| Water | 1375.73 | Water | 68.7865 | 171.96625 |
| SALADIZER ® brand emulsion stabilizer (blend of xanthan gum, guar gum and sodium alginate) | 3.4 | Water | 0.17 | 0.425 |
| Polysorbate 80 (surfactant) | 404 | Oil | 20.2 | 50.5 |
| SALADIZER ® brand emulsion stabilizer (blend of xanthan gum, guar gum and sodium alginate) | 1.27 | Oil | 0.0635 | 0.15875 |
| Benzyl Alcohol (preservative) | 10 | Oil | 0.5 | 1.25 |
| Citric Acid (pH adjuster) | 5.6 | Emulsion | 0.28 | 0.7 |
| Totals | 2000.000 | | 100.0000 | 250 |

Example 5

Liquid Nanoemulsion Concentrates with Phytosterol-Containing Non-Polar Compounds Example 6A sets forth the details of formulations for making a liquid nanoemulsion concentrate containing non-polar compounds that contain Phytosterols. This concentrate can be made using the general procedure outlined in Example 1, above.

Example 5A

Liquid Nanoemulsion Concentrate with 5.25% Phytosterols Non-Polar Compound

Table 5A, below, sets forth the ingredients for making a 250 g batch of an exemplary phytosterols-containing liquid nanoemulsion concentrate (2 mL serving size), which is made LLC, Greensboro, N.C. (Sanmark Limited, Dalian, Liaoning Province, China), which contains not less than (NLT) 50% C18:3 alpha-linolenic acid. The preservative is a natural (GRAS-certified) preservative, benzyl alcohol. The emulsion stabilizer is the SALADIZER® brand emulsion stabilizer, which is obtained from TIC Gums, Inc., Belcamp, Md.

To make the water phase using the method described in Example 1, above, the following water phase ingredients are added sequentially, in the following order, to the water phase vessel: 1) water, 2) emulsion stabilizer; and 3) pH adjuster.

The emulsion stabilizer is the SALADIZER® brand emulsion stabilizer, which is obtained from TIC Gums, Inc., Belcamp, Md. The pH adjuster is phosphoric acid, which is added at the indicated concentration to ensure the pH of the concentrate is between about 2.6 and 3.4.

After forming the emulsion, the pH of the concentrate is measured with a pH meter, as described in Example 1, above, to make sure it is between 2.6 and 3.4.

TABLE 5A

Liquid Nanoemulsion Concentrate with 5.25% Phytosterols Non-Polar Compound

| Ingredient | mg/2 mL serving | Phase | Percent (by weight) of concentrate | g/batch |
|---|---|---|---|---|
| Flaxseed oil (50% ALA) | 105.00 | Oil | 5.25 | 13.13 |
| Water | 1365.70 | Water | 68.29 | 170.71 |
| SALADIZER ® brand emulsion stabilizer (blend of xanthan gum, guar gum and sodium alginate) | 3.30 | Water | 0.17 | 0.41 |
| Polysorbate 80 (surfactant) | 400.00 | Oil | 20.00 | 50.00 |
| Phosphatidylcholine (co-surfactant) | 3.00 | Oil | 0.15 | 0.38 |
| Benzyl Alcohol (preservative) | 10.00 | Oil | 0.50 | 1.25 |
| PHYTOSTEROLS | 105.00 | Oil | 5.25 | 13.13 |
| Phosphoric Acid (pH adjuster) | 8.00 | Water | 0.40 | 1.00 |
| Totals | 2000.00 | | 100.00 | 250.00 |

Example 6

Dilution of the Liquid Nanoemulsion Concentrates and Evaluation of the Liquid Dilution Compositions For evaluation of various properties, any of the liquid nanoemulsion concentrates, described in the Examples above, can be diluted, according to the provided methods, in aqueous medium to form aqueous liquid dilution compositions.

For example, the concentrates could be diluted in aqueous medium, according to the provided methods for diluting the concentrates. The resulting aqueous liquid dilution compositions then could be evaluated for clarity by measuring turbidity using a nephelometer. In one example, the liquid nanoemulsion concentrates can be diluted by adding an amount of concentrate (e.g. 1 g) to an amount of aqueous medium, typically water (e.g. 100 ml, 250 mL, 500 mL, 1000 mL).

In one example, for diluting the concentrates, the water is heated in a Pyrex® beaker, by placing the beaker on a Thermolyne hot plate (Model #846925), until the water reaches 49.8° C. The liquid nanoemulsion concentrate then is added to the heated water, and stirred with a stir rod until dispersed. The resulting aqueous liquid dilution composition containing the non-polar active ingredient can be cooled to room temperature (about 25° C.). The cooled liquid dilution composition can be added to an amber-glass screw-top vial (Alcon), for evaluation. The vials containing the liquid dilution compositions then can be analyzed, for example, by sending the samples to ACZ Laboratories, Inc., Steamboat Springs, Colo., for turbidity analysis using a nephelometer, which obtains results in the form of Nephelometric Turbidity Units (NTU).

In another example, the liquid nanoemulsion concentrates can be diluted for particle size analysis. In one example, the dilution can be carried out as above, and particle size analyzed by viewing the liquid dilution composition under a microscope. In another example, the concentrate can be sent out for analysis, e.g. to Delta Analytical Instruments, Inc., for measurement of particle size which is performed by diluting the concentrate and then analyzing using the Horiba® LB-550 light-scattering analyzer. For this process, the liquid nanoemulsion concentrate is mixed well and three drops of the concentrate are added to 25 mL of water. The sample then is put into a cell, which is used to measure average particle size on the Horiba® LB-550 light-scattering analyzer. Typically, average particle size is measured in multiple separate runs, the results of which are averaged. Alternatively, other analyses described herein can be done.

Example 7

General Exemplary Procedure used to Make the Liquid Nanoemulsion Concentrates using the Exemplary Formulation in Example 8

Table 8A, below, sets forth ingredients that were used to make a liquid nanoemulsion concentrate, described in further detail in Example 8, according to the provided methods. The nanoemulsion concentrate contained one or more non-polar active ingredients.

Table 8A sets forth the milligrams (mg) per serving (serving size is indicated) of each ingredient in the concentrate, the percentage, by weight (of the total concentrate), for each ingredient and the amount (g) of each ingredient per batch of the indicated batch size (g). Also indicated in each table, in the "phase" column, is whether each ingredient was added to the water phase ("water"), the oil phase ("oil") or was added later, to the emulsion that was formed by emulsifying the oil and water phases ("emulsion").

The liquid nanoemulsion concentrate set forth in Example 8 was made using a bench-top process according to the provided methods, as described in this Example. Alternatively, this concentrate can be made by scaling up the bench-top process, to make the concentrate using a scaled-up manufacturing process of the provided methods, for example, to make larger batch sizes of the concentrate in the following Example. Accordingly, the concentrate in Example 8 also can be made with the provided methods, using the scaled-up process.

The bench-top process for making the concentrate in Example 8 was performed using the following general steps, except where indicated in the specific examples. Further details for the concentrates are provided in each individual example.

To make the liquid nanoemulsion concentrate set forth in Example 8 below, the indicated amount of each ingredient was weighed using a Toledo Scale (Model GD13x/USA), Sartorius Basic Analytical Scale (Model BA110S) or an OHAUS Scale (Model CS2000). Selection of scale(s) depended on the weight of the particular ingredient(s).

To make the water phase, water phase ingredients (indicated by "water" in each table in the "phase" column) were added, in the indicated amounts (g/batch), to a water phase vessel (a Pyrex® beaker), and mixed using a reversible homogenizer (Arde Barinco, Inc.; Model CJ-4E), at 30 RPM. The water phase of each exemplary concentrate contained water, which was purified city water, purified according to the provided methods by passage through the following purifiers, sequentially: a carbon filter, an ion exchange purifier, a reverse osmosis purifier and an end-point filter, for example, a 100 micron end-point filter, before being added to the water phase tank.

While mixing, the water phase ingredients were heated using a heating apparatus. The heating apparatus was a hot plate (a Thermolyne hot Plate Model # SP46615, Barnstead International, Dubuque, Iowa). Except where indicated, when the water phase included water and an emulsion stabilizer, these ingredients were added sequentially, in the following order: 1) water; 2) emulsion stabilizer.

The water phase ingredients were heated with the hot plate until the temperature reached 60° C. The water phase then was maintained at 60° C. before combining and emulsifying the water and oil phases. A temperature meter (temperature probe (Model # DPP400W, Cooper-Atkins)) was used to evaluate (measure) the temperature of the water phase.

The oil phase ingredients (indicated by "oil" in each table in the "phase" column) were added to an oil phase vessel (a Pyrex® beaker), and mixed using a standard mixer (IKA® model No. RE-16 1S, which is an overhead mixer (laboratory stirrer) compatible with the bench-top process). In general, unless otherwise indicated, when the oil phase included two or more of a surfactant, preservative, solvent, co-surfactant, non-polar compound and emulsion stabilizer, these ingredients were added sequentially, in the following order: 1) surfactant; 2) preservative; 3) solvent; 4) co-surfactant; 5) non-polar compound; and 6) emulsion stabilizer. For example, when the oil phase included surfactant, preservative and non-polar compound, these ingredients were added in the following order (unless otherwise indicated): 1) surfactant, 2) preservative; 3) non-polar compound.

As the oil phase ingredients were mixed, they were heated using a heating apparatus. The heating apparatus was a hot plate (a Thermolyne hot Plate Model # SP46615, Barnstead International, Dubuque, Iowa). The oil phase ingredients were heated until the mixture reached 60° C. The oil phase was mixed at this temperature until all the ingredients had dissolved, and maintained at 60° C. before mixing with the water phase. A temperature meter (temperature probe (Model # DPP400W, Cooper-Atkins)) was used to evaluate (measure) the temperature of the oil phase.

After both phases had reached 60° C. and the oil phase components had dissolved, the phases were combined and emulsified using the following steps. A reversible homogenizer (Arde Barinco, Inc.; Model CJ-4E) was placed in the water phase vessel and turned on at 30 RPM. The oil phase then was transferred to the water phase vessel by pouring the oil phase from the oil phase vessel into the water phase vessel. Mixing with the homogenizer was continued, with adjustment of the baffle plate on the homogenizer to achieve and maintain an emulsion, for example, by moving the baffle plate further into the forming emulsion and/or out of the forming emulsion.

Homogenization of the forming emulsion was continued at 30 rpm, with rapid cooling. Rapid cooling was effected by placing the water phase vessel (beaker), containing the forming emulsion, in a water bath, to cool the forming emulsion until the temperature of the liquid reached between 25° C. and 43° C. (typically taking between about 30 and about 60 minutes).

After emulsifying and rapidly cooling, additional ingredients were added, where indicated in the individual Example/Table. For example, any ingredient that was added subsequent to the emulsifying step (instead of to one of the individual phases) is indicated by the word "emulsion" in the "phase" column. The emulsion was mixed while adding any additional ingredients, using the standard mixer (IKA® model No. RE-16 1S). Exemplary of additional ingredients that were added in the following examples are flavors (D-limonene and lemon oil), and pH adjusters (e.g. citric acid). In several examples (where indicated), the pH of the emulsion was measured using a pH and temperature meter (Hanna Instruments, model HI 8314). When needed, the pH was adjusted with the appropriate amount of a pH adjuster (amount indicated in tables), for example, citric acid or phosphoric acid, until the emulsion reached a pH of between 2.6 and 3.2. Each of the concentrates produced in the following Examples had a pH of between about 2.6 and 3.2.

As a final step, the concentrate was filtered using a 100 micron end-product filter, before further evaluation, dilution and/or use.

Example 8

Liquid Nanoemulsion Concentrates with PUFA-Containing Non-Polar Compounds

Example 8A sets forth the details of a liquid nanoemulsion concentrate that was made and contained non-polar compounds that include polyunsaturated fatty acids (PUFAs). The concentrate made in this example contained omega-3 fatty acid non-polar active ingredients (e.g. ingredients containing DHA, EPA, ALA and combinations thereof). The same formulations can be used to make concentrates containing other non-polar active ingredients, for example, non-polar active ingredients containing ingredients selected from any one or more of omega-3 fatty acids, omega-6 fatty acids, conjugated fatty acids and other fatty acids. The concentrate in Example 8A below was made using the general procedure outlined in Example 7, above.

Example 8A

Liquid Nanoemulsion Concentrate with 2.5% of Omega 3-Containing Non-Polar Compounds (Flaxseed Oil and Fish Oil)

Table 8A, below, sets forth the ingredients for making a 250 g batch of an exemplary omega 3-containing (ALA, DHA, EPA) liquid nanoemulsion concentrate (2 mL serving size), which is made according to the procedure set forth in Example 7 above, with the following details and modifications:

To make the oil phase using the method described in Example 7, above, the following oil phase ingredients are added sequentially, in the following order, to the oil phase vessel: 1) surfactant; 2) preservative; 3) emulsion stabilizer; and 4) non-polar active ingredients.

The omega-3 fatty acid non polar active ingredients included:

Flaxseed oil, obtained from Sanmark LLC, Greensboro, N.C. (Sanmark Limited, Dalian, Liaoning Province, China), which contains not less than (NLT) 50% C18:3 alpha-linolenic acid. The flaxseed oil was added at an amount such that the active ingredient is 2.5%, by weight of the final concentrate; and Fish oil, containing about 30% DHA/EPA (sold under the name Omega 30 TG Food Grade (Non-GMO) MEG-3™ Fish Oil by Ocean Nutrition Canada Limited, Nova Scotia, Mass.). The fish oil non-polar active ingredient was added at an amount of 0.1%, by weight of the final concentrate, whereby the concentrate contained 0.03% EPA+DHA.

The surfactant is polysorbate 80 surfactant (which is purchased from Univar, Inc., Seattle, Wash.). The preservative is a natural (GRAS-certified) preservative, benzyl alcohol. The emulsion stabilizer is the SALADIZER® brand emulsion stabilizer, obtained from TIC Gums, Inc., Belcamp, Md.

To make the water phase using the method described in Example 8, above, the following water phase ingredients are added sequentially, in the following order, to the water phase vessel: 1) water; 2) emulsion stabilizer. The emulsion stabilizer is the SALADIZER® brand emulsion stabilizer, which is obtained from TIC Gums, Inc., Belcamp, Md.

After forming the emulsion, an appropriate amount of citric acid (set forth in Table 8A) is added in order to adjust the pH of the emulsion to between 2.6 and 3.4 as described in Example 7, above.

TABLE 8A

Liquid Nanoemulsion Concentrate with 2.5% of Omega 3-Containing Non-Polar Compounds (Flaxseed Oil and Fish Oil)

| Ingredient | mg/2 mL serving | Phase | Percent (by weight) of concentrate | g/batch |
|---|---|---|---|---|
| Flaxseed Oil (55% Omega-3 ALA) | 100 | Oil | 5.0 | 12.5 |
| Ocean Nutrition MEG-3 ™ (30% Omega-3) | 2 | Oil | 0.10 | 0.25 |
| Water | 1373.73 | Water | 68.687 | 171.72 |
| SALADIZER ® brand emulsion stabilizer (blend of xanthan gum, guar gum and sodium alginate) | 3.4 | Water | 0.17 | 0.43 |
| Polysorbate 80 (surfactant) | 504 | Oil | 25.2 | 63.00 |
| SALADIZER ® brand emulsion stabilizer (blend of xanthan gum, guar gum and sodium alginate) | 1.27 | Oil | 0.0635 | 0.16 |
| Benzyl alcohol (preservative) | 10 | Oil | 0.5 | 1.25 |
| Citric Acid (pH adjuster) | 5.60 | Emulsion | 0.28 | 0.70 |
| Totals | 2000.000 | | 100.0000 | 250 |

Since modifications will be apparent to those of skill in this art, it is intended that this invention be limited only by the scope of the appended claims.

The invention claimed is:

1. A liquid nanoemulsion concentrate, comprising:
polysorbate or a polyoxyethylene sorbitan monooleate (polysorbate 80) analog in an amount between about 17% and about 26%, inclusive, by weight, of the concentrate;
water in an amount between about 60% and about 79%, inclusive, by weight, of the concentrate;
a non-polar ingredient that is selected from among any one or more of polyunsaturated fatty acids, Coenzyme Q10 compounds, and phytosterols in an amount between about 5% and about 10%, inclusive, by weight, of the concentrate, wherein the non-polar ingredient contains at least one polyunsaturated fatty acid selected from among any one or more of omega-3 fatty acids, omega-6 fatty acids and conjugated fatty acids.

2. The liquid nanoemulsion concentrate of claim 1, wherein the amount of water is between about 65% and about 76%, or between about 68% and about 76%, by weight, of the concentrate.

3. The liquid nanoemulsion concentrate of claim 1, wherein polysorbate 80 analog is a polysorbate 80 homolog.

4. The liquid nanoemulsion concentrate of claim 3, wherein the polysorbate 80 homolog differs from polysorbate 80 by one or more methylene unit(s).

5. The liquid nanoemulsion concentrate of claim 3, wherein the polysorbate 80 analog is polysorbate 60, polysorbate 40, or polysorbate 20.

6. The liquid nanoemulsion concentrate of claim 1, wherein the amount of polysorbate or a polysorbate 80 analog is between about 18% and about 26%.

7. The liquid nanoemulsion concentrate of claim 1, wherein the non-polar ingredient contains a polyunsaturated fatty acid selected from among a docosahexaenoic acid (DHA), an eicosapentaenoic acid (EPA), a fish oil, a flaxseed oil, a borage oil, an alpha-linolenic acid (ALA), a gamma-linolenic acid (GLA), a conjugated linoleic acid (CLA), and a saw palmetto extract.

8. The liquid nanoemulsion concentrate of claim 7, wherein the amount of DHA is between about 20% and about 90%; or between about 25% and about 85%; or between about 35% and about 70%; or between about 25% and about 40%, by weight, of the non-polar ingredient.

9. The liquid nanoemulsion concentrate of claim 7, wherein the amount of EPA is between about 5% and about 15%, or between about 5% and about 13%, or between about 5% and about 10%, by weight, of the non-polar ingredient.

10. The liquid nanoemulsion concentrate of claim 7, wherein the amount of ALA is between about 50% and about 80%, or between about 65% and about 75%, by weight, of the non-polar ingredient.

11. The liquid nanoemulsion concentrate of claim 7, wherein the amount of GLA is at least about 22%, by weight, of the non-polar ingredient.

12. The liquid nanoemulsion concentrate of claim 1, wherein the non-polar ingredient contains a Coenzyme Q10 compound and the Coenzyme Q10 compound is ubidecarenone.

13. The liquid nanoemulsion concentrate of claim 1, further comprising a co-surfactant in an amount sufficient to stabilize the concentrate.

14. The liquid nanoemulsion concentrate of claim 13, wherein the co-surfactant contains a phospholipid.

15. The liquid nanoemulsion concentrate of claim 14, wherein the phospholipid comprises phosphatidylcholine.

16. The liquid nanoemulsion concentrate of claim 1, further comprising a preservative, in amount sufficient to preserve the concentrate.

17. The liquid nanoemulsion concentrate of claim 16, wherein preservative contains benzyl alcohol.

18. The liquid nanoemulsion concentrate of claim 1, further comprising a solvent that dissolves the non-polar ingredient and differs therefrom, wherein the amount of solvent is sufficient to dissolve the non-polar ingredient.

19. The liquid nanoemulsion concentrate of claim 18, wherein the solvent contains a Vitamin E oil, a flaxseed oil, or a combination thereof.

20. The liquid nanoemulsion concentrate of claim 1, comprising from about 0.1% to less than 1% of an emulsion stabilizer.

21. The liquid nanoemulsion concentrate of claim 1, further comprising one or more flavors in an amount sufficient to enhance the taste of the concentrate, the smell of the concentrate, or a combination thereof.

22. The liquid nanoemulsion concentrate of claim 21, wherein the one or more flavors contains lemon oil, D-limonene, or a combination thereof.

23. The liquid nanoemulsion concentrate of claim 1, wherein the concentrate is formulated such that:
(a) dilution of at least 0.5 g or about 0.5 g, at least 1 g or about 1 g, at least 2 g or about 2 g, at least 5 g or about 5 g, or at least 10 g or about 10 g of the concentrate into 8 fluid ounces (0.236588 liters), or about 8 fluid ounces, of an aqueous medium; or
(b) dilution of the concentrate in an aqueous medium, at a dilution of not more than 1:10 or about 1:10, not more than 1:25 or about 1:25, not more than 1:50 or about 1:50, not more than 1:100 or about 1:100, not more than 1:250 or about 1:250, or not more than 1:500 or about 1:500; or
(c) dilution of the concentrate into an aqueous medium to form a liquid dilution composition containing at least 25 mg or about 25 mg, at least 35 mg or about 35 mg, at least 50 mg or about 50 mg, at least 100 mg or about 100 mg, at least 250 mg or about 250 mg, or at least 500 mg or about 500 mg of the non-polar active ingredient per 8 fluid ounces of the liquid dilution composition,
yields a liquid dilution composition:
(i) having a particle size of less than about 200 nm, less than about 100 nm, less than about 50 nm, or less than about 25 nm, at most or on average; or
(ii) having a Nephelometric Turbidity Units (NTU) value of less than 200 or about 200, less than 100 or about 100, less than 50 or about 50, less than 30 or about 30, less than 25 or about 25, or less than 10 or about 10; or
(iii) that does not contain visible particles, does not contain visible crystals, does not exhibit phase separation, and/or does not exhibit ringing; or
(iv) that is at least as clear or at least about as clear as, the aqueous medium in the absence of the concentrate; or
(v) that remains free from visible particles, remains free from visible crystals, remains free from phase separation, and/or remains free from ringing, when stored at room temperature, or at a refrigerated temperature, or at a frozen temperature, wherein the storage is for at least one day, at least one week, at least thirty days, or at least one year.

24. A liquid dilution composition, comprising the liquid nanoemulsion concentrate of claim 1, diluted in an aqueous medium, wherein:
(a) the composition contains at least 0.5 grams (g) or about 0.5 g, at least 1 g or about 1 g, at least 2 g or about 2 g, at least 5 g or about 5 g, or at least 10 g or about 10 g of the concentrate, per 8 fluid ounces (0.236588 liters) of the aqueous medium; or
(b) the composition contains the concentrate at a dilution of not more than 1:10 or about 1:10, not more than 1:25 or about 1:25, not more than 1:50 or about 1:50, not more than 1:100 or about 1:100, not more than 1:250 or about 1:250, or not more than 1:500 or about 1:500; or
(c) the composition contains at least 25 mg or about 25 mg, at least 35 mg or about 35 mg, at least 50 mg or about 50 mg, at least 100 mg or about 100 mg, at least 250 mg or about 250 mg, or at least 500 mg or about 500 mg of the non-polar active ingredient per 8 fluid ounces of the aqueous medium; and
the liquid dilution composition:
(i) has a particle size of less than about 200 nm, less than about 100 nm, less than about 50 nm, or less than about 25 nm, on average or at the most; or
(ii) has a Nephelometric Turbidity Units (NTU) value of less than 200 or about 200, less than 100 or about 100, less than 50 or about 50, less than 30 or about 30, less than 25 or about 25, or less than 10 or about 10; or
(ii) has a Nephelometric Turbidity Units (NTU) value of less than 200 or about 200, less than 100 or about 100, less than 50 or about 50, less than 30 or about 30, less than 25 or about 25, or less than 10 or about 10; or
(iii) does not contain visible particles, does not contain visible crystals, does not exhibit ringing, and/or does not exhibit phase separation; or
(iv) is as clear or about as clear as the aqueous medium in the absence of the concentrate; or
(v) remains free from visible particles, remains free from visible crystals, remains free from phase separation and/or remains free from ringing, when stored at room temperature, or at a refrigerated temperature, or at a frozen temperature, wherein the storage is for at least one day, at least one week, at least thirty days, or at least one year.

25. The liquid dilution composition of claim 24, wherein the aqueous medium is a beverage.

26. The liquid dilution composition of claim 25, wherein the beverage is water, soda, milk, juice or a sports or nutrition beverage.

27. A method for preparing a powder, comprising spray drying or freeze drying the liquid nanoemulsion concentrate of claim 1.

28. A method of providing a non-polar ingredient in a beverage, comprising:
adding a liquid nanoemulsion concentrate of claim 1 to an aqueous medium in an amount, whereby:
the aqueous medium contains an effective amount of the non-polar ingredient; and
the beverage containing the concentrate is as clear as in the absence of the non-polar ingredient.

29. The method of claim 28, wherein the beverage is water, soda, milk, juice or a sports or nutrition beverage.

30. The method of claim 28, wherein the non-polar ingredient is selected from among any one or more of polyunsaturated fatty acids, Coenzyme Q10 compounds, and phytosterols.

31. The liquid nanoemulsion concentrate of claim 1, wherein the amount of polysorbate or a polysorbate 80 analog is between 20% and about 26%, by weight, of the concentrate.

32. The liquid nanoemulsion concentrate of claim 1, wherein the polysorbate is polysorbate 80.

33. A method for preparing a liquid nanoemulsion concentrate, comprising:
(a) generating an oil phase by:
(i) mixing one or more first oil phase ingredients in a first vessel and heating the first oil phase ingredients at least until the first oil phase ingredients dissolve,
(ii) adding one or more additional oil phase ingredients to the first vessel, and
(iii) mixing and heating the first and the additional oil phase ingredients, wherein:
the oil phase ingredients comprise polysorbate or a polysorbate 80 analog in an amount between about 16% and about 30%, by weight, of the concentrate, and a non-polar ingredient, in an amount between about 5% and about 10%, by weight, of the concentrate; and the non-polar ingredient contains at least one polyunsaturated fatty acid selected from among omega-3 fatty acids, omega-6 fatty acids and conjugated fatty acids:
(b) generating a water phase by:
(i) mixing one or more water phase ingredients in a second vessel, and
(ii) heating the one or more water phase ingredients; and
(c) emulsifying the oil phase and the water phase, thereby generating a liquid nanoemulsion concentrate.

34. The method of claim 33, wherein the polysorbate 80 analog is a polysorbate 80 homolog.

35. The method of claim 34, wherein the polysorbate 80 homolog differs from polysorbate 80 by one or more methylene unit(s).

36. The method of claim 33, wherein the polysorbate 80 analog is polysorbate 60, polysorbate 40 or polysorbate 20.

37. The method of claim 33, wherein heating the oil phase ingredients and/or heating the water phase ingredients comprises heating the ingredients to between 45° C. or about 45° C. and 85° C. or about 85° C.

38. The method of claim 37, wherein heating the oil phase ingredients and/or heating the water phase ingredients comprises heating the ingredients to at or about 60° C.

39. The method of claim 33, wherein the emulsifying of the oil phase and the water phase is performed with a homogenizer.

40. The method of claim 33, further comprising rapidly cooling the forming emulsion during the emulsifying step, thereby cooling the forming emulsion to between 25° C. or about 25° C. and 35° C. or about 35° C.

41. The method of claim 40, wherein the rapid cooling comprises cooling the forming emulsion to between 25° C. or about 25° C. and 35° C. or about 35° C. in less than 60 minutes or less than about 60 minutes.

42. The method of claim 33, wherein the mixing and heating of the oil phase ingredients and/or the water phase ingredients are performed simultaneously.

43. The method of claim 33, wherein the non-polar ingredient contains a polyunsaturated fatty acid selected from among a docosahexaenoic acid (DHA), an eicosapentaenoic acid (EPA), a fish oil, a flaxseed oil, a borage oil, an alpha-linolenic acid (ALA), a gamma-linolenic acid (GLA), a conjugated linoleic acid (CLA) and a saw palmetto extract.

44. The method of claim 33, wherein the water phase ingredients contain water and the water is added at an amount between 60% or about 60% and 80% or about 80%, by weight, of the concentrate.

45. The method of claim 44, the water is added at an amount between about 60% and about 79%; or between about 65% and about 76%; or between about 68% and about 76%, by weight, of the concentrate.

46. The method of claim 33, wherein the polysorbate or polysorbate 80 analog is added at an amount is between about 17% and about 26%; or between about 18% and about 26%; or between about 20% and about 26%; or between about 16% and about 18%; or about 20%; or about 21%; or about 22%; or about 23%; or about 24%; or about 25%, by weight, of the concentrate.

47. The method of claim 33, wherein the first oil phase ingredients comprise the non-polar ingredient and at least one solvent.

48. The method of claim 47, wherein the solvent comprises an oil, other than the non-polar active ingredient.

49. The method of claim 33, wherein the oil phase or the water phase ingredients further comprise a co-surfactant, at an amount sufficient to stabilize the concentrate.

50. The method of claim 49, wherein the co-surfactant contains a phospholipid.

51. The method of claim 50, wherein the phospholipid comprises phosphatidylcholine.

52. The method of claim 33, wherein the oil phase or the water phase ingredients further comprise at least one preservative, in an amount sufficient to preserve the concentrate.

53. The method of claim 52, wherein the at least one preservative contains benzyl alcohol.

54. The method of claim 33, wherein the oil phase ingredients further comprise a solvent that dissolves the non-polar ingredient and differs therefrom, wherein the amount of solvent is sufficient to dissolve the non-polar active ingredient.

55. The method of claim 54, wherein the solvent comprises a Vitamin E oil or a flaxseed oil.

56. The method of claim 33, wherein the oil phase ingredients or the water phase ingredients, or the oil phase ingredients and the water phase ingredients further comprise an emulsion stabilizer, at an amount sufficient to stabilize the concentrate.

57. The method of claim 56, wherein the emulsion stabilizer comprises a blend of gums.

58. The method of claim 57, wherein the blend of gums contains gums selected from any one or more of guar gum, xanthan gum and sodium alginate.

59. The method of claim 33, further comprising adding one or more flavors to the concentrate, at an amount sufficient to enhance the taste of the concentrate, the smell of the concentrate, or a combination thereof.

60. The method of claim 59, wherein the one or more flavors comprises one or more of lemon oil and D-limonene.

61. A liquid nanoemulsion concentrate, comprising:
polysorbate or a polyoxyethylene sorbitan monooleate (polysorbate 80) analog in an amount of about 21%; or about 22%; or about 23%; or about 24%; or about 25%, by weight, up to about 30%, by weight, of the concentrate;
water in an amount between about 60% and about 79%, inclusive, by weight, of the concentrate; and
a non-polar ingredient that is selected from among any one or more of polyunsaturated fatty acids, Coenzyme Q10 compounds, and phytosterols in an amount between about 5% and about 10%, inclusive, by weight, of the concentrate, wherein the non-polar ingredient contains at least one polyunsaturated fatty acid selected from among any one or more of omega-3 fatty acids, omega-6 fatty acids and conjugated fatty acids.

62. The liquid nanoemulsion concentrate of claim 61, wherein the polysorbate is polysorbate 80.

63. A liquid nanoemulsion concentrate, comprising:
polysorbate or a polyoxyethylene sorbitan monooleate (polysorbate) 80 analog in an amount between about 16% and about 30%, inclusive, by weight, of the concentrate;
water in an amount between about 60% and about 79%, inclusive, by weight, of the concentrate; and
a non-polar ingredient that is selected from among any one or more of polyunsaturated fatty acids, and phytosterols in an amount between about 5% and about 10%, inclusive, by weight, of the concentrate, wherein the non-polar ingredient contains at least on polyunsaturated fatty acid selected from among any one or more omega-3 fatty acids, omega-6 fatty acids and conjugated fatty acids.

64. The liquid nanoemulsion concentrate of claim 63, wherein the polysorbate is polysorbate 80.

* * * * *

UNITED STATES PATENT AND TRADEMARK OFFICE
CERTIFICATE OF CORRECTION

PATENT NO. : 8,337,931 B2  
APPLICATION NO. : 12/456926  
DATED : December 25, 2012  
INVENTOR(S) : Philip J. Bromley Page 1 of 3

It is certified that error appears in the above-identified patent and that said Letters Patent is hereby corrected as shown below:

At column 47, line 61, please replace "Conjugated Linolenic acid" with --conjugated linoleic acid--.

At column 52, line 12 to line 13, please replace "Conjugated Linolenic acid" with --conjugated linoleic acid--.

At column 112, line 18 to line 19, please replace "conjugated linolenic acid" with --conjugated linoleic acid--.

Column 125, line 8 to line 48 should read
23. The liquid nanoemulsion concentrate of claim 1, wherein the concentrate is formulated such that:
(a) dilution of at least 0.5 g or about 0.5 g, at least 1 g or about 1 g, at least 2 g or about 2 g, at least 5 g or about 5 g, or at least 10 g or about 10 g of the concentrate into 8 fluid ounces (0.236588 liters), or about 8 fluid ounces, of an aqueous medium; or
(b) dilution of the concentrate in an aqueous medium, at a dilution of not more than 1:10 or about 1:10, not more than 1:25 or about 1:25, not more than 1:50 or about 1:50, not more than 1:100 or about 1:100, not more than 1:250 or about 1:250, or not more than 1:500 or about 1:500; or
(c) dilution of the concentrate into an aqueous medium to form a liquid dilution composition containing at least 25 mg or about 25 mg, at least 35 mg or about 35 mg, at least 50 mg or about 50 mg, at least 100 mg or about 100 mg, at least 250 mg or about 250 mg, or at least 500 mg or about 500 mg of the non-polar ingredient per 8 fluid ounces of the liquid dilution composition,
yields a liquid dilution composition:
(i) having a particle size of less than about 200 nm, less than about 100 nm, less than about 50 nm, or less than about 25 nm, at most or on average; or Signed and Sealed this  
Twenty-sixth Day of February, 2013

Teresa Stanek Rea  
*Acting Director of the United States Patent and Trademark Office*

CERTIFICATE OF CORRECTION (continued)
U.S. Pat. No. 8,337,931 B2

(ii) having a Nephelometric Turbidity Units (NTU) value of less than 200 or about 200, less than 100 or about 100, less than 50 or about 50, less than 30 or about 30, less than 25 or about 25, or less than 10 or about 10; or (iii) that does not contain visible particles, does not contain visible crystals, does not exhibit phase separation, and/or does not exhibit ringing; or (iv) that is at least as clear or at least about as clear as, the aqueous medium in the absence of the concentrate; or (v) that remains free from visible particles, remains free from visible crystals, remains free from phase separation, and/or remains free from ringing, when stored at room temperature, or at a refrigerated temperature, or at a frozen temperature, wherein the storage is for at least one day, at least one week, at least thirty days, or at least one year.

Column 125, line 49, to column 126, line 24 should read

24. A liquid dilution composition, comprising the liquid nanoemulsion concentrate of claim 1, diluted in an aqueous medium, wherein:

(a) the composition contains at least 0.5 grams (g) or about 0.5 g, at least 1 g or about 1 g, at least 2 g or about 2 g, at least 5 g or about 5 g, or at least 10 g or about 10 g of the concentrate, per 8 fluid ounces (0.236588 liters) of the aqueous medium; or (b) the composition contains the concentrate at a dilution of not more than 1:10 or about 1:10, not more than 1:25 or about 1:25, not more than 1:50 or about 1:50, not more than 1:100 or about 1:100, not more than 1:250 or about 1:250, or not more than 1:500 or about 1:500; or (c) the composition contains at least 25 mg or about 25 mg, at least 35 mg or about 35 mg, at least 50 mg or about 50 mg, at least 100 mg or about 100 mg, at least 250 mg or about 250 mg, or at least 500 mg or about 500 mg of the non-polar ingredient per 8 fluid ounces of the aqueous medium; and the liquid dilution composition:

(i) has a particle size of less than about 200 nm, less than about 100 nm, less than about 50 nm, or less than about 25 nm, on average or at the most; or (ii) has a Nephelometric Turbidity Units (NTU) value of less than 200 or about 200, less than 100 or about 100, less than 50 or about 50, less than 30 or about 30, less than 25 or about 25, or less than 10 or about 10; or (iii) does not contain visible particles, does not contain visible crystals, does not exhibit ringing, and/or does not exhibit phase separation; or (iv) is as clear or about as clear as the aqueous medium in the absence of the concentrate; or (v) remains free from visible particles, remains free from visible crystals, remains free from phase separation and/or remains free from ringing, when stored at room temperature, or at a refrigerated temperature, or at a frozen temperature, wherein the storage is for at least one day, at least one week, at least thirty days, or at least one year.

CERTIFICATE OF CORRECTION (continued)

Column 127, line 62 to line 63 should read

48. The method of claim 47, wherein the solvent comprises an oil, other than the non-polar ingredient.

Column 128, line 8 to line 11 should read

54. The method of claim 33, wherein the oil phase ingredients further comprise a solvent that dissolves the non-polar ingredient and differs therefrom, wherein the amount of solvent is sufficient to dissolve the non-polar ingredient.

Column 128, line 46 to line 62 should read

63. A liquid nanoemulsion concentrate, comprising:

polysorbate or a polyoxyethylene sorbitan monooleate (polysorbate 80) analog in an amount between about 16 % and about 30 %, inclusive, by weight, of the concentrate;

water in an amount between about 60 % and about 79%, inclusive, by weight, of the concentrate; and a non-polar ingredient that is selected from among any one or more of polyunsaturated fatty acids, and phytosterols in an amount between about 5 % and about 10 %, inclusive, by weight, of the concentrate, wherein the non-polar ingredient contains at least one polyunsaturated fatty acid selected from among any one or more of omega-3 fatty acids, omega-6 fatty acids and conjugated fatty acids.